(12) United States Patent
Ginggen et al.

(10) Patent No.: US 10,555,754 B2
(45) Date of Patent: Feb. 11, 2020

(54) METHODS AND APPARATUSES FOR SKIN TREATMENT USING NON-THERMAL TISSUE ABLATION

(71) Applicant: Cytrellis Biosystems, Inc., Woburn, MA (US)

(72) Inventors: Alec Ginggen, Plymouth, MA (US); Douglas Levinson, Sherborn, MA (US); David Stone, Acton, MA (US)

(73) Assignee: Cytrellis Biosystems, Inc., Woburn, MA (US)

( * ) Notice: Subject to any disclaimer, the term of this patent is extended or adjusted under 35 U.S.C. 154(b) by 368 days.

(21) Appl. No.: 14/910,767

(22) PCT Filed: Aug. 8, 2014

(86) PCT No.: PCT/US2014/050426
§ 371 (c)(1),
(2) Date: Feb. 8, 2016

(87) PCT Pub. No.: WO2015/021434
PCT Pub. Date: Feb. 12, 2015

(65) Prior Publication Data
US 2016/0192961 A1    Jul. 7, 2016

Related U.S. Application Data

(60) Provisional application No. 61/864,281, filed on Aug. 9, 2013.

(51) Int. Cl.
*A61B 17/3209* (2006.01)
*A61B 18/02* (2006.01)
(Continued)

(52) U.S. Cl.
CPC ........ *A61B 17/32093* (2013.01); *A61B 17/14* (2013.01); *A61B 17/3203* (2013.01);
(Continued)

(58) Field of Classification Search
CPC .................. A61B 17/14; A61B 17/147; A61B 17/320068; A61B 17/3203;
(Continued)

(56) References Cited

U.S. PATENT DOCUMENTS 2,426,535 A   8/1947   Turkel
2,496,111 A   1/1950   Turkel
(Continued)

FOREIGN PATENT DOCUMENTS

CA      1275215 C    10/1990
CA      2361777 A1    5/2002
(Continued)

OTHER PUBLICATIONS

Bedi et al., "The effects of pulse energy variations on the dimensions of microscopic thermal treatment zones in nonablative fractional resurfacing," Lasers Surg Med. 39(2):145-55 (2007).
(Continued)

*Primary Examiner* — Brandy S Lee
(74) *Attorney, Agent, or Firm* — Choate, Hall & Stewart LLP; Brenda H. Jarrell; Alexander D. Augst

(57) ABSTRACT

Disclosed herein are methods, apparatuses, and devices for treating skin, such as skin tightening or for treating diseases, disorders, and conditions that would benefit from tissue area or volume reduction, skin restoration, skin tightening, skin lifting, or skin repositioning. Such methods and devices include an ablative apparatus, a removal apparatus, and/or a positioning apparatus.

23 Claims, 23 Drawing Sheets

(51) Int. Cl.
  *A61B 17/14* (2006.01)
  *A61B 17/3203* (2006.01)
  *A61B 17/3205* (2006.01)
  *A61B 17/34* (2006.01)
  *A61B 18/14* (2006.01)
  *A61B 18/20* (2006.01)
  *A61B 17/32* (2006.01)
  *A61B 18/00* (2006.01)
  *A61B 17/00* (2006.01)

(52) U.S. Cl.
  CPC ........ *A61B 17/32053* (2013.01); *A61B 17/34* (2013.01); *A61B 18/02* (2013.01); *A61B 18/14* (2013.01); *A61B 18/20* (2013.01); *A61B 2017/00039* (2013.01); *A61B 2017/00084* (2013.01); *A61B 2017/00765* (2013.01); *A61B 2017/32007* (2017.08); *A61B 2017/320069* (2017.08); *A61B 2017/320082* (2017.08); *A61B 2018/0016* (2013.01); *A61B 2018/0047* (2013.01); *A61B 2018/00577* (2013.01); *A61B 2018/0262* (2013.01); *A61B 2018/0293* (2013.01); *A61B 2018/143* (2013.01); *A61B 2018/2005* (2013.01)

(58) Field of Classification Search
  CPC ........ A61B 17/32053; A61B 17/32093; A61B 17/34; A61B 18/02; A61B 18/14; A61B 18/20; A61B 18/203; A61B 2017/00039; A61B 2017/00084; A61B 2017/00747; A61B 2017/00756; A61B 2017/00765; A61B 2017/00769; A61B 2018/0016; A61B 2018/0047; A61B 2018/00577; A61B 2018/00613; A61B 2018/0262; A61B 2018/0293; A61B 2018/143; A61B 2018/2005; A61B 2017/320069; A61B 2017/32007; A61B 2017/320082; A61M 37/0015; A61M 2025/0073
  See application file for complete search history.

(56) References Cited

U.S. PATENT DOCUMENTS

| | | | |
|---|---|---|---|
| 2,881,763 | A | 4/1959 | Robbins |
| 3,001,522 | A | 9/1961 | Silverman |
| 3,214,869 | A | 11/1965 | Stryker |
| 3,598,108 | A | 8/1971 | Jamshidi et al. |
| 3,683,892 | A | 8/1972 | Harris |
| 3,788,320 | A | 1/1974 | Dye |
| 3,929,123 | A | 12/1975 | Jamshidi |
| 4,108,096 | A | 8/1978 | Ciecior |
| 4,159,659 | A | 7/1979 | Nightingale |
| 4,403,617 | A | 9/1983 | Tretinyak |
| 4,458,678 | A | 7/1984 | Yannas et al. |
| 4,476,864 | A | 10/1984 | Tezel |
| 4,604,346 | A | 8/1986 | Bell et al. |
| 4,640,296 | A | 2/1987 | Schnepp-Pesch et al. |
| 4,649,918 | A | 3/1987 | Pegg et al. |
| D297,375 | S | 8/1988 | Liu |
| 4,815,462 | A | 3/1989 | Clark |
| 4,865,026 | A | 9/1989 | Barrett |
| 4,903,709 | A | 2/1990 | Skinner |
| D323,034 | S | 1/1992 | Reinstein |
| 5,152,763 | A | 10/1992 | Johnson |
| D338,070 | S | 8/1993 | Lam |
| D342,138 | S | 12/1993 | Wollman et al. |
| 5,269,316 | A | 12/1993 | Spitalny |
| 5,306,490 | A | 4/1994 | Barley, Jr. |
| 5,324,305 | A | 6/1994 | Kanner |
| 5,331,972 | A | 7/1994 | Wadhwani et al. |
| 5,415,182 | A | 5/1995 | Chin et al. |
| 5,419,761 | A | 5/1995 | Narayanan et al. |
| 5,439,475 | A | 8/1995 | Bennett |
| 5,458,112 | A | 10/1995 | Weaver |
| D377,404 | S | 1/1997 | Izumi |
| 5,593,381 | A | 1/1997 | Tannenbaum et al. |
| 5,611,810 | A | 3/1997 | Arnold et al. |
| 5,615,690 | A | 4/1997 | Giurtino et al. |
| 5,639,654 | A | 6/1997 | Bernard et al. |
| D388,543 | S | 12/1997 | Eguchi et al. |
| 5,713,375 | A | 2/1998 | McAllister |
| 5,749,895 | A | 5/1998 | Sawyer et al. |
| 5,792,169 | A | 8/1998 | Markman |
| 5,810,857 | A | 9/1998 | Mackool |
| 5,827,297 | A | 10/1998 | Boudjema |
| 5,868,744 | A | 2/1999 | Willmen |
| 5,879,326 | A | 3/1999 | Godshall et al. |
| 5,885,211 | A | 3/1999 | Eppstein et al. |
| 5,885,226 | A | 3/1999 | Rubinstein et al. |
| 5,902,319 | A | 5/1999 | Daley |
| 5,922,000 | A | 7/1999 | Chodorow |
| 5,925,002 | A | 7/1999 | Wollman |
| 5,928,162 | A | 7/1999 | Giurtino et al. |
| 5,931,855 | A | 8/1999 | Buncke |
| 5,989,273 | A | 11/1999 | Arnold |
| 6,022,324 | A | 2/2000 | Skinner |
| D425,241 | S | 5/2000 | Nishizawa et al. |
| 6,059,807 | A | 5/2000 | Boudjema |
| 6,063,094 | A | 5/2000 | Rosenberg |
| 6,178,346 | B1 | 1/2001 | Amundson et al. |
| 6,197,039 | B1 | 3/2001 | Ashraf |
| 6,211,598 | B1 | 4/2001 | Dhuler et al. |
| 6,241,687 | B1 | 6/2001 | Voegele et al. |
| 6,241,739 | B1 | 6/2001 | Waldron |
| 6,251,097 | B1 | 6/2001 | Kline et al. |
| 6,264,618 | B1 | 7/2001 | Landi et al. |
| 6,342,213 | B1 | 1/2002 | Barley et al. |
| D457,265 | S | 5/2002 | Gebhard |
| D458,710 | S | 6/2002 | Altamore et al. |
| 6,432,098 | B1 | 8/2002 | Kline et al. |
| 6,440,086 | B1 | 8/2002 | Hohenberg |
| 6,461,369 | B1 | 10/2002 | Kim |
| 6,537,264 | B1 | 3/2003 | Cormier et al. |
| 6,562,037 | B2 | 5/2003 | Paton et al. |
| 6,669,618 | B2 | 12/2003 | Reising et al. |
| 6,669,694 | B2 | 12/2003 | Shadduck |
| 6,733,496 | B2 | 5/2004 | Sharkey et al. |
| 6,733,498 | B2 | 5/2004 | Paton et al. |
| D500,391 | S | 12/2004 | Nielsen et al. |
| 6,881,203 | B2 | 4/2005 | Delmore et al. |
| 6,887,250 | B1 | 5/2005 | Dority et al. |
| 6,893,388 | B2 | 5/2005 | Reising et al. |
| 6,936,039 | B2 | 8/2005 | Kline et al. |
| D509,301 | S | 9/2005 | Talbot et al. |
| 6,997,923 | B2 | 2/2006 | Anderson et al. |
| 7,073,510 | B2 | 7/2006 | Redmond et al. |
| 7,131,951 | B2 | 11/2006 | Angel |
| D538,430 | S | 3/2007 | Ohta |
| 7,651,507 | B2 | 1/2010 | Mishra et al. |
| 7,658,728 | B2 | 2/2010 | Yuzhakov |
| 7,926,401 | B2 | 4/2011 | Mishra et al. |
| 8,128,639 | B2 | 3/2012 | Tippett et al. |
| 8,209,006 | B2 | 6/2012 | Smith et al. |
| 8,226,664 | B2 | 7/2012 | Drews et al. |
| 8,246,611 | B2 | 8/2012 | Paithankar et al. |
| 8,435,791 | B2 | 5/2013 | Galun et al. |
| 8,480,592 | B2 | 7/2013 | Chudzik et al. |
| 8,696,686 | B2 | 4/2014 | Drews et al. |
| 8,900,181 | B2 | 12/2014 | Knowlton |
| 9,017,343 | B2 | 4/2015 | Westerling, Jr. et al. |
| 9,060,803 | B2 | 6/2015 | Anderson et al. |
| 9,084,465 | B2 | 7/2015 | Oostman, Jr. et al. |
| 9,119,945 | B2 | 9/2015 | Simons et al. |
| 9,439,673 | B2 | 9/2016 | Austen |
| 9,561,051 | B2 | 2/2017 | Austen et al. |
| D797,286 | S | 9/2017 | Ginggen et al. |
| 10,251,792 | B2 | 4/2019 | Levinson et al. |
| 2002/0022854 | A1 | 2/2002 | Irion et al. |
| 2002/0022861 | A1 | 2/2002 | Jacobs et al. |
| 2002/0045859 | A1 | 4/2002 | Gartstein et al. |
| 2002/0103500 | A1 | 8/2002 | Gildenberg |

(56) References Cited

U.S. PATENT DOCUMENTS

| | | |
|---|---|---|
| 2002/0120260 A1 | 8/2002 | Morris et al. |
| 2002/0169431 A1 | 11/2002 | Kline et al. |
| 2002/0183688 A1 | 12/2002 | Lastovich et al. |
| 2002/0188280 A1 | 12/2002 | Nguyen et al. |
| 2003/0023196 A1 | 1/2003 | Liguori |
| 2003/0083607 A1* | 5/2003 | Bobo, Jr. ............... A61B 18/24 604/20 |
| 2003/0088220 A1 | 5/2003 | Molander et al. |
| 2003/0119641 A1 | 6/2003 | Reising |
| 2003/0135161 A1 | 7/2003 | Fleming et al. |
| 2003/0158521 A1 | 8/2003 | Ameri |
| 2003/0158566 A1 | 8/2003 | Brett |
| 2003/0163160 A1 | 8/2003 | O'Malley et al. |
| 2003/0181936 A1 | 9/2003 | Trautman et al. |
| 2003/0195625 A1 | 10/2003 | Garcia Castro et al. |
| 2003/0199811 A1 | 10/2003 | Sage et al. |
| 2003/0233082 A1 | 12/2003 | Kline et al. |
| 2004/0002723 A1 | 1/2004 | Ball |
| 2004/0010268 A1 | 1/2004 | Gabehart |
| 2004/0015139 A1 | 1/2004 | La Bianco et al. |
| 2004/0023771 A1 | 2/2004 | Reising et al. |
| 2004/0054410 A1 | 3/2004 | Barrows |
| 2004/0073195 A1 | 4/2004 | Cucin |
| 2004/0122471 A1 | 6/2004 | Toby et al. |
| 2004/0162566 A1 | 8/2004 | Carson et al. |
| 2004/0175690 A1 | 9/2004 | Mishra et al. |
| 2004/0220589 A1 | 11/2004 | Feller |
| 2005/0049582 A1 | 3/2005 | DeBenedictis et al. |
| 2005/0090765 A1 | 4/2005 | Fisher |
| 2005/0130821 A1 | 6/2005 | Reising et al. |
| 2005/0165329 A1 | 7/2005 | Taylor et al. |
| 2005/0203575 A1 | 9/2005 | Carson et al. |
| 2005/0209567 A1 | 9/2005 | Sibbitt |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0226856 A1 | 10/2005 | Ahlfors |
| 2005/0234419 A1 | 10/2005 | Kline et al. |
| 2005/0245952 A1 | 11/2005 | Feller |
| 2005/0283141 A1 | 12/2005 | Giovannoli |
| 2006/0047234 A1 | 3/2006 | Glucksman et al. |
| 2006/0064031 A1 | 3/2006 | Miller |
| 2006/0116605 A1 | 6/2006 | Nakao |
| 2006/0155266 A1 | 7/2006 | Manstein et al. |
| 2006/0161179 A1 | 7/2006 | Kachenmeister |
| 2006/0184153 A1 | 8/2006 | Mark et al. |
| 2006/0216781 A1 | 9/2006 | Gebing |
| 2006/0259006 A1 | 11/2006 | McKay et al. |
| 2006/0264926 A1 | 11/2006 | Kochamba |
| 2006/0271070 A1 | 11/2006 | Eriksson et al. |
| 2006/0276806 A1 | 12/2006 | Martinez Zunino |
| 2007/0010810 A1 | 1/2007 | Kochamba |
| 2007/0038181 A1 | 2/2007 | Melamud et al. |
| 2007/0038236 A1 | 2/2007 | Cohen |
| 2007/0060888 A1 | 3/2007 | Goff et al. |
| 2007/0073217 A1 | 3/2007 | James |
| 2007/0073327 A1 | 3/2007 | Giovannoli |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0142885 A1 | 6/2007 | Hantash et al. |
| 2007/0149991 A1 | 6/2007 | Mulholland |
| 2007/0156161 A1 | 7/2007 | Weadock et al. |
| 2007/0167958 A1 | 7/2007 | Sulamanidze et al. |
| 2007/0179455 A1 | 8/2007 | Geliebter et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239236 A1 | 10/2007 | Manstein |
| 2007/0239260 A1 | 10/2007 | Palanker et al. |
| 2007/0249960 A1 | 10/2007 | Williamson |
| 2007/0270710 A1 | 11/2007 | Frass et al. |
| 2008/0009802 A1 | 1/2008 | Lambino et al. |
| 2008/0009901 A1 | 1/2008 | Redmond et al. |
| 2008/0033334 A1 | 2/2008 | Gurtner et al. |
| 2008/0045858 A1 | 2/2008 | Tessitore et al. |
| 2008/0045861 A1 | 2/2008 | Miller et al. |
| 2008/0132979 A1 | 6/2008 | Gerber |
| 2008/0146982 A1 | 6/2008 | Rastegar et al. |
| 2008/0183167 A1 | 7/2008 | Britva et al. |
| 2008/0208146 A1 | 8/2008 | Brandwein et al. |
| 2008/0221548 A1 | 9/2008 | Danenberg et al. |
| 2008/0234602 A1 | 9/2008 | Oostman et al. |
| 2008/0234699 A1 | 9/2008 | Oostman, Jr. et al. |
| 2008/0269735 A1 | 10/2008 | Vila Echague et al. |
| 2008/0275378 A1 | 11/2008 | Herndon |
| 2008/0300507 A1 | 12/2008 | Figueredo et al. |
| 2008/0306471 A1 | 12/2008 | Altshuler et al. |
| 2008/0312648 A1 | 12/2008 | Peterson |
| 2009/0030340 A1 | 1/2009 | McClellan |
| 2009/0048557 A1 | 2/2009 | Yeshurun et al. |
| 2009/0093864 A1 | 4/2009 | Anderson |
| 2009/0146068 A1 | 6/2009 | Agarwal |
| 2009/0198336 A1 | 8/2009 | Qiao et al. |
| 2009/0227895 A1 | 9/2009 | Goldenberg |
| 2009/0312749 A1 | 12/2009 | Pini et al. |
| 2010/0023003 A1 | 1/2010 | Mulholland |
| 2010/0041938 A1 | 2/2010 | Stoianovici et al. |
| 2010/0057100 A1 | 3/2010 | Zeevi |
| 2010/0082042 A1 | 4/2010 | Drews |
| 2010/0121307 A1 | 5/2010 | Lockard et al. |
| 2010/0145373 A1 | 6/2010 | Alon |
| 2010/0160822 A1 | 6/2010 | Parihar et al. |
| 2010/0185116 A1 | 7/2010 | Al-Mohizea |
| 2010/0330589 A1 | 12/2010 | Bahrami et al. |
| 2011/0009882 A1 | 1/2011 | Remsburg et al. |
| 2011/0028898 A1 | 2/2011 | Clark, III et al. |
| 2011/0040497 A1 | 2/2011 | Olesen |
| 2011/0092844 A1 | 4/2011 | Bargo et al. |
| 2011/0105949 A1 | 5/2011 | Wiksell |
| 2011/0152738 A1 | 6/2011 | Zepeda et al. |
| 2011/0172745 A1 | 7/2011 | Na et al. |
| 2011/0245834 A1 | 10/2011 | Miklosovic |
| 2011/0251602 A1 | 10/2011 | Anderson et al. |
| 2011/0270274 A1 | 11/2011 | Hull, Jr. |
| 2011/0282238 A1 | 11/2011 | Houser et al. |
| 2011/0313429 A1 | 12/2011 | Anderson et al. |
| 2012/0041430 A1 | 2/2012 | Anderson et al. |
| 2012/0065551 A1 | 3/2012 | Aviad et al. |
| 2012/0136387 A1 | 5/2012 | Redmond et al. |
| 2012/0158100 A1 | 6/2012 | Schomacker |
| 2012/0209283 A1 | 8/2012 | Zhu |
| 2012/0226214 A1 | 9/2012 | Gurtner et al. |
| 2012/0226268 A1 | 9/2012 | Liu et al. |
| 2012/0226306 A1 | 9/2012 | Jackson et al. |
| 2012/0245629 A1 | 9/2012 | Gross et al. |
| 2012/0253333 A1 | 10/2012 | Garden et al. |
| 2012/0271320 A1* | 10/2012 | Hall ............... A61B 17/32053 606/132 |
| 2013/0006168 A1 | 1/2013 | Del Vecchio |
| 2013/0045171 A1 | 2/2013 | Utecht et al. |
| 2013/0110026 A1 | 5/2013 | Jackson et al. |
| 2013/0131635 A1 | 5/2013 | Rimsa et al. |
| 2013/0204238 A1 | 8/2013 | Lederman et al. |
| 2014/0036523 A1 | 2/2014 | Thullier et al. |
| 2014/0039523 A1 | 2/2014 | Austen |
| 2014/0163582 A1 | 6/2014 | Austen et al. |
| 2014/0200484 A1 | 7/2014 | Austen et al. |
| 2014/0277055 A1 | 9/2014 | Austen, Jr. |
| 2014/0296741 A1 | 10/2014 | Austen |
| 2014/0296796 A1 | 10/2014 | Lim |
| 2014/0303648 A1 | 10/2014 | Knowlton |
| 2015/0143713 A1 | 5/2015 | Cheng |
| 2015/0173991 A1 | 6/2015 | Anderson et al. |
| 2015/0238214 A1 | 8/2015 | Anderson et al. |
| 2015/0258319 A1 | 9/2015 | Simmers |
| 2015/0320990 A1 | 11/2015 | Burton et al. |
| 2015/0366719 A1 | 12/2015 | Levinson et al. |
| 2016/0082241 A1 | 3/2016 | Burton et al. |
| 2016/0095592 A1 | 4/2016 | Levinson et al. |
| 2016/0121091 A1 | 5/2016 | Burton et al. |
| 2016/0136406 A1 | 5/2016 | Berry et al. |

(56) References Cited

U.S. PATENT DOCUMENTS

| | | |
|---|---|---|
| 2016/0317721 A1 | 11/2016 | Ginggen et al. |
| 2016/0367280 A1 | 12/2016 | Austen |
| 2017/0367729 A1 | 12/2017 | Ginggen et al. |
| 2018/0008500 A1 | 1/2018 | Anderson et al. |
| 2018/0021087 A1 | 1/2018 | Anderson et al. |
| 2018/0078278 A1 | 3/2018 | Levinson et al. |
| 2018/0185196 A1 | 7/2018 | Levinson et al. |
| 2018/0193054 A1 | 7/2018 | Austen |
| 2018/0206875 A1 | 7/2018 | Austen et al. |
| 2019/0099199 A1 | 4/2019 | Levinson et al. |

FOREIGN PATENT DOCUMENTS

| | | |
|---|---|---|
| CN | 2126570 Y | 1/1993 |
| CN | 1115629 A | 1/1996 |
| CN | 201005966 Y | 1/2008 |
| CN | 101128156 A | 2/2008 |
| CN | 101208128 A | 6/2008 |
| CN | 101232858 A | 7/2008 |
| CN | 101277657 A | 10/2008 |
| CN | 101312692 A | 11/2008 |
| CN | 101347346 A | 1/2009 |
| CN | 101670145 A | 3/2010 |
| CN | 202113484 U | 1/2012 |
| CN | 103547226 A | 1/2014 |
| DE | 287651 A5 | 3/1991 |
| DE | 202004010659 U1 | 10/2004 |
| DE | 102007026973 A1 | 12/2008 |
| EP | 0027974 A1 | 5/1981 |
| EP | 1224949 A1 | 7/2002 |
| EP | 1278061 A1 | 1/2003 |
| EP | 1396230 A1 | 3/2004 |
| EP | 2181732 A1 | 5/2010 |
| EP | 1278061 B1 | 2/2011 |
| EP | 2409727 A1 | 1/2012 |
| FR | 2846221 B1 | 7/2005 |
| JP | S57-163208 A | 10/1982 |
| JP | 2000-139929 A | 5/2000 |
| JP | 2001-187058 A | 7/2001 |
| JP | 2002-505605 A | 2/2002 |
| JP | 2003-515424 A | 5/2003 |
| JP | 2003-532480 A | 11/2003 |
| JP | 2004-503342 A | 2/2004 |
| JP | 2005-000642 A | 1/2005 |
| JP | 2005-103276 A | 4/2005 |
| JP | 2006-516201 A | 6/2006 |
| JP | 2006-517814 A | 8/2006 |
| JP | 2007-041267 A | 2/2007 |
| JP | 2007-100140 A | 4/2007 |
| JP | 2008-036393 A | 2/2008 |
| JP | 2008-528207 A | 7/2008 |
| JP | 2009-507773 A | 2/2009 |
| JP | 2009-509671 A | 3/2009 |
| JP | 2009-172418 A | 8/2009 |
| JP | 2009-219858 A | 10/2009 |
| JP | 2009-545382 A | 12/2009 |
| JP | 2010-000210 A | 1/2010 |
| JP | 4431637 B2 | 3/2010 |
| JP | 2010-515469 A | 5/2010 |
| JP | 2010-525887 A | 7/2010 |
| JP | 2010-532178 A | 10/2010 |
| JP | 2011-516169 A | 5/2011 |
| JP | 5944925 B2 | 7/2016 |
| KR | 2008-0030553 A | 4/2008 |
| KR | 2008-0049793 A | 6/2008 |
| KR | 2010-0135863 A | 12/2010 |
| KR | 2010-0135864 A | 12/2010 |
| RU | 1801391 A1 | 3/1993 |
| RU | 2119304 C1 | 9/1998 |
| RU | 58359 U1 | 11/2006 |
| RU | 2289332 C2 | 12/2006 |
| RU | 2308873 C2 | 10/2007 |
| RU | 2325859 C2 | 6/2008 |
| TW | 402497 B | 8/2000 |
| TW | 200841866 A | 11/2008 |
| WO | WO-93/22971 A1 | 11/1993 |
| WO | WO-1995/28896 A1 | 11/1995 |
| WO | WO-97/18758 A1 | 5/1997 |
| WO | WO-98/26719 A1 | 6/1998 |
| WO | WO-98/57587 A1 | 12/1998 |
| WO | WO-99/29243 A1 | 6/1999 |
| WO | WO-0141651 A2 | 6/2001 |
| WO | WO-01/85035 A2 | 11/2001 |
| WO | WO-02/05890 A2 | 1/2002 |
| WO | WO-02/096321 A1 | 12/2002 |
| WO | WO-2004/045671 A2 | 6/2004 |
| WO | WO-2005/013830 A1 | 2/2005 |
| WO | WO-2005/072181 A2 | 8/2005 |
| WO | WO-2005/109799 A2 | 11/2005 |
| WO | WO-2006/081556 A2 | 8/2006 |
| WO | WO-2006/116281 A2 | 11/2006 |
| WO | WO-2006/118804 A1 | 11/2006 |
| WO | WO-2007/011788 A2 | 1/2007 |
| WO | WO-2007/015232 A1 | 2/2007 |
| WO | WO-2007/024038 A1 | 3/2007 |
| WO | WO-2007/041267 A2 | 4/2007 |
| WO | WO-2007/080596 A2 | 7/2007 |
| WO | WO-2007/106170 A2 | 9/2007 |
| WO | WO-2008/019051 A2 | 2/2008 |
| WO | WO-2008/033873 A2 | 3/2008 |
| WO | WO-2008/052189 A2 | 5/2008 |
| WO | WO-2009/040493 A1 | 4/2009 |
| WO | WO-2009/072711 A2 | 6/2009 |
| WO | WO-2009/099988 A2 | 8/2009 |
| WO | WO-2009/137288 A2 | 11/2009 |
| WO | WO-2009/146053 A1 | 12/2009 |
| WO | WO-2009/146068 A1 | 12/2009 |
| WO | WO-2009/146072 A1 | 12/2009 |
| WO | WO-2010/027188 A2 | 3/2010 |
| WO | WO-2010/080014 A2 | 7/2010 |
| WO | WO-2010/097790 A1 | 9/2010 |
| WO | WO-2011/006009 A1 | 1/2011 |
| WO | WO-2011/019859 A2 | 2/2011 |
| WO | WO-2011/075676 A2 | 6/2011 |
| WO | WO-2011/104875 A1 | 9/2011 |
| WO | WO-2011/123218 A1 | 10/2011 |
| WO | WO-2011/075676 A3 | 11/2011 |
| WO | WO-2011/140497 A2 | 11/2011 |
| WO | WO-2012/052986 A2 | 4/2012 |
| WO | WO-2012/103483 A2 | 8/2012 |
| WO | WO-2012/103488 A1 | 8/2012 |
| WO | WO-2012/103492 A1 | 8/2012 |
| WO | WO-2012/119131 A1 | 9/2012 |
| WO | WO-2012/135828 A1 | 10/2012 |
| WO | WO-2013/013196 A1 | 1/2013 |
| WO | WO-2013/013199 A2 | 1/2013 |
| WO | WO-2014/008470 A1 | 1/2014 |
| WO | WO-2014/089488 A2 | 6/2014 |
| WO | WO-2014/130359 A1 | 8/2014 |
| WO | WO-2014/151104 A1 | 9/2014 |
| WO | WO-2014/179729 A1 | 11/2014 |
| WO | WO-2015/021434 A2 | 2/2015 |
| WO | WO-2015/051164 A2 | 4/2015 |
| WO | WO-2015/095675 A1 | 6/2015 |
| WO | WO-2015/126926 A1 | 8/2015 |
| WO | WO-2016/033584 A1 | 3/2016 |
| WO | WO-2016/033586 A1 | 3/2016 |
| WO | WO-2016/077759 A1 | 5/2016 |
| WO | WO-2016/127091 A1 | 8/2016 |
| WO | WO-2017/139773 A2 | 8/2017 |
| WO | WO-2017/172920 A1 | 10/2017 |
| WO | WO-2017/192723 A1 | 11/2017 |
| WO | WO-2018/057630 A1 | 3/2018 |
| WO | WO-2018/057637 A1 | 3/2018 |

OTHER PUBLICATIONS

Cevc, "Drug delivery across the skin," Expert Opin Investig Drugs. 6(12):1887-937 (1997).

Chang, "An updated review of tyrosinase inhibitors," Int J Mol Sci. 10(6):2440-2475 (2009).

Czech et al., Pressure-sensitive adhesives for medical applications. *Wide Spectra of Quality Control.* Akyar, 309-332 (2011).

(56) References Cited

OTHER PUBLICATIONS

Dai et al., "Magnetically-responsive self assembled composites," Chem Soc Rev. 39(11):4057-66 (2010.).
De las Heras Alarcon et al., "Stimuli responsive polymers for biomedical applications," Chem Soc Rev. 34(3):276-85 (2005).
Dini et al., "Grasping leather plies by Bernoulli grippers," CIRP Ann Manuf Technol. 58(1):21-4 (2009).
Dujardin et al., "In vivo assessment of skin electroporation using square wave pulses," J Control Release. 79(1-3):219-27 (2002).
Dunkin et al., "Scarring occurs at a critical depth of skin injury: precise measurement in a graduated dermal scratch in human volunteers," Plast Reconstr Surg. 119(6):1722-32 (2007).
European Supplemental Search Report for European Patent Application No. 12739664.6 dated Jun. 6, 2014 (1 page).
Examination Report for Australian Application No. 2012211118, dated Aug. 3, 2015 (3 pages).
Examination Report for Australian Application No. 2012211122, dated Aug. 5, 2015 (4 pages).
Extended European Search Report for European Patent Application No. 12739664.6, dated May 20, 2014 (7 pages).
Extended European Search Report for European Patent Application No. 13813955.5, dated Mar. 18, 2016 (6 pages).
Fernandes et al., "Micro-mechanical fractional skin rejuvenation," Plast Reconstr Surg. 130(5S-1):28 (2012).
Fernandes et al., "Micro-mechanical fractional skin rejuvenation," Plast Reconstr Surg. 131(2):216-23 (2013).
First Office Action for Chinese Application 201280010967.7 dated Apr. 24, 2015 (7 pages).
First Office Action for Chinese Application 201280011095.6, dated May 19, 2015 (9 pages).
Galaev., "'Smart' polymers in biotechnology and medicine," Russ Chem Rev. 64(5):471-489 (1995).
Glogau, "Aesthetic and anatomic analysis of the aging skin," Semin Cutan Med Surg. 15(3):134-8 (1996).
Hale et al., "Optical constants of water in the 200-nm to 200-microm wavelength region," Appl Opt. 12(3):555-63 (1973).
Huang et al., "Shape memory materials," Material Today 13(7-8):54-61 (2010).
International Preliminary Report on Patentability for International Patent Application No. PCT/US2009/039125, dated Oct. 5, 2010 (6 pages).
International Preliminary Report on Patentability for International Patent Application No. PCT/US2012/022987, dated Jul. 30, 2013 (5 pages).
International Preliminary Report on Patentability for International Patent Application No. PCT/US2012/022993, dated Jul. 30, 2013 (1 page).
International Preliminary Report on Patentability for International Patent Application No. PCT/US2012/047716, dated Nov. 4, 2014 (4 pages).
International Preliminary Report on Patentability for International Patent Application No. PCT/US2013/049445, dated Jan. 6, 2015 (4 pages).
International Preliminary Report on Patentability for International Patent Application No. PCT/US2014/036638, dated Nov. 3, 2015 (7 pages).
International Preliminary Report on Patentability for International Patent Application No. PCT/US2014/050426, dated Feb. 9, 2016 (8 pages).
International Search Report and Written Opinion for International Patent Application No. PCT/US2009/039125, dated Nov. 16, 2009 (9 pages).
International Search Report and Written Opinion for International Patent Application No. PCT/US2012/022987, dated Apr. 12, 2012 (6 pages).
International Search Report and Written Opinion for International Patent Application No. PCT/US2012/022993, dated May 17, 2012 (6 pages).
International Search Report and Written Opinion for International Patent Application No. PCT/US2012/047716, dated Oct. 25, 2012 (5 pages).
International Search Report and Written Opinion for International Patent Application No. PCT/US2013/049445, dated Oct. 18, 2013 (6 pages).
International Search Report and Written Opinion for International Patent Application No. PCT/US2014/016483, dated May 6, 2014 (15 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (18 pages).
Kakasheva-Mazenkovska et al., "Variations of the histomorphological characteristics of human skin of different body regions in subjects of different age," Contributions. 32(2):119-28 (2011).
Konermann et al., "Ultrasonographically guided needle biopsy of benign and malignant soft tissue and bone tumors," J Ultrasound Med. 19(7):465-71 (2000).
Lien et al., "A novel gripper for limp materials based on lateral Coanda ejectors," CIRP Ann Manuf Technol. 57(1):33-6 (2008).
Majid, "Microneedling therapy in atrophic facial scars: an objective assessment," J Cutan Aesthet Surg. 2(1):26-30 (2009) (11 pages).
Notice of Reasons for Rejection and English Translation for Japanese Application No. 2013-551385, dated Nov. 10, 2015 (5 pages).
Notice of Reasons for Rejection and English Translation for Japanese Application No. 2013-551387, dated Aug. 18, 2015 (6 pages).
Pliquett et al., "A propagating heat wave model of skin electroporation," J Theor Biol. 251(2):195-201 (2008).
Prausnitz et al., "Electroporation of mammalian skin: a mechanism to enhance transdermal drug delivery," Proc Natl Acad Sci U S A. 90(22):10504-8 (1993).
Salam et al., "The basic Z-plasty," Am Fam Physician. 67(11):2329-32 (2003).
Translated Office Action for Mexican National Patent Application No. MX/a/2013008720, dated Sep. 2, 2015 (2 pages).
Alsberg, E. et al., Engineering growing tissues, PNAS, 99(19):12025-12030 (2002).
Banzhaf, C. et al., Spatiotemporal Closure of Fractional Laser-Ablated Channels Imaged by Optical Coherence Tomography and Reflectance Confocal Microscopy, Lasers in Surgery and Medicine, 48:157-165 (2016).
International Search Report for International Patent Application No. PCT/US2012/022980 dated Aug. 9, 2012.
International Written Opinion for International Patent Application No. PCT/US2012/022980 dated Aug. 9, 2012.
European Patent Office, Supplementary European Search Report, Application No. EP13813955.5, dated Mar. 18, 2016.
European Search Report for European Application No. 12739664.6 dated May 20, 2014.
Extended European Search Report, Application No. 12814711.3, dated Feb. 11, 2015.
Han, H. et al., Combined, Minimally Invasive, Thread-based Facelift, Archives of Aesthetic Plastic Surgery, 20(3):160-164 (2014).
International Search Report and Written Opinion for PCT/US2011/035613, dated May 6, 2011.
International Search Report and Written Opinion issued by the Korean Intellectual Property Office as International Searching Authority for International Application No. PCT/US2009/039114 dated Nov. 16, 2009 (10 pages).
International Search Report and Written Opinion dated Oct. 18, 2013 in connection with PCT/US2013/049445.
International Search Report for International Patent Application No. PCT/US2012/047708.
International Search Report for PCT/US14/71443, 3 pages (dated Mar. 19, 2015).
International Search Report for PCT/US2015/060685, 3 pages (dated Feb. 2, 2016).
International Search Report for PCT/US2017/024752, 8 pages (dated Aug. 29, 2017).

(56) References Cited

OTHER PUBLICATIONS

International Search Report for PCT/US2017/052528 (Devices and Methods for Cosmetic Skin Resurfacing, filed Sep. 20, 2017), issued by ISA/US, 5 pages (dated Jan. 4, 2018).
International Search Report for PCT/US2017/052539 (Rapid Skin Treatment Using Microcoring, filed Sep. 20, 2017), issued by ISA/US, 7 pages (dated Nov. 22, 2017).
International Searching Report and Written Opinion issued by the Korean Intellectual Property Office as International Search Authority for International Application No. PCT/US2011/035613 dated Jan. 12, 2012 (6 pages).
Lemperle, G. et al., A Classification of Facial Wrinkles, Plastic and Reconstructive Surgery, 108(6):1735-1750 (2001).
Moore, J. et al., Modeling of the Plane Needle Cutting Edge Rake and Inclination Angles for Biopsy, Journal of Manufacturing Science and Engineering, 132:051005-1-051005-8 (2010).
Narins, R. et al., Validated Assessment Scales for the Lower Face, Dermatology Surgery, 38:333-342 (2012).
PCT International Preliminary Report on Patentability, PCT/US2014/036638, dated Nov. 3, 2015, 7 pages.
PCT International Preliminary Report on Patentability, PCT/US2014/050426, dated Feb. 9, 2016, 8 pages.
PCT International Search Report and Written Opinion, PCT/US2014/036638, dated Oct. 2, 2014, 10 pages.
PCT International Search Report and Written Opinion, PCT/US2014/050426, dated Feb. 4, 2015, 18 pages.
Supplementary European Search Report issued by the European Patent Office for Application No. 11778450.4 dated Jan. 27, 2015 (5 pages).
Written Opinion for International Patent Application No. PCT/US2012/047708.
Written Opinion for PCT/US14/71443, 4 pages (dated Mar. 19, 2015).
Written Opinion for PCT/US2014/016483, 6 pages (dated May 6, 2014).
Written Opinion for PCT/US2015/060685, 4 pages (dated Feb. 2, 2016).
Written Opinion for PCT/US2017/024752, 11 pages (dated Aug. 29, 2017).
Written Opinion for PCT/US2017/052528 (Devices and Methods for Cosmetic Skin Resurfacing, filed Sep. 20, 2017), issued by ISA/US, 17 pages (dated Jan. 4, 2018).
Written Opinion for PCT/US2017/052539 (Rapid Skin Treatment Using Microcoring, filed Sep. 20, 2017), issued by ISA/US, 8 pages (dated Nov. 22, 2017).
Zhu, J. et al., The Efficacy and Safety of Fractional CO2 Laser Combined with Topical Type A Botulinum Toxin for Facial Rejuvenation: A Randomized Controlled Split-Face Study, BioMed Research International, 7 pages (2016).

\* cited by examiner

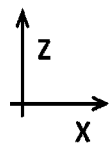
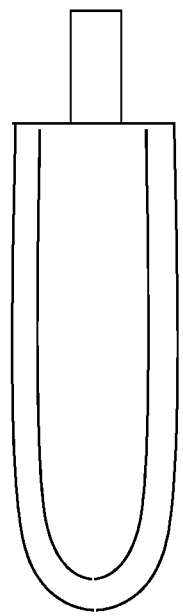
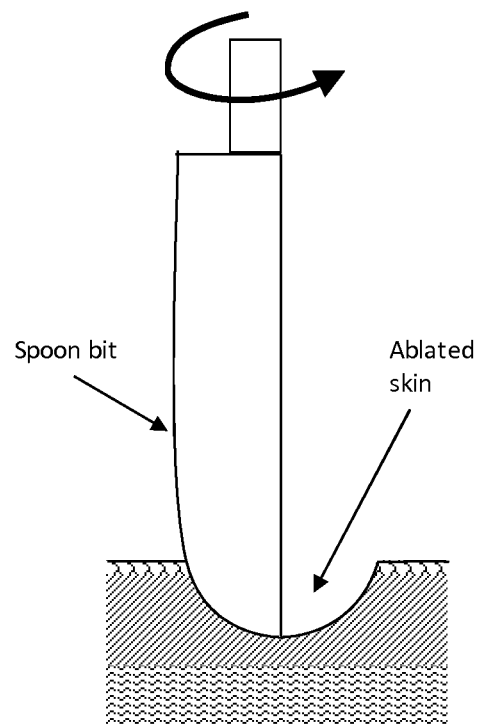
Front view
Lateral view
Spoon bit
Ablated skin
Figure 2A
Figure 2B

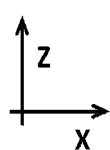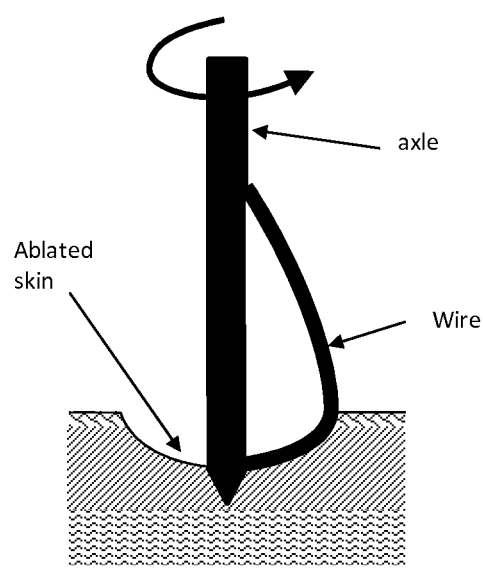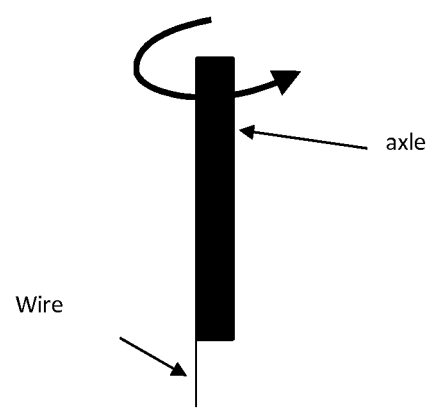
Figure 3A                                  Figure 3B

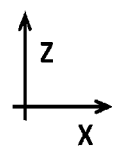
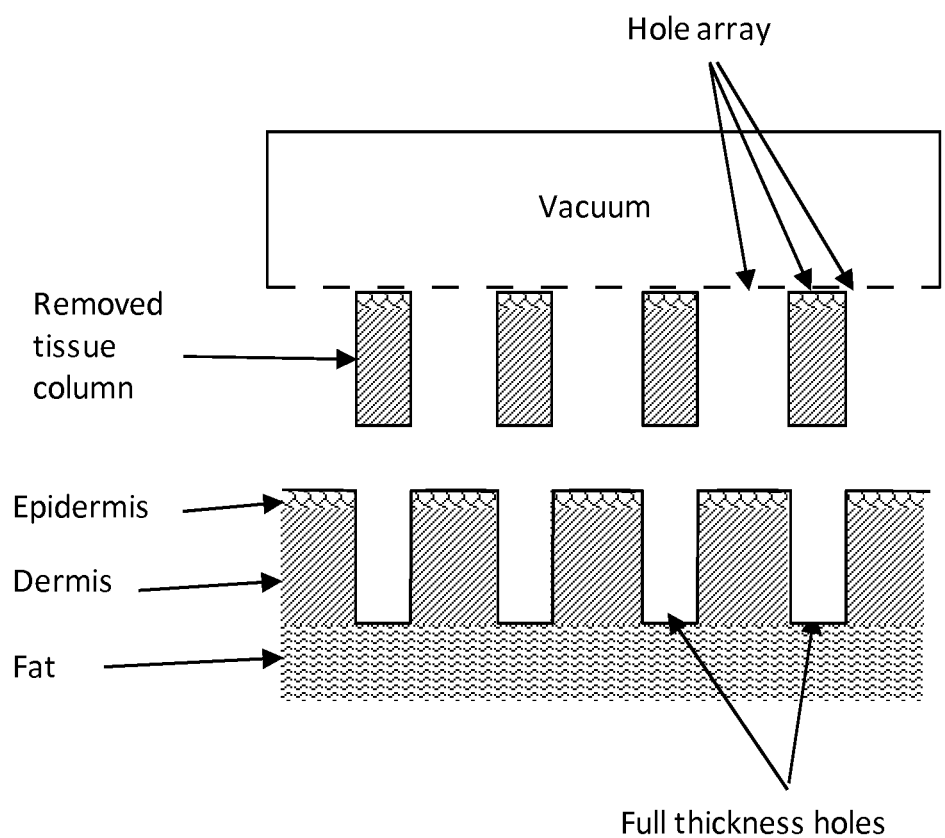
Figure 11

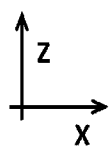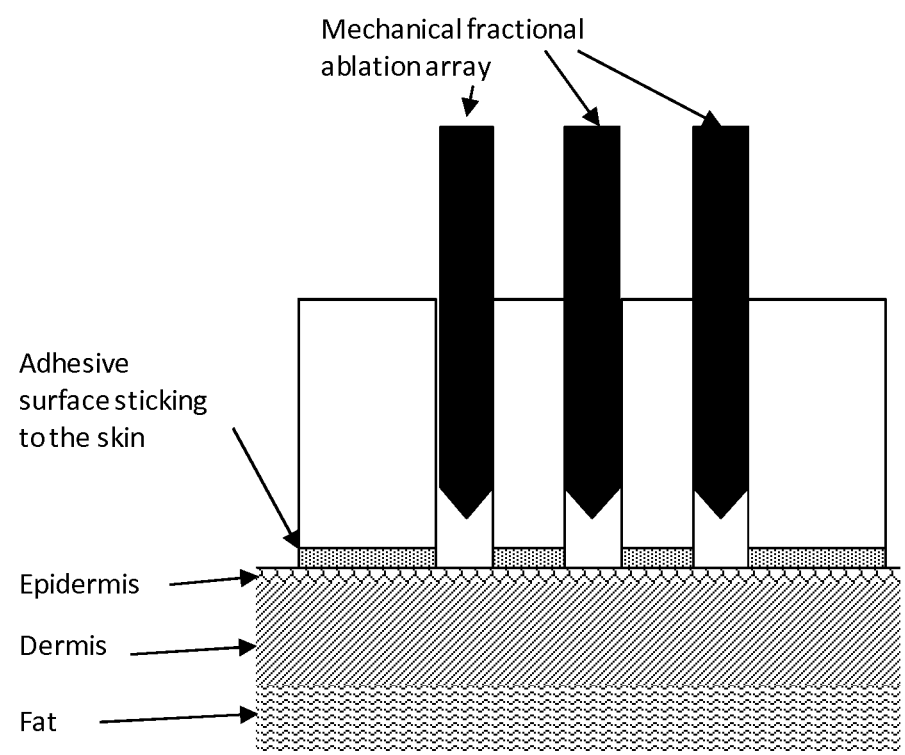
Figure 17

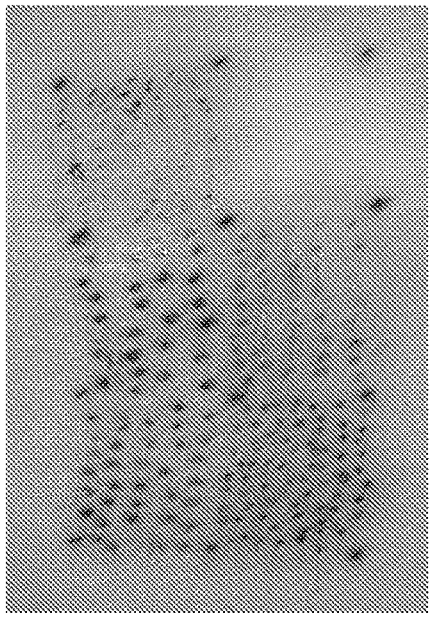
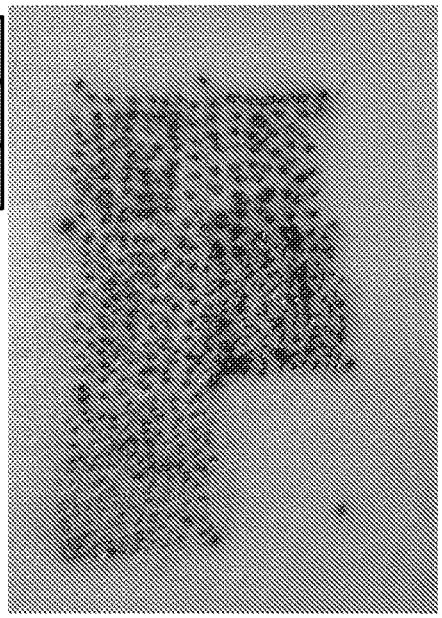
Figure 19

Subject R-A005, treatment with 21G needle, 10% coverage
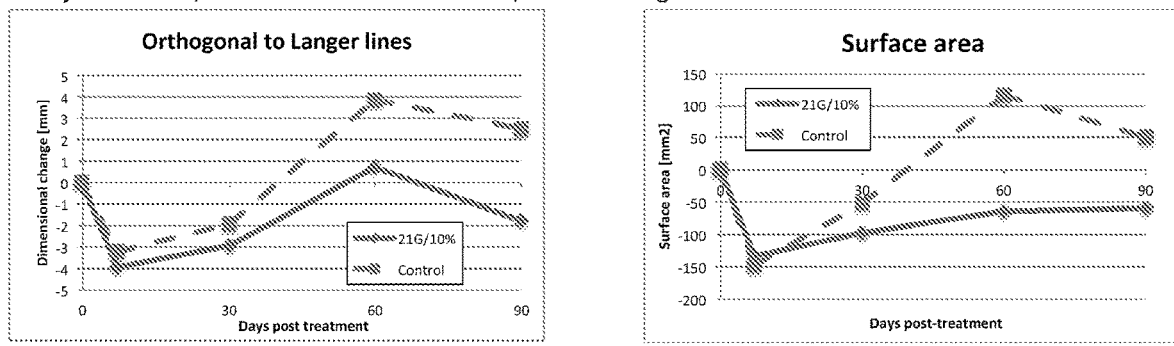
Subject R-A005, treatment with 22G needle, 10% coverage
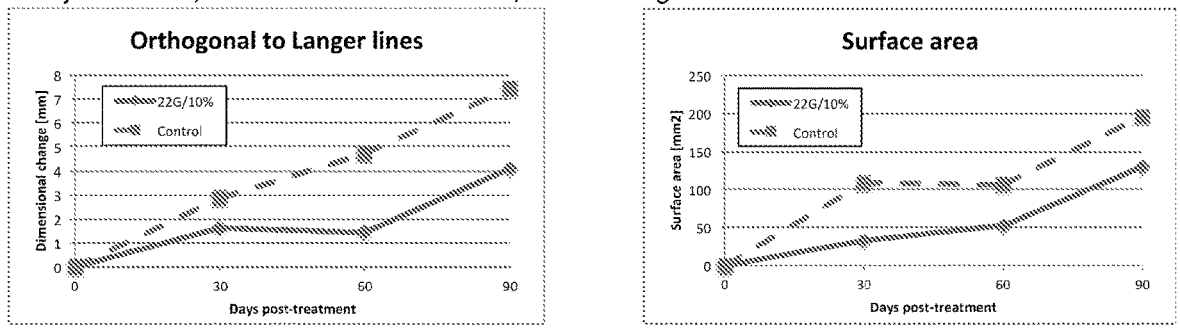
Figure 20

METHODS AND APPARATUSES FOR SKIN TREATMENT USING NON-THERMAL TISSUE ABLATION

BACKGROUND OF THE INVENTION

This invention relates to methods, apparatuses, and devices for treating skin and proximal tissue layers (e.g., such as fat, muscle, and facial SMAS (superficial muscular aponeurotic system)), such as skin tightening, or for treating diseases, disorders, and conditions that would benefit from tissue area or volume reduction, skin restoration, skin tightening, skin lifting, or skin repositioning, or tattoo removal.

Many human health issues arise from the damage or loss of tissue due to disease, advanced age, and/or injury. In aesthetic medicine, elimination of excess tissue and/or skin laxity is an important concern that affects more than 25% of the U.S. population. Conventional surgical therapies (e.g., a face lift, brow lift, or breast lift) can be effective but are often invasive, inconvenient, and expensive, while scarring limits the applicability of surgery to certain treatment sites.

Although minimally invasive methods are available, such methods are generally less effective than surgical methods. Methods using energy sources (e.g., laser, non-coherent light, radiofrequency, or ultrasound) can be effective at improving the architecture and the texture of the skin but are much less effective at tightening the skin or reducing skin laxity. Neurotoxins, such as botulinum toxin, reduce the formation of dynamic wrinkles by paralysis of the injected muscles, but such toxins have minimal or no direct effect on skin tightness or laxity. Finally, dermal fillers, such as hyaluronic acid, are injected in the dermal layer to smooth out wrinkles and improve contours, but such fillers do not directly tighten or reduce laxity of the skin. Thus, surgical therapies remain the gold standard for lifting and/or tightening skin, as compared to energy-based techniques (e.g., with laser, radiofrequency, or ultrasound ablation) and injection-based techniques (e.g., with botulinum toxin or hyaluronic acid- or collagen-based fillers).

Accordingly, there is a need for improved methods and devices that increase the effectiveness of minimally-invasive techniques while maintaining convenience, affordability, and/or accessibility to patients desiring tissue restoration.

SUMMARY OF THE INVENTION

This invention relates to methods and devices using non-thermal tissue ablation. The invention features an ablative apparatus for non-thermal tissue ablation including a skin-penetrating component configured to provide an ablated tissue portion having a width to depth ratio of between about 1:0.3 to about 1:75.

The invention also features a method of treating skin including: (a) positioning the skin using a compressive or a stretching force applied across said skin; (b) forming a plurality of ablated tissue portions; and (c) removing the plurality of ablated tissue portions, thereby treating the skin. In a preferred embodiment, the positioning is accomplished using a compressive force. In some embodiments, the ablated tissue portions have a width to depth ratio of between about 1:0.3 to about 1:75. The compressive force applied across the skin compresses the skin in a direction orthogonal to Langer lines. The plurality of ablated tissue portions is removed using needles with 21G. The plurality of ablated tissue portions being removed is about 10% of the skin within a treatment area.

The invention features a method of treating skin including: (a) forming a plurality of ablated tissue portions having a width to depth ratio of between about 1:0.3 to about 1:1 or of between about 1:25 to about 1:75; and (b) removing the plurality of ablated tissue portions, thereby treating said skin.

The invention features a method of treating skin including: (a) forming a plurality of ablated tissue portions having a change in width as a function of depth, where the change in width is of between about 10 μm to about 1000 μm (e.g., about 100 μm to about 500 μm or any ranges described herein) as a function of depth; and (b) removing the plurality of ablated tissue portions, thereby treating the skin.

The invention features a method of treating skin including: (a) forming a plurality of ablated tissue portions including a serrated or scalloped cross-sectional dimension (e.g., in the x-, y-, and/or z-axis); and (b) removing the plurality of ablated tissue portions, thereby treating the skin.

In any of the methods herein, step (b) includes pulling, squeezing, resorbing, desiccating, and/or liquefying the plurality of ablated tissue portions (e.g., using any method or apparatus described herein). In any of the methods herein, the method further includes (c) positioning the skin prior to step (a) and/or (b) (e.g., using any method or apparatus described herein) using a compressive force applied across said skin. In any of the methods herein, step (a) is performed with an ablative apparatus (e.g., any described herein) and/or step (b) is performed with a removal apparatus (e.g., any described herein) and/or step (c) is performed with a positioning apparatus (e.g., any described herein).

The invention features a positioning apparatus for positioning skin including a vacuum tube having at least one dimension of about 0.5 mm or more (e.g., at least about 1 mm) and a vacuum source, where the vacuum tube is configurably attached to the source and exerts a compressive force.

The invention features a positioning apparatus for positioning skin including a substrate having at least one dimension of about 0.5 mm or more (e.g., at least about 1 mm) and a cryosource, where the substrate is configurably attached to the cryosource and provides a cryotemperature of about 0 degrees C. or lower (e.g., where the operating temperature is between 0° C. to −180° C., such as about 0° C. to −20° C.).

The invention features a positioning apparatus for positioning skin including an adhesive layer having at least one dimension of about 0.5 mm or more (e.g., at least about 1 mm) and exerting a compressive force. In some embodiments, the adhesive layer may alternatively be used to hold the skin in an xy dimension or lift the skin in addition to compression.

The invention also features an ablative apparatus for non-thermal tissue ablation including a skin-penetrating component configured to provide an ablated tissue portion having a change in width as a function of depth, where the change in width is of between about 1 μm to about 1000 μm (e.g., about 100 μm to about 500 μm) as a function of depth.

The invention also features an ablative apparatus for non-thermal tissue ablation including a skin-penetrating component configured to provide an ablated tissue portion including a serrated or scalloped cross-sectional dimension.

The invention features an ablative apparatus for non-thermal tissue ablation including: (a) a skin-penetrating component including a drill bit including one or more spiral channels, a microauger including a spiral flange, a hollow drill bit, a tube including cutting teeth, and/or a spoon bit; and (b) a motor configured to rotate the component, where the motor is configurably attached to the component. In some embodiments, the component rotates from about 50 rpm to about 2500 rpm, such as ranges described herein.

The invention features an ablative apparatus for non-thermal tissue ablation including: (a) a skin-penetrating component including a wire and/or a fiber having a first attachment point and a second attachment point; (b) an axle having a sharpened distal end, a center portion, and a proximal end, where the first attachment point of the component is configurably attached to the distal end of the axle; and (c) a motor configured to rotate the component, where the motor is configurably attached to the proximal end of the axle. In some embodiments, the skin-penetrating component further includes a second attachment point and the second attachment point of the component is configurably attached to the center portion of the axle. In other embodiments, the component rotates from about 500 rpm to about 5000 rpm, such as any ranges described herein.

The invention features an ablative apparatus for non-thermal tissue ablation including a skin-penetrating component including a plurality of cylindrical blades or a plurality of straight blades assembled in a fractional pattern. In some embodiments, at least one of the plurality of cylindrical blades is configurably attached to an actuator for pushing the blade into the skin. In other embodiments, the actuator is a vibrating mechanism.

The invention features an ablative apparatus for non-thermal tissue ablation including (a) a skin-penetrating component including a high pressure fluid jet; (b) an in-flow tube configured to deliver one or more fluids to be emitted from the fluid jet; and (c) an optional out-flow tube configured to collect the one or more fluids after being emitted from the fluid jet. In some embodiments, the pressure of the high pressure fluid jet is from about 1000 psi to about 100000 psi, including other ranges described herein.

The invention features an ablative apparatus for non-thermal tissue ablation including (a) a skin-penetrating component including a plurality of cryoprobes and/or a plurality of cryoneedles; (b) a cryosource, where each cryoprobe and/or cryoneedle is configurably attached to the cryosource to provide cryotemperature treatment to skin; and (c) an optional insulator portion to shield regions of non-treated skin from exposure to the cryotemperature treatment, where the insulator portion is configurably attached to the component.

The invention features an ablative apparatus for non-thermal tissue ablation including (a) a skin-penetrating component including a plurality of needles, where each needle includes a plurality of holes configured to deliver one or more chemical or bioactive agents to skin; and (b) a depot including the one or more chemical or bioactive agents (e.g., any described herein), where each needle is configurably attached to the depot for delivering the one or more chemical or bioactive agents.

The invention features an ablative apparatus for non-thermal tissue ablation including (a) a skin-penetrating component including a plurality of microelectrodes, where each microelectrode includes an active electrode and a return electrode, or including a femtosecond laser (e.g., any described herein); (b) a generator configurably attached to each of the microelectrodes or laser; and (c) an optional electrical insulator portion to shield regions of non-treated skin from exposure to electrical and/or thermal energy, where the electrical insulator portion is configurably attached to the component. In some embodiments, the laser is an excimer laser (e.g., any described herein).

The invention features an ablative apparatus for non-thermal tissue ablation including (a) a skin-penetrating component including a plurality of needles, where each needle includes a plurality of holes configured to deliver vacuum to skin; and (b) a vacuum source, where each needle is configurably attached to the source. In some embodiments, the vacuum source includes an absolute pressure less than about 6.3 kPa (e.g., from about 0.1 kPa to about 6 kPa, such as from 0.1 kPa to 5 kPa, 0.1 kPa to 4 kPa, 0.1 kPa to 3 kPa, 0.1 kPa to 2 kPa, 0.1 kPa to 1 kPa, 0.5 kPa to 6 kPa, 0.5 kPa to 5 kPa, 0.5 kPa to 4 kPa, 0.5 kPa to 3 kPa, 0.5 kPa to 2 kPa, 0.5 kPa to 1 kPa, 1 kPa to 6 kPa, 1 kPa to 5 kPa, 1 kPa to 4 kPa, 1 kPa to 3 kPa, 1 kPa to 2 kPa, 1.5 kPa to 6 kPa, 1.5 kPa to 5 kPa, 1.5 kPa to 4 kPa, 1.5 kPa to 3 kPa, or 1.5 kPa to 2 kPa).

In any of the ablative apparatus herein, the apparatus is configured to provide from about 10 to about 10000 ablated tissue portions per $cm^2$ area of the skin region (e.g., including from about 100 to 10000 ablated tissue portions per $cm^2$ area of the skin region, as well as any other ranges described herein). In any of the ablative apparatus herein, the skin-penetrating component includes a drill, a microauger, a tube including cutting teeth, a spoon bit, a wire, a fiber, a blade, a high-pressure fluid jet, a cryoprobe, a cryoneedle, a multi-hole needle including one or more chemical or bioactive agents, a microelectrode, and/or a vacuum. In any of the ablative apparatus herein, the apparatus further includes one or more components selected from the group consisting of a motor, an axle, an adjustable depth stop, an in-flow tube, a return electrode, a generator, and an electrical insulator. In some embodiments, the ablative apparatus further includes a plurality of the skin-penetrating components in an array (e.g., in an pattern described herein).

In some embodiments, the ablative apparatus of the invention may be used to treat one or more diseases, disorders, or conditions in underlying skin layers, such as fat, muscle, and facial SMAS (superficial muscular aponeurotic system). In such embodiments, the ablative apparatus of the invention may include a skin-penetrating component configured to provide an ablated tissue portion having an appropriate depth (e.g., 2-10 mm) to reach the targeted underlying skin layers (e.g., fat, muscle, and facial SMAS).

In some embodiments, the ablative apparatus of the invention removes a plurality of ablated tissue portions using needles with 21G. The plurality of ablated tissue portions being removed is about 10% of the skin within a treatment area.

The invention also features a removal apparatus for removing one or more ablated tissue portion(s) including: (a) a substrate including a plurality of holes; and (b) a vacuum source, where the substrate is configurably attached to the source to deliver vacuum through each hole and to each of the one or more ablated tissue portion(s).

The invention features a removal apparatus for removing one or more ablated tissue portion(s) including an adhesive layer (e.g., any described herein) or an array of probes configured to contact each of the one or more ablated tissue portion(s).

The invention features a removal apparatus for removing one or more ablated tissue portion(s) including (a) a plurality of needles configured to contact each of the one or more ablated tissue portion(s); and (b) a heat source configured to deliver heat through the lumen of each needle and to each of the one or more ablated tissue portion(s). In some embodiments, the heat source is selected from a laser source, a hot needle, radiofrequency, ultrasound, a heated gas, or a heated liquid.

The invention features a removal apparatus for removing one or more ablated tissue portion(s) including (a) a wire having a first attachment point and a second attachment point; (b) an axle having a sharpened distal end, a center portion, and a proximal end, where the first attachment point of the wire is configurably attached to the distal end of the axle and the second attachment point of the wire is configurably attached to the center portion of the axle, and where the axle is configured to contact each of the one or more ablated tissue portion(s); (c) a motor configured to rotate the wire, where the motor is configurably attached to the proximal end of the axle; (d) a vacuum source, and (e) a substrate including a plurality of holes, where the substrate is configurably attached to a vacuum source to deliver vacuum through each hole and to each of the one or more ablated tissue portion(s).

In any of the distances provided for the removal and/or positioning apparatus, the minimum distance corresponds to the minimal size of the skin-penetrating component of the ablation apparatus. In other embodiments, the minimum distance corresponds to the minimal size of the array of a plurality of skin-penetrating components. Exemplary distances include more than about 0.5 mm or between about 0.2 mm to about 20 mm (e.g., from 0.2 mm to 1 mm, 0.2 mm to 2 mm, 0.2 mm to 5 mm, 0.2 mm to 10 mm, 0.2 mm to 15 mm, 0.5 mm to 1 mm, 0.5 mm to 2 mm, 0.5 mm to 5 mm, 0.5 mm to 10 mm, 0.5 mm to 15 mm, 0.5 mm to 20 mm, 0.75 mm to 1 mm, 0.75 mm to 2 mm, 0.75 mm to 5 mm, 0.75 mm to 10 mm, 0.75 mm to 15 mm, 0.75 mm to 20 mm, 1 mm to 1 mm, 1 mm to 2 mm, 1 mm to 5 mm, 1 mm to 10 mm, 1 mm to 15 mm, 1 mm to 20 mm, 1.5 mm to 1 mm, 1.5 mm to 2 mm, 1.5 mm to 5 mm, 1.5 mm to 10 mm, 1.5 mm to 15 mm, 1.5 mm to 20 mm, 2 mm to 1 mm, 2 mm to 2 mm, 2 mm to 5 mm, 2 mm to 10 mm, 2 mm to 15 mm, 2 mm to 20 mm, 2.5 mm to 1 mm, 2.5 mm to 2 mm, 2.5 mm to 5 mm, 2.5 mm to 10 mm, 2.5 mm to 15 mm, or 2.5 mm to 20 mm).

The invention also features a device including (a) an ablative apparatus for non-thermal tissue ablation of any described herein and (b) a removal apparatus for removing one or more ablated tissue portion(s) of any described herein, where the removal apparatus is configured to remove one or more ablated tissue portion(s) ablated with the ablative apparatus.

In some embodiments, the device includes an ablative apparatus including a drill and a removal apparatus including a vacuum, an ablative apparatus including a drill and a removal apparatus including an adhesive, an ablative apparatus including a drill (e.g., a hollow drill) and a removal apparatus including a laser, an ablative apparatus including a fiber and a removal apparatus including a vacuum, an ablative apparatus including a fiber and a removal apparatus including an adhesive, an ablative apparatus including one or more blades and a removal apparatus including a vacuum, an ablative apparatus including one or more blades and a removal apparatus including an adhesive, or an ablative apparatus including one or more blades and a removal apparatus including a laser, such as any described herein.

In some embodiments, the device further includes a positioning apparatus for positioning skin (e.g., any described herein), where the positioning apparatus is configured to position skin prior to ablation with the ablative apparatus and/or prior to removal with the removal apparatus. In other embodiments, the device further includes one or more sensors to detect position, temperature, skin proximity, microcontours, ablations, skin contact, and/or changes in inductive coupling.

The invention also features a kit including (a) an ablative apparatus for non-thermal tissue ablation (e.g., any described herein); (b) a removal apparatus for removing one or more ablated tissue portion(s) (e.g., any described herein); and optionally (c) a positioning apparatus for positioning skin (e.g., any described herein). In some embodiments, the removal apparatus includes a pin, an adhesive, a probe array, a vacuum, a compression element, a laser source, a high-pressure fluid jet, a cryoprobe, a cryosource, a cryoneedle, a multi-hole needle including one or more chemical or bioactive agents, a microelectrode, a wire, and/or a fiber (e.g., such as any described herein). In other embodiments, the positioning apparatus includes a tension rod, a microhook, a microbarb, vacuum, a cryoprobe, a cryosource, an adhesive, a switch, and/or a sensor.

In any of the devices or method herein, the ablative apparatus, the removal apparatus, and the positioning apparatus are configured in a single device.

The various embodiments of the present invention may be used to provide ablated tissue portions. An ablated tissue portion may have specific dimensions. In some embodiments, an ablated tissue portion has at least one dimension in a range of about 10 µm to about 2 mm (e.g., about 10 µm to 500 µm, about 10 µm to 100 µm, 10 µm to 250 µm, 10 µm to 500 µm, 10 µm to 750 µm, 10 µm to 1 mm, 10 µm to 1.5 mm, 10 µm to 2 mm, about 50 µm to 100 µm, 50 µm to 250 µm, 50 µm to 500 µm, 50 µm to 750 µm, 50 µm to 1 mm, 50 µm to 1.5 mm, 50 µm to 2 mm, 100 µm to 250 µm, 100 µm to 500 µm, 100 µm to 750 µm, 100 µm to 1 mm, 100 µm to 1.5 mm, 100 µm to 2 mm, 250 µm to 500 µm, 250 µm to 750 µm, 250 µm to 1 mm, 250 µm to 1.5 mm, 250 µm to 2 mm, 500 µm to 750 µm, 500 µm to 1 mm, 500 µm to 1.5 mm, 500 µm to 2 mm, 750 µm to 1 mm, 750 µm to 1.5 mm, or 750 µm to 2 mm). In some embodiments an ablated tissue portion has an areal dimension less than about 2 mm$^2$ and/or a volumetric dimension that is less than about 6 mm$^3$. The ablated tissue portion may have an areal dimension in a range of about 0.001 mm$^2$ to about 2 mm$^2$ (e.g., In some embodiments, ablated tissue portions have an areal dimension less than about 0.2 mm$^2$).

In some embodiments, an ablated tissue portion may form a hole in the skin region, where the diameter or width of the hole is less than about 1.0 mm (e.g., less than about 1.0 mm, 750 µm, 500 µm, 250 µm, 100 µm, 50 µm, or 10 µm). The ablated tissue portion may form a hole in the skin region, where the diameter or width is in a range of about 0.01 mm to about 2 mm (e.g., about 0.01 mm to 0.05 mm, 0.01 to 0.1 mm, 0.01 mm to 0.25 mm, 0.01 mm to 0.5 mm, 0.01 mm to 0.75 mm, 0.01 mm to 1 mm, 0.01 mm to 1.5 mm, 0.01 mm to 2 mm, 0.05 to 0.1 mm, 0.05 mm to 0.25 mm, 0.05 mm to 0.5 mm, 0.05 mm to 0.75 mm, 0.05 mm to 1 mm, 0.05 mm to 1.5 mm, 0.05 mm to 2 mm, 0.1 mm to 0.25 mm, 0.1 mm to 0.5 mm, 0.1 mm to 0.75 mm, 0.1 mm to 1 mm, 0.1 mm to 1.5 mm, 0.1 mm to 2 mm, 0.25 mm to 0.5 mm, 0.25 mm to 0.75 mm, 0.25 mm to 1 mm, 0.25 mm to 1.5 mm, 0.25 mm to 2 mm, 0.5 mm to 0.75 mm, 0.5 mm to 1 mm, 0.5 mm to 1.5 mm, 0.5 mm to 2 mm, 0.75 to 1 mm, 0.75 to 1.5 mm, or 0.75 to 2 mm, or any ranges described herein). In some embodiments, the volumetric dimension is less than or equal to about 6 mm$^3$ (e.g., as described herein) or between about 0.001 mm$^3$ and 6 mm$^3$ (e.g., as described herein). In particular embodiments, ablated tissue portions are discrete incised tissue or excised tissue portions.

The present invention includes ablated tissue portions having width to depth ratios between 1:0.3 to 1:1 (e.g., 1:0.3 to 1:1, 1:0.35 to 1:1, 1:0.4 to 1:1, 1:0.45 to 1:1, 1:0.5 to 1:1, 1:1 to 0.55 to 1:1, 1:0.6 to 1:1, 1:0.65 to 1:1, 1:0.7 to 1:1, 1:0.75 to 1:1, 1:0.8 to 1:1, 1:0.85 to 1:1, 1:0.9 to 1:1, 1:0.95 to 1:1, 1:0.3 to 1:0.95, 1:0.35 to 1:0.95, 1:0.4 to 1:0.95, 1:0.45 to 1:0.95, 1:0.5 to 1:0.95, 1:0.95 to 0.55 to 1:0.95, 1:0.6 to 1:0.95, 1:0.65 to 1:0.95, 1:0.7 to 1:0.95, 1:0.75 to 1:0.95, 1:0.8 to 1:0.95, 1:0.85 to 1:0.95, 1:0.9 to 1:0.95, 1:0.3 to 1:0.9, 1:0.35 to 1:0.9, 1:0.4 to 1:0.9, 1:0.45 to 1:0.9, 1:0.5 to 1:0.9, 1:0.9 to 0.55 to 1:0.9, 1:0.6 to 1:0.9, 1:0.65 to 1:0.9, 1:0.7 to 1:0.9, 1:0.75 to 1:0.9, 1:0.8 to 1:0.9, 1:0.85 to 1:0.9, 1:0.3 to 1:0.85, 1:0.35 to 1:0.85, 1:0.4 to 1:0.85, 1:0.45 to 1:0.85, 1:0.5 to 1:0.85, 1:0.85 to 0.55 to 1:0.85, 1:0.6 to 1:0.85, 1:0.65 to 1:0.85, 1:0.7 to 1:0.85, 1:0.75 to 1:0.85, 1:0.8 to 1:0.85, 1:0.3 to 1:0.8, 1:0.35 to 1:0.8, 1:0.4 to 1:0.8, 1:0.45 to 1:0.8, 1:0.5 to 1:0.8, 1:0.8 to 0.55 to 1:0.8, 1:0.6 to 1:0.8, 1:0.65 to 1:0.8, 1:0.7 to 1:0.8, 1:0.75 to 1:0.8, 1:0.3 to 1:0.75, 1:0.35 to 1:0.75, 1:0.4 to 1:0.75, 1:0.45 to 1:0.75, 1:0.5 to 1:0.75, 1:0.75 to 0.55 to 1:0.75, 1:0.6 to 1:0.75, 1:0.65 to 1:0.75, 1:0.7 to 1:0.75, 1:0.3 to 1:0.65, 1:0.35 to 1:0.65, 1:0.4 to 1:0.65, 1:0.45 to 1:0.65, 1:0.5 to 1:0.65, 1:0.65 to 0.55 to 1:0.65, 1:0.6 to 1:0.65, 1:0.3 to 1:0.65, 1:0.35 to 1:0.65, 1:0.4 to 1:0.65, 1:0.45 to 1:0.65, 1:0.5 to 1:0.65, 1:0.65 to 0.55 to 1:0.65, 1:0.6 to 1:0.65, 1:0.3 to 1:0.6, 1:0.35 to 1:0.6, 1:0.4 to 1:0.6, 1:0.45 to 1:0.6, 1:0.5 to 1:0.6, 1:0.6 to 0.55 to 1:0.6, 1:0.3 to 1:0.55, 1:0.35 to 1:0.55, 1:0.4 to 1:0.55, 1:0.45 to 1:0.55, 1:0.5 to 1:0.55, 1:0.3 to 1:0.5, 1:0.35 to 1:0.5, 1:0.4 to 1:0.5, 1:0.45 to 1:0.5, 1:0.5 to 1:0.5, 1:0.3 to 1:0.45, 1:0.35 to 1:0.45, 1:0.4 to 1:0.45, 1:0.3 to 1:0.4, 1:0.35 to 1:0.4, or 1:0.3 to 1:0.35) and 1:25 to 1:75 (e.g., 1:25 to 1:75, 1:30 to 1:75, 1:35 to 1:75, 1:40 to 1:75, 1:45 to 1:75, 1:50 to 1:75, 1:55 to 1:75, 1:60 to 1:75, 1:65 to 1:75, 1:70 to 1:75, 1:25 to 1:70, 1:30 to 1:70, 1:35 to 1:70, 1:40 to 1:70, 1:45 to 1:70, 1:50 to 1:70, 1:55 to 1:70, 1:60 to 1:70, 1:65 to 1:70, 1:25 to 1:65, 1:30 to 1:65, 1:35 to 1:65, 1:40 to 1:65, 1:45 to 1:65, 1:50 to 1:65, 1:55 to 1:65, 1:60 to 1:65, 1:25 to 1:60, 1:30 to 1:60, 1:35 to 1:60, 1:40 to 1:60, 1:45 to 1:60, 1:50 to 1:60, 1:55 to 1:60, 1:25 to 1:55, 1:30 to 1:55, 1:35 to 1:55, 1:40 to 1:55, 1:45 to 1:55, 1:50 to 1:55, 1:25 to 1:50, 1:30 to 1:50, 1:35 to 1:50, 1:40 to 1:50, 1:45 to 1:50, 1:25 to 1:45, 1:30 to 1:45, 1:35 to 1:45, 1:40 to 1:45, 1:25 to 1:40, 1:30 to 1:40, 1:35 to 1:40, 1:25 to 1:35, 1:30 to 1:35, or 1:25 to 1:30).

The invention may also feature ablated tissue portions having a width to depth ratios between about 1:1 to about 1:20 (e.g., 1:1 to 1:2, 1:1 to 1:3, 1:1 to 1:4, 1:1 to 1:5, 1:1 to 1:6, 1:1 to 1:7, 1:1 to 1:8, 1:1 to 1:9, 1:1 to 1:10, 1:1 to 1:11, 1:1 to 1:12, 1:1 to 1:13, 1:1 to 1:14, 1:1 to 1:15, 1:1 to 1:16, 1:1 to 1:17, 1:1 to 1:18, 1:1 to 1:19, 1:1 to 1:20, 1:2 to 1:3, 1:2 to 1:4, 1:2 to 1:5, 1:2 to 1:6, 1:2 to 1:7, 1:2 to 1:8, 1:2 to 1:9, 1:2 to 1:10, 1:2 to 1:11, 1:2 to 1:2, 1:2 to 1:13, 1:2 to 1:14, 1:2 to 1:15, 1:2 to 1:16, 1:2 to 1:17, 1:2 to 1:18, 1:2 to 1:19, 1:2 to 1:20, 1:3 to 1:4, 1:3 to 1:5, 1:3 to 1:6, 1:3 to 1:7, 1:3 to 1:8, 1:3 to 1:9, 1:3 to 1:10, 1:3 to 1:11, 1:3 to 1:12, 1:3 to 1:13, 1:3 to 1:14, 1:3 to 1:15, 1:3 to 1:16, 1:3 to 1:17, 1:3 to 1:18, 1:3 to 1:19, 1:3 to 1:20, 1:4 to 1:5, 1:4 to 1:6, 1:4 to 1:7, 1:4 to 1:8, 1:4 to 1:9, 1:4 to 1:10, 1:4 to 1:11, 1:4 to 1:12, 1:4 to 1:13, 1:4 to 1:14, 1:4 to 1:15, 1:4 to 1:16, 1:4 to 1:17, 1:4 to 1:18, 1:4 to 1:19, 1:4 to 1:20, 1:5 to 1:6, 1:5 to 1:7, 1:5 to 1:8, 1:5 to 1:9, 1:5 to 1:10, 1:5 to 1:11, 1:5 to 1:12, 1:5 to 1:13, 1:5 to 1:14, 1:5 to 1:15, 1:5 to 1:16, 1:5 to 1:17, 1:5 to 1:18, 1:5 to 1:19, 1:5 to 1:20, 1:6 to 1:7, 1:6 to 1:8, 1:6 to 1:9, 1:6 to 1:10, 1:6 to 1:11, 1:6 to 1:12, 1:6 to 1:13, 1:6 to 1:14, 1:6 to 1:15, 1:6 to 1:16, 1:6 to 1:17, 1:6 to 1:18, 1:6 to 1:19, 1:6 to 1:20, 1:7 to 1:8, 1:7 to 1:9, 1:7 to 1:10, 1:7 to 1:11, 1:7 to 1:12, 1:7 to 1:13, 1:7 to 1:14, 1:7 to 1:15, 1:7 to 1:16, 1:7 to 1:17, 1:7 to 1:18, 1:7 to 1:19, 1:7 to 1:20, 1:8 to 1:9, 1:8 to 1:10, 1:8 to 1:11, 1:8 to 1:12, 1:8 to 1:13, 1:8 to 1:14, 1:8 to 1:15, 1:8 to 1:16, 1:8 to 1:17, 1:8 to 1:18, 1:8 to 1:19, 1:8 to 1:20, 1:9 to 1:10, 1:9 to 1:11, 1:9 to 1:12, 1:9 to 1:13, 1:9 to 1:14, 1:9 to 1:15, 1:9 to 1:16, 1:9 to 1:17, 1:9 to 1:18, 1:9 to 1:19, 1:9 to 1:20, 1:10 to 1:11, 1:10 to 1:12, 1:10 to 1:13, 1:10 to 1:14, 1:10 to 1:15, 1:10 to 1:16, 1:10 to 1:17, 1:10 to 1:18, 1:10 to 1:19, 1:10 to 1:20, 1:11 to 1:12, 1:11 to 1:13, 1:11 to 1:14, 1:11 to 1:15, 1:11 to 1:16, 1:11 to 1:17, 1:11 to 1:18, 1:11 to 1:19, 1:11 to 1:20, 1:12 to 1:13, 1:12 to 1:14, 1:12 to 1:15, 1:12 to 1:16, 1:12 to 1:17, 1:12 to 1:18, 1:12 to 1:19, 1:12 to 1:20, 1:13 to 1:14, 1:13 to 1:15, 1:13 to 1:16, 1:13 to 1:17, 1:13 to 1:18, 1:13 to 1:19, 1:13 to 1:20, 1:14 to 1:15, 1:14 to 1:16, 1:14 to 1:17, 1:14 to 1:18, 1:14 to 1:19, 1:14 to 1:20, 1:15 to 1:16, 1:15 to 1:17, 1:15 to 1:18, 1:15 to 1:19, 1:15 to 1:20, 1:17 to 1:18, 1:17 to 1:19, or 1:17 to 1:20).

Exemplary ablated tissue portion widths include from about 0.1 mm to about 0.8 mm (e.g., 0.1 mm to 0.8 mm, 0.1 mm to 0.6 mm, 0.1 mm to 0.4 mm, 0.1 mm to 0.2 mm, 0.2 mm to 0.8 mm, 0.2 mm to 0.6 mm, 0.2 mm to 0.4 mm, 0.2 mm to 0.3 mm, 0.3 mm to 0.8 mm, 0.3 mm to 0.6 mm, 0.3 mm to 0.4 mm, 0.4 mm to 0.8 mm, 0.4 mm to 0.6 mm, 0.4 mm to 0.5 mm, 0.5 mm to 0.8 mm, 0.5 mm to 0.6 mm, 0.6 mm to 0.8 mm, 0.6 mm to 0.7 mm, or 0.7 mm to 0.8 mm). Exemplary ablated tissue portion widths include from about 0.9 mm to about 20 mm (e.g., 0.9 mm to 20 mm, 0.9 mm to 17 mm, 0.9 mm to 14 mm, 0.9 mm to 11 mm, 0.9 mm to 8 mm, 0.9 mm to 5 mm, 0.9 mm to 3 mm, 3 mm to 20 mm, 3 mm to 17 mm, 3 mm to 14 mm, 3 mm toll mm, 3 mm to 8 mm, 3 mm to 5 mm, 5 mm to 20 mm, 5 mm to 17 mm, 5 mm to 14 mm, 5 mm to 11 mm, 5 mm to 8 mm, 8 mm to 20 mm, 8 mm to 17 mm, 8 mm to 14 mm, 8 mm to 11 mm, 11 mm to 20 mm, 11 mm to 17 mm, 11 mm to 14 mm, 14 mm to 20 mm, 14 mm to 17 mm, or 17 mm to 20 mm) and 0.01 mm to 0.25 mm (e.g., 0.01 mm to 0.25 mm, 0.02 mm to 0.25 mm, 0.03 mm to 0.25 mm, 0.05 mm to 0.25 mm, 0.075 mm to 0.25 mm, 0.1 mm to 0.25 mm, 0.15 mm to 0.25 mm, 0.2 mm to 0.25 mm, 0.01 mm to 0.2 mm, 0.02 mm to 0.2 mm, 0.03 mm to 0.2 mm, 0.05 mm to 0.2 mm, 0.075 mm to 0.2 mm, 0.1 mm to 0.2 mm, 0.15 mm to 0.2 mm, 0.01 mm to 0.15 mm, 0.02 mm to 0.15 mm, 0.03 mm to 0.15 mm, 0.05 mm to 0.15 mm, 0.075 mm to 0.15 mm, 0.1 mm to 0.15 mm, 0.01 mm to 0.1 mm, 0.02 mm to 0.1 mm, 0.03 mm to 0.1 mm, 0.05 mm to 0.1 mm, 0.075 mm to 0.1 mm, 0.01 mm to 0.075 mm, 0.02 mm to 0.075 mm, 0.03 mm to 0.075 mm, 0.05 mm to 0.075 mm, 0.01 mm to 0.05 mm, 0.02 mm to 0.05 mm, 0.03 mm to 0.05 mm, 0.01 mm to 0.03 mm, 0.02 mm to 0.03 mm, 0.03 mm to 0.03 mm, 0.01 mm to 0.03 mm, 0.02 mm to 0.03 mm, or 0.01 mm to 0.02 mm). Further non-limiting exemplary ablated tissue portion widths and/or lengths include from about 0.01 mm to about 20 mm (e.g., 0.01 mm to 1 mm, 0.01 mm to 2 mm, 0.01 mm to 5 mm, 0.01 mm to 10 mm, 0.01 mm to 15 mm, 0.05 mm to 1 mm, 0.05 mm to 2 mm, 0.05 mm to 5 mm, 0.05 mm to 10 mm, 0.05 mm to 15 mm, 0.05 mm to 20 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.5 mm to 1 mm, 0.5 mm to 2 mm, 0.5 mm to 5 mm, 0.5 mm to 10 mm, 0.5 mm to 15 mm, 0.5 mm to 20 mm, 1 mm to 2 mm, 1 mm to 5 mm, 1 mm to 10 mm, 1 mm to 15 mm, 1 mm to 20 mm, 2 mm to 5 mm, 2 mm to 10 mm, 2 mm to 15 mm, 2 mm to 20 mm, 5 mm to 10 mm, 5 mm to 15 mm, or 5 mm to 20 mm) or from about 0.01 mm to about 2 mm (e.g., 0.01 mm to 0.1 mm, 0.01 mm to 0.5 mm, 0.01 mm to 1 mm, 0.01 mm to 1.5 mm, 0.01 mm to 1.75 mm, 0.05 mm to 0.1 mm, 0.05 mm to 0.5 mm, 0.05 mm to 1 mm, 0.05 mm to 1.5 mm, 0.05 mm to 1.75 mm, 0.05 mm to 2 mm, 0.1 mm to 0.5 mm, 0.1 mm to 1 mm, 0.1 mm to 1.5 mm, 0.1 mm to 1.75 mm, 0.1 mm to 2 mm, 0.3 mm to 0.5 mm, 0.3 mm to 1 mm, 0.3 mm to 1.5 mm, 0.3 mm to 1.75 mm, 0.3 mm to 2 mm, 0.5 mm to 1 mm, 0.5 mm to 1.5 mm, 0.5 mm to 1.75 mm, 0.5 mm to 2 mm, 0.7 mm to 1 mm, 0.7 mm to 1.5 mm, 0.7 mm to 1.75 mm, 0.7 mm to 2 mm, 1 mm to 1.5 mm, 1 mm to 1.75 mm, 1 mm to 2 mm, 1.5 mm to 1.75 mm, 1.5 mm to 2 mm, or 1.75 mm to 2 mm).

In any embodiment described herein, the devices, apparatuses, and/or methods include the use of one or more therapeutic agents selected from growth factors, analgesics (e.g., an NSAID, a COX-2 inhibitor, an opioid, a glucocorticoid agent, a steroid, or a mineralocorticoid agent, or any described herein), anesthetics (e.g., procaine, amethocaine, cocaine, lidocaine (also known as Lignocaine), prilocaine, bupivacaine, levobupivacaine, ropivacaine, mepivacaine, benzocaine, butamben, dibucaine, oxybuprocaine, pramoxine, proparacaine, proxymetacaine, tetracaine, or dibucaine), antibiotics, antifungals, antiinflammatory agents, antimicrobials (e.g., chlorhexidine-, iodine-, or silver-based agents, as described herein), antiseptics (e.g., an alcohol, a quaternary ammonium compound, or any described herein), antiproliferative agents, emollients, hemostatic agents, procoagulative agents, anticoagulative agents, immune modulators, proteins, vitamins, microparticles (e.g., carbon particles), nanoparticles (e.g., gold nanocomposites), imaging agents (e.g., a radioisotope-containing moiety or a fluorescent-containing moiety), dyes (e.g., an ink, a chromophore, a visible dye, an IR dye, or a fluorescent dye), pigments, tracers, skin whitening agents (e.g. hydroquinone), vitamin A derivatives (e.g., tretinoin), or cosmetics (e.g., a cream, a lotion, an emollient, a powder, a perfume, a lipstick, a makeup, a towelette, a hand sanitizer, a butter, and others). In particular embodiments, the therapeutic agent is a hemostatic agent (e.g., a vasoconstrictor, such as epinephrine, pseudoephedrine, cocaine, an amphetamine, an antihistamine, a decongestant, or a stimulant), a procoagulative agent, an anticoagulative agent, or combinations thereof. In some embodiments, the therapeutic agent is selected from the group of anhydrous aluminum sulfate, anti-fibrinolytic agent(s) (e.g., epsilon aminocaproic acid, tranexamic acid, or the like), anti-platelet agent(s) (e.g., aspirin, dipyridamole, ticlopidine, clopidogrel, or prasugrel), calcium alginate, cellulose, chitosan, coagulation factor(s) (e.g., II, V, VII, VIII, IX, X, XI, XIII, or Von Willebrand factor, as well as activated forms thereof), collagen (e.g., microfibrillar collagen), coumarin derivative(s) or vitamin K antagonist(s) (e.g., warfarin (coumadin), acenocoumarol, atromentin, phenindione, or phenprocoumon), desmopressin, epinephrine, factor Xa inhibitor(s) (e.g., apixaban or rivaroxaban), fibrinogen, heparin or derivatives thereof (e.g., low molecular weight heparin, fondaparinux, or idraparinux), poly-N-acetyl glucosamine, potassium alum, propyl gallate, silver nitrate, thrombin, thrombin inhibitor(s) (e.g., argatroban, bivalirudin, dabigatran, hirudin, lepirudin, or ximelagatran), titanium oxide, or a zeolite (e.g., a calcium-loaded zeolite).

In any embodiment described herein, the devices, apparatuses, and methods are useful for eliminating tissue volume or area, promoting beneficial tissue growth, tightening skin, rejuvenating skin, improving skin texture or appearance, removing skin laxity, lifting skin, skin repositioning, tattoo removal, and/or expanding tissue volume or area. In some embodiments, the devices, apparatuses, and methods are useful for treating one or more diseases, disorders, or conditions to improve skin appearance, to rejuvenate skin, and/or to tighten skin. Exemplary diseases, disorders, or conditions are described herein and include removal of pigment, veins (e.g., spider veins or reticular veins), and/or vessels in the skin, as well as treatment of acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., crow's feet, age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), vascular lesions (e.g., angioma, erythema, hemangioma, papule, port wine stain, rosacea, reticular vein, or telangiectasia), or any other unwanted skin irregularities (e.g., areas of fibrosis and/or necrosis).

In other embodiments, the devices, apparatuses, and methods described herein allow for treatment of uneven surfaces (e.g., the face). In particular, large area ablation techniques can be difficult to apply in a conformal or uniform manner to uneven skin surfaces. Thus, the present invention allows for conforming to the skin surface, even if the surface is uneven.

In other embodiments, the devices, apparatuses, and methods described herein allow for immediate assessment of the expected or approximate outcome of the treatment. Compared to energy-based methods, the expected or approximate outcome of the treatment can be immediately visible. For instance, treatment with conventional energy-based devices activates remodeling of the tissue and the end-result is only visible weeks to months after treatment.

In other embodiments, the devices, apparatuses, and methods described herein allow for rapid healing. For instance, compared to surgery, the treatment can be much less invasive and the healing can be, therefore, much faster.

The invention also features a method of treating skin including (a) forming a plurality of ablated tissue portions using a 21G needle; and (b) removing the plurality of ablated tissue portions, wherein 10% of the skin within a treatment area is removed. In some embodiments, the plurality of ablated tissue portions are removed with a multiple needle array. In some embodiments, the treating results in a reduction of skin surface area. In particular, the reduction in skin surface area occurs in a direction orthogonal to Langer lines.

Definitions

By "ablated tissue portion" is meant that portion of a skin region that is cut, abraded, damaged, or removed. This term can also mean the skin region or plug that has been cut or removed. An ablated tissue portion includes holes in the tissue, for example, having a particular geometry (e.g., a cylindrical geometry), cross-sectional dimension, or width to depth ratio. An ablated tissue portion may also include a microwound, an incised tissue portion, or excised tissue portion. An ablated tissue portion may further be the removed tissue portion resulting from the formation of a hole. An ablated tissue portion may further be the damaged tissue portion resulting from the formation of a hole by using, e.g., a microwire homogenizer.

By "ablation apparatus" is meant an entity capable of ablating tissue. In particular, the entity may be or include a mechanical mechanism, such as a needle, drill bit, blade, auger, punch, die, or other entity capable of ablation of tissue. The entity may be an energy ablation mechanism, such as an electrode, a laser, an RF energy generator, or heating coil. The entity may be a chemical or bioactive agent, mass (e.g., a fluid jet), or a vacuum. The entity may be a component in an array or a device.

By "about" is meant +/−10% of any recited value.

By "areal dimension" is meant the two-dimensional area of an entity. The area of the opening of an ablated tissue portion may be an areal dimension. For example, a circular ablated tissue portion with a diameter of 0.5 mm would have an areal dimension of about 0.2 mm². If a compressive force is applied to skin surrounding the ablated tissue portion, then the opening may be closed, thus reducing the ablated tissue portion areal dimension to substantially zero, even though the underlying ablated tissue portion below the surface of the skin still exists.

By "non-thermal ablation" is meant an ablation technique that does not transfer thermal energy to the surrounding tissue. Mechanical processes can generate heat but in insufficient amounts to contribute meaningfully to the desired effect. In one non-limiting embodiment, non-thermal ablation includes use of a laser that does not create a coagulation zone.

By "non-thermal ablation apparatus" is meant an entity capable of non-thermal ablation.

By "prophylactically treating" a disease, disorder, or condition in a subject is meant reducing the frequency of occurrence or severity of (e.g., preventing) a disease, disorder or condition by affixing a device (e.g., a closure) to the subject prior to the appearance of a symptom of the disease, disorder, or condition.

By "serrated cross-sectional dimension" is meant a cross-section of a geometric shape in which the borders visible in the cross-section are irregular and/or undulating.

By "skin-penetrating component" is meant a component that is capable of puncturing the skin. Exemplary skin-penetrating components are needles, punches, drill bits, and probes.

By "subject" is meant a human or non-human animal (e.g., a mammal).

By "treating" a disease, disorder, or condition in a subject is meant reducing at least one symptom of the disease, disorder, or condition.

Other features and advantages of the invention will be apparent from the following Detailed Description and the claims.

BRIEF DESCRIPTION OF THE DRAWINGS

FIGS. 2A and 2B show an exemplary ablation drill bit (a spoon bit). FIG. 2A is a front view of the drill bit having a u-shaped cutting edge. FIG. 2B is a side view of the drill bit having a hemispherical shape with flat surface (front) providing dual cutting edges that may be rotated around the drill bit axis.

FIGS. 3A and 3B show exemplary wire or fiber ablation apparatuses. FIG. 3A depicts a curved wire attached to the bottom and top ends of a needle. The needle provides an axis of rotation, allowing the wire to be rotated, thus causing the wire to remove a volume of tissue. The shape of the wire defines the geometry and dimensions of the tissue ablation. FIG. 3B depicts a straight wire attached to axle or needle. The straight wire is attached to the axle at only one end, allowing the wire an additional degree of freedom during rotation (e.g., moving perpendicular to the longitudinal axis of the axle).

FIG. 5A is a schematic of a high pressure fluid ablation apparatus projecting fluid jets onto the exterior surface of the tissue, thus forming a series of ablated tissue portions. FIG. 5B is a schematic of a high-pressure fluid ablation apparatus inserted under the tissue and projecting fluid jets to the interior of the tissue, thus forming a series of ablated tissue portions.

FIG. 6A depicts an array of cryoprobes, each of which may ablate tissue at the interface between the probe and the tissue. FIG. 6B depicts an array of cryoneedles, each of which may ablate tissue with cold temperature upon contact.

FIG. 7 depicts the chemical or bioactive ablation apparatus having a multi-hole needle, in which holes along the cylindrical body of the needle allow for transfer of a chemical or bioactive agent at a controlled depth or location.

FIG. 10A depicts a flat adhesive layer covering the support layer and removal of tissue by adhesion of the tissue to the adhesive layer. FIG. 10B depicts adhesive layers affixed to the ends of probes attached to the support layer. FIG. 10B also depicts the removal of tissue by adhesion of the tissue to the adhesive layer on the end of the probe.

FIG. 11 shows an exemplary tissue removal array apparatus having a housing which can sustain a vacuum and an array of holes. FIG. 11 depicts the removal of tissue by adherence of tissue by a partial or complete vacuum seal to a hole of the array.

FIG. 12 depicts an exemplary method of tissue removal in which the blade ablation device isolates the tissue to be ablated from the surrounding tissue. Once the tissue is isolated, a thermal ablation device can ablate the tissue inside the blade ablation device, thus removing the tissue. The blade ablation device insulates the surrounding tissue from the thermal ablation, thus preventing coagulation of the surrounding tissue.

FIG. 17 shows an exemplary tissue positioning apparatus having a housing including an adhesive layer on one surface and providing access through the housing for an ablation apparatus or array of ablation apparatuses. A tissue layer under tension may adhere to the adhesive layer, thus positioning and providing tension to the tissue layer.

FIG. 19 shows photographs of areas of the abdomen of human subjects treated with different needle sizes immediately after treatment.

FIG. 20 shows several graphs indicating the change in linear dimension/surface area of a treated square area (21G/10% or 22G/10%) in comparison with a contra-lateral non-treated area of similar dimension (control).

DETAILED DESCRIPTION

Figure 1:
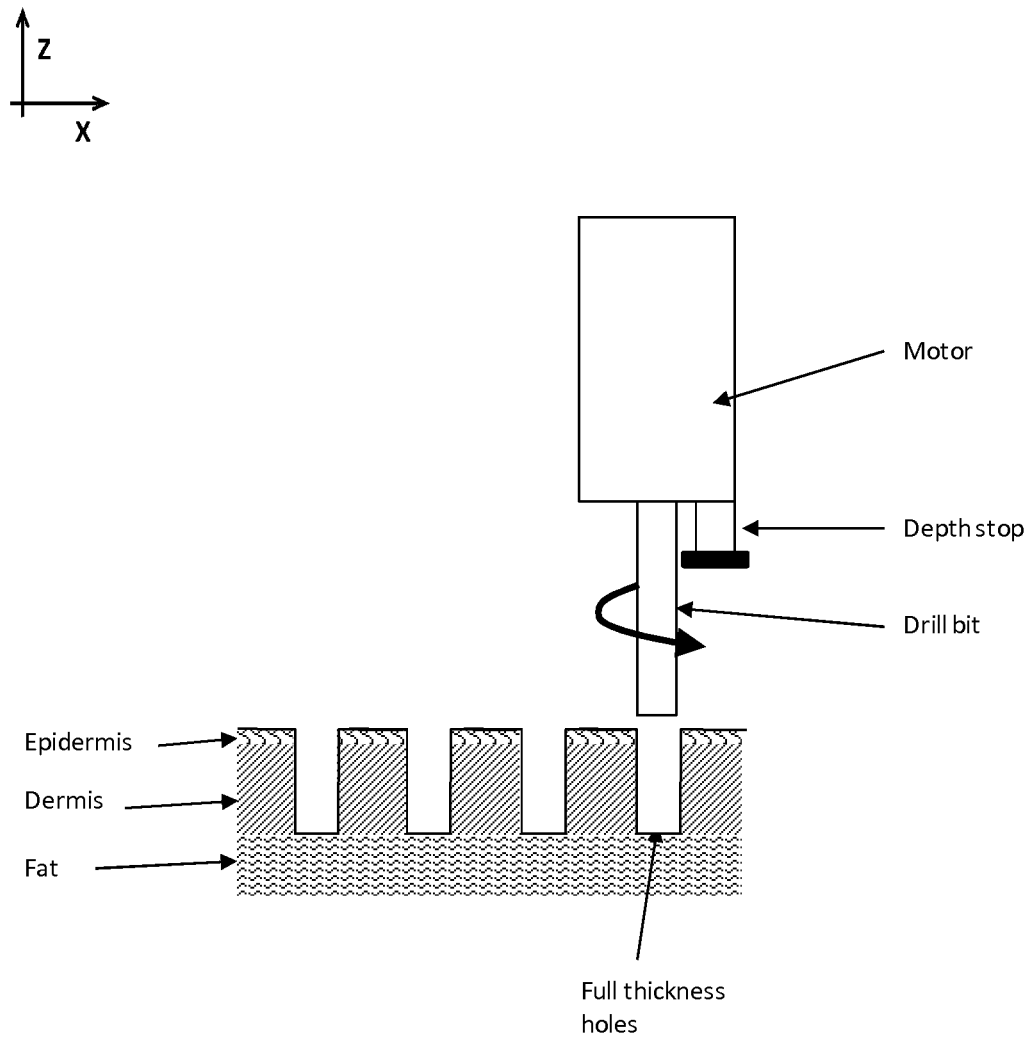
FIG. 1 shows an exemplary ablation apparatus having a motor, a depth stop, and a rotating drill bit. Also described in FIG. 1 is the formation of full thickness holes (ablation spanning the complete epidermis and dermis layers) using the ablation apparatus.

This invention relates to methods and devices for treating skin (e.g., eliminating tissue volume, tightening skin, lifting skin, and/or reducing skin laxity) by selectively opening or closing a plurality of wounds or holes (e.g., ablated tissue portions) formed by ablation (e.g., incision or excision of tissue) without thermal energy being imparted to the surrounding (e.g., non-ablated) tissue. For example, non-thermal ablation can be performed by fractional ablation of the epidermal and/or dermal layer of the skin using a mechanical method, such as a hollow coring needle, a drill, a microauger, a tube comprising cutting teeth, a spoon bit, a wire, or a fiber, by a fractional ablation using a high-pressure fluid jet, by fractional cryosurgery using a cryoprobe or cryoneedle, by a fractional chemical ablation, by fractional electroporation, by a femtosecond laser, and/or by fractional vacuum ablation. The methods and apparatuses of the invention also include skin removal methods. Thermal ablation methods may be used, such as fractional laser ablation or fractional radio-frequency (RF) ablation, to remove portions of a skin region to be ablated once the region is thermally isolated from the surrounding tissue, thereby not transferring thermal energy to the surrounding tissue. The present invention also features tissue positioning methods and apparatuses. The present invention may include methods and devices for non-thermal ablation, tissue removal, tissue positioning, and combinations thereof.

In particular embodiments, the present invention provides one or more of the following advantages. First, the methods and devices herein enable visualization of results in real time during the course of the treatment. One can envision asking the patient for feedback in real time during the treatment and adjusting the tightening to the patient preference. Second, the apparatuses include micro-sized features, which can be beneficial for controlling the extent of skin treatment. Third, the methods and apparatuses described herein may require less skill than that of a surgeon. One can envision treatment of patients in an outpatient setting, rather than requiring an inpatient, surgical setting. Fourth, the methods and apparatuses herein constitute minimally invasive techniques, which can provide more predictable results and/or risk factors than that for more invasive techniques (e.g., plastic surgery) or non-invasive energy-based techniques (e.g., laser, radiofrequency (RF), or ultrasound). Fifth, the non-thermal fractional ablation methods and apparatuses herein allow skin tightening, skin lifting, and reduction of skin laxity without inducing coagulation in the surrounding tissue. Thermal ablation techniques prevent and/or inhibit skin tightening by allowing coagulation of the tissue and formation of rigid tissue cores that cannot be compressed. Sixth, the methods and apparatuses herein can allow for rapid closing of holes or slits after treating the skin (e.g., within a few seconds after treating skin, such as within ten seconds), thereby minimizing the extent of bleeding and/or clotting within the holes or slits and/or scar formation. Seventh, the methods and apparatuses herein can be useful for maximizing the tightening effect while minimizing healing time by optimizing tightening (e.g., by controlling the extent of skin pleating, such as by increasing the extent of skin pleating for some applications or skin regions and by decreasing the extent of skin pleating for other applications or skin regions, as described herein). Eighth, the methods and apparatuses for tissue removal described herein provide efficient clearance of partially ablated tissue and debris from ablated tissue portions, thus reducing the time for healing and improving the skin tightening treatment. Finally, the methods and apparatuses for skin positioning described herein allow for efficient and effective positioning of skin prior to, during, and after ablation and/or tissue removal. Positioning the skin is critical to control skin-tightening direction and ensure ablation occurs in the desired location and desired dimensions.

In some embodiments, apparatuses and methods of the invention allow for the treatment of skin with varied thickness. Skin regions vary in thickness depending on the location on the body. For example, Kakasheva-Mazenkovska et al., (Contributions, Soc. Biol. Med. Sci., MASA, XXXII, 2, p. 119-128 (2011), incorporated by reference herein in its entirety) describes thin skin regions for 23-53 year old adults as including the anterior lower leg (average skin thickness of 1.7 mm) and the cheeks (average skin thickness of 2.1 mm) and thick skin regions as the anterior leg (average skin thickness of 4.9 mm, e.g., in the anterior upper leg) and the gluteus (average skin thickness of 5.2 mm). The thinnest skin region observed across all age groups studied was about 0.9 mm, while the thickest skin region observed across all age groups was about 5.9 mm. To allow for effective skin tightening, ablative tissue portions with a diameter of between 100 µm and 800 µm (e.g., 100, 200, 300, 400, 500, 600, 700, 800 µm) may be desirable. In some embodiments, ablative tissue portions with a diameter of between 200 µm and 700 µm may be desirable. In some embodiments, ablative tissue portions with a diameter of between 300 µm and 500 µm may be desirable. In other embodiments, ablative tissue portions with a diameter of between 500 µm and 800 µm may be desirable. Maintaining the desired diameter may require the ablation apparatus to provide width to depth ratios across a large range (e.g., from 1:0.3 to 1:75).

Ablated Tissue Portions

The present invention features methods, apparatuses and devices for generating ablated tissue portions having various geometric dimensions. For instance, the tissue portions can have a width to depth ratio of between about 1:0.3 to about 1:75. In another non-limiting example, the tissue portions have a change in width as a function of depth (e.g., a change in width of between about 10 µm to about 1000 µm as a function of depth, e.g., 10 µm to 50 µm, 10 µm to 100 µm, 10 µm to 250 µm, 10 µm to 500 µm, 10 µm to 750 µm, 25 µm to 50 µm, 25 µm to 100 µm, 25 µm to 250 µm, 25 µm to 500 µm, 25 µm to 750 µm, 25 µm to 1000 µm, 50 µm to 100 µm, 50 µm to 250 µm, 50 µm to 500 µm, 50 µm to 750 µm, 50 µm to 1000 µm, 75 µm to 100 µm, 75 µm to 150 µm, 75 µm to 200 µm, 75 µm to 250 µm, 75 µm to 300 µm, 75 µm to 350 µm, 75 µm to 400 µm, 75 µm to 450 µm, 75 µm to 500 µm, 75 µm to 600 µm, 75 µm to 750 µm, 75 µm to 900 µm, 75 µm to 1000 µm, 100 µm to 200 µm, 100 µm to 250 µm, 100 µm to 300 µm, 100 µm to 350 µm, 100 µm to 400 µm, 100 µm to 450 µm, 100 µm to 500 µm, 100 µm to 750 µm, 100 µm to 900 µm, 100 µm to 1000 µm, 150 µm to 250 µm, 150 µm to 500 µm, 150 µm to 750 µm, 150 µm to 1000 µm, 200 µm to 250 µm, 200 µm to 500 µm, 200 µm to 750 µm, 200 µm to 1000 µm, 250 µm to 500 µm, 250 µm to 750 µm, 250 µm to 1000 µm, 400 µm to 500 µm, 400 µm to 750 µm, 400 µm to 1000 µm, 500 µm to 750 µm, 500 µm to 1000 µm, or 750 µm to 1000 µm).

In yet other embodiments, the tissue portions can include a serrated cross-sectional dimension. In some embodiments the ablated tissue portions of the invention have at least one dimension between about 10 µm and about 2 mm. In other embodiments, an ablated tissue portion has an areal dimension of less than about 2.0 mm$^2$. In additional embodiments, an ablated tissue portion has a volume of less than about 6.0 mm$^3$. These embodiments are further described below.

An ablated tissue portion may have specific dimensions. In some embodiments, an ablated tissue portion has at least one dimension in a range of about 10 µm to about 2 mm (e.g., about 10 µm to 500 µm, about 10 µm to 100 µm, 10 µm to 250 µm, 10 µm to 500 µm, 10 µm to 750 µm, 10 µm to 1 mm, 10 µm to 1.5 mm, 10 µm to 2 mm, about 50 µm to 100 µm, 50 µm to 250 µm, 50 µm to 500 µm, 50 µm to 750 µm, 50 µm to 1 mm, 50 µm to 1.5 mm, 50 µm to 2 mm, 100 µm to 250 µm, 100 µm to 500 µm, 100 µm to 750 µm, 100 µm to 1 mm, 100 µm to 1.5 mm, 100 µm to 2 mm, 250 µm to 500 µm, 250 µm to 750 µm, 250 µm to 1 mm, 250 µm to 1.5 mm, 250 µm to 2 mm, 500 µm to 750 µm, 500 µm to 1 mm, 500 µm to 1.5 mm, 500 µm to 2 mm, 750 µm to 1 mm, 750 µm to 1.5 mm, or 750 µm to 2 mm). In some embodiments an ablated tissue portion has an areal dimension less than about 2 mm$^2$ and/or a volumetric dimension that is less than about 6 mm$^3$. The ablated tissue portion may have an areal dimension in a range of about 0.001 mm$^2$ to about 2 mm$^2$. In some embodiments, ablated tissue portions have an areal dimension less than about 0.2 mm$^2$.

In some embodiments, an ablated tissue portion may form a hole in the skin region, where the diameter or width of the hole is less than about 1.0 mm (e.g., less than about 1.0 mm, 750 µm, 500 µm, 250 µm, 100 µm, 50 µm, or 10 µm). The ablated tissue portion may form a hole in the skin region, where the diameter or width is in a range of about 0.01 mm to about 2 mm (e.g., about 0.01 mm to 0.05 mm, 0.01 to 0.1 mm, 0.01 mm to 0.25 mm, 0.01 mm to 0.5 mm, 0.01 mm to 0.75 mm, 0.01 mm to 1 mm, 0.01 mm to 1.5 mm, 0.01 mm to 2 mm, 0.05 mm to 0.1 mm, 0.05 mm to 0.25 mm, 0.05 mm to 0.5 mm, 0.05 mm to 0.75 mm, 0.05 mm to 1 mm, 0.05 mm to 1.5 mm, 0.05 mm to 2 mm, 0.1 mm to 0.25 mm, 0.1 mm to 0.5 mm, 0.1 mm to 0.75 mm, 0.1 mm to 1 mm, 0.1 mm to 1.5 mm, 0.1 mm to 2 mm, 0.25 mm to 0.5 mm, 0.25 mm to 0.75 mm, 0.25 mm to 1 mm, 0.25 mm to 1.5 mm, 0.25 mm to 2 mm, 0.5 mm to 0.75 mm, 0.5 mm to 1 mm, 0.5 mm to 1.5 mm, 0.5 mm to 2 mm, 0.75 to 1 mm, 0.75 to 1.5 mm, or 0.75 to 2 mm, or any ranges described herein). In some embodiments, the volumetric dimension that is less than or equal to about 6 mm$^3$ (e.g., as described herein) or between about 0.001 mm$^3$ and 6 mm$^3$ (e.g., as described herein). In particular embodiments, ablated tissue portions are discrete incised tissue or excised tissue portions.

The ablated tissue portion can have any combination of the dimensions described herein. For instance, in some non-limiting embodiments, the ablated tissue portion has at least one dimension that is less than about 2 mm and an areal dimension that is less than about 2 mm$^2$. In other embodiments, the ablated tissue portion has at least one dimension that is less than about 2 mm and a volumetric dimension that is less than about 6 mm$^3$. In yet other embodiments, the ablated tissue portion has at least one dimension that is less than about 2 mm and an areal dimension that is less than about 2 mm$^2$ and a volumetric dimension that is less than about 6 mm$^3$. In some embodiments, the ablated tissue portion has an areal dimension that is less than about 2 mm$^2$ and a volumetric dimension that is less than about 6 mm$^3$.

Width-to-Depth Ratio

The present invention allows for tissue portions having particular width-to-depth ratios. Benefits for optimizing such ratios include improved skin tightening, treatment of thin skin regions (e.g., lower anterior leg and cheeks), treatment of thick skin (e.g., anterior leg and gluteus), and improving skin rejuvenation (e.g., skin texture, color, and/or architecture). More importantly, an optimized width to depth ratio minimizes the risk of scarring while maximizing skin tightening. Non-thermal ablation forming ablated tissue portions with specific width to depth ratios improves healing time, treatment to abnormal skin areas, and increase the ability to tune hole depth and diameter to the treatment objective. Exemplary width to depth ratios include ratios between 1:0.3 to 1:1 (e.g., 1:0.3 to 1:1, 1:0.35 to 1:1, 1:0.4 to 1:1, 1:0.45 to 1:1, 1:0.5 to 1:1, 1:1 to 0.55 to 1:1, 1:0.6 to 1:1, 1:0.65 to 1:1, 1:0.7 to 1:1, 1:0.75 to 1:1, 1:0.8 to 1:1, 1:0.85 to 1:1, 1:0.9 to 1:1, 1:0.95 to 1:1, 1:0.3 to 1:0.95, 1:0.35 to 1:0.95, 1:0.4 to 1:0.95, 1:0.45 to 1:0.95, 1:0.5 to 1:0.95, 1:0.95 to 0.55 to 1:0.95, 1:0.6 to 1:0.95, 1:0.65 to 1:0.95, 1:0.7 to 1:0.95, 1:0.75 to 1:0.95, 1:0.8 to 1:0.95, 1:0.85 to 1:0.95, 1:0.9 to 1:0.95, 1:0.3 to 1:0.9, 1:0.35 to 1:0.9, 1:0.4 to 1:0.9, 1:0.45 to 1:0.9, 1:0.5 to 1:0.9, 1:0.9 to 1:0.9, 1:0.6 to 1:0.9, 1:0.65 to 1:0.9, 1:0.7 to 1:0.9, 1:0.75 to 1:0.9, 1:0.8 to 1:0.9, 1:0.85 to 1:0.9, 1:0.3 to 1:0.85, 1:0.35 to 1:0.85, 1:0.4 to 1:0.85, 1:0.45 to 1:0.85, 1:0.5 to 1:0.85, 1:0.85 to 0.55 to 1:0.85, 1:0.6 to 1:0.85, 1:0.65 to 1:0.85, 1:0.7 to 1:0.85, 1:0.75 to 1:0.85, 1:0.8 to 1:0.85, 1:0.3 to 1:0.8, 1:0.35 to 1:0.8, 1:0.4 to 1:0.8, 1:0.45 to 1:0.8, 1:0.5 to 1:0.8, 1:0.8 to 0.55 to 1:0.8, 1:0.6 to 1:0.8, 1:0.65 to 1:0.8, 1:0.7 to 1:0.8, 1:0.75 to 1:0.8, 1:0.3 to 1:0.75, 1:0.35 to 1:0.75, 1:0.4 to 1:0.75, 1:0.45 to 1:0.75, 1:0.5 to 1:0.75, 1:0.75 to 0.55 to 1:0.75, 1:0.6 to 1:0.75, 1:0.65 to 1:0.75, 1:0.7 to 1:0.75, 1:0.3 to 1:0.65, 1:0.35 to 1:0.65, 1:0.4 to 1:0.65, 1:0.45 to 1:0.65, 1:0.5 to 1:0.65, 1:0.65 to 0.55 to 1:0.65, 1:0.6 to 1:0.65, 1:0.3 to 1:0.65, 1:0.35 to 1:0.65, 1:0.4 to 1:0.65, 1:0.45 to 1:0.65, 1:0.5 to 1:0.65, 1:0.65 to 0.55 to 1:0.65, 1:0.6 to 1:0.65, 1:0.3 to 1:0.6, 1:0.35 to 1:0.6, 1:0.4 to 1:0.6, 1:0.45 to 1:0.6, 1:0.5 to 1:0.6, 1:0.6 to 0.55 to 1:0.6, 1:0.3 to 1:0.55, 1:0.35 to 1:0.55, 1:0.4 to 1:0.55, 1:0.45 to 1:0.55, 1:0.5 to 1:0.55, 1:0.3 to 1:0.5, 1:0.35 to 1:0.5, 1:0.4 to 1:0.5, 1:0.45 to 1:0.5, 1:0.5 to 1:0.5, 1:0.3 to 1:0.45, 1:0.35 to 1:0.45, 1:0.4 to 1:0.45, 1:0.3 to 1:0.4, 1:0.35 to 1:0.4, or 1:0.3 to 1:0.35) and 1:25 to 1:75 (e.g., 1:25 to 1:75, 1:30 to 1:75, 1:35 to 1:75, 1:40 to 1:75, 1:45 to 1:75, 1:50 to 1:75, 1:55 to 1:75, 1:60 to 1:75, 1:65 to 1:75, 1:70 to 1:75, 1:25 to 1:70, 1:30 to 1:70, 1:35 to 1:70, 1:40 to 1:70, 1:45 to 1:70, 1:50 to 1:70, 1:55 to 1:70, 1:60 to 1:70, 1:65 to 1:70, 1:25 to 1:65, 1:30 to 1:65, 1:35 to 1:65, 1:40 to 1:65, 1:45 to 1:65, 1:50 to 1:65, 1:55 to 1:65, 1:60 to 1:65, 1:25 to 1:60, 1:30 to 1:60, 1:35 to 1:60, 1:40 to 1:60, 1:45 to 1:60, 1:50 to 1:60, 1:55 to 1:60, 1:25 to 1:55, 1:30 to 1:55, 1:35 to 1:55, 1:40 to 1:55, 1:45 to 1:55, 1:50 to 1:55, 1:25 to 1:50, 1:30 to 1:50, 1:35 to 1:50, 1:40 to 1:50, 1:45 to 1:50, 1:25 to 1:45, 1:30 to 1:45, 1:35 to 1:45, 1:40 to 1:45, 1:25 to 1:40, 1:30 to 1:40, 1:35 to 1:40, 1:25 to 1:35, 1:30 to 1:35, or 1:25 to 1:30). Additional width-to-depth ratios are described herein, such as 1:1 to about 1:20 (e.g., any range described herein).

Exemplary ablated tissue portion widths include from about 0.1 mm to about 0.8 mm (e.g., 0.1 mm to 0.8 mm, 0.1 mm to 0.6 mm, 0.1 mm to 0.4 mm, 0.1 mm to 0.2 mm, 0.2 mm to 0.8 mm, 0.2 mm to 0.6 mm, 0.2 mm to 0.4 mm, 0.2 mm to 0.3 mm, 0.3 mm to 0.8 mm, 0.3 mm to 0.6 mm, 0.3 mm to 0.4 mm, 0.4 mm to 0.8 mm, 0.4 mm to 0.6 mm, 0.4 mm to 0.5 mm, 0.5 mm to 0.8 mm, 0.5 mm to 0.6 mm, 0.6 mm to 0.8 mm, 0.6 mm to 0.7 mm, or 0.7 mm to 0.8 mm). Exemplary ablated tissue portion widths includes 0.9 mm to 20 mm (e.g., 0.9 mm to 20 mm, 0.9 mm to 17 mm, 0.9 mm to 14 mm, 0.9 mm to 11 mm, 0.9 mm to 8 mm, 0.9 mm to 5 mm, 0.9 mm to 3 mm, 3 mm to 20 mm, 3 mm to 17 mm, 3 mm to 14 mm, 3 mm to 11 mm, 3 mm to 8 mm, 3 mm to 5 mm, 5 mm to 20 mm, 5 mm to 17 mm, 5 mm to 14 mm, 5 mm to 11 mm, 5 mm to 8 mm, 8 mm to 20 mm, 8 mm to 17 mm, 8 mm to 14 mm, 8 mm to 11 mm, 11 mm to 20 mm, 11 mm to 17 mm, 11 mm to 14 mm, 14 mm to 20 mm, 14 mm to 17 mm, or 17 mm to 20 mm) and 0.01 mm to 0.25 mm (e.g., 0.01 mm to 0.25 mm, 0.02 mm to 0.25 mm, 0.03 mm to 0.25 mm, 0.05 mm to 0.25 mm, 0.075 mm to 0.25 mm, 0.1 mm to 0.25 mm, 0.15 mm to 0.25 mm, 0.2 mm to 0.25 mm, 0.01 mm to 0.2 mm, 0.02 mm to 0.2 mm, 0.03 mm to 0.2 mm, 0.05 mm to 0.2 mm, 0.075 mm to 0.2 mm, 0.1 mm to 0.2 mm, 0.15 mm to 0.2 mm, 0.01 mm to 0.15 mm, 0.02 mm to 0.15 mm, 0.03 mm to 0.15 mm, 0.05 mm to 0.15 mm, 0.075 mm to 0.15 mm, 0.1 mm to 0.15 mm, 0.01 mm to 0.1 mm, 0.02 mm to 0.1 mm, 0.03 mm to 0.1 mm, 0.05 mm to 0.1 mm, 0.075 mm to 0.1 mm, 0.01 mm to 0.075 mm, 0.02 mm to 0.075 mm, 0.03 mm to 0.075 mm, 0.05 mm to 0.075 mm, 0.01 mm to 0.05 mm, 0.02 mm to 0.05 mm, 0.03 mm to 0.05 mm, 0.01 mm to 0.03 mm, 0.02 mm to 0.03 mm, 0.03 mm to 0.03 mm, 0.01 mm to 0.03 mm, 0.02 mm to 0.03 mm, or 0.01 mm to 0.02 mm). Further non-limiting exemplary ablated tissue portion widths and/or lengths include from about 0.01 mm to about 20 mm or from about 0.01 mm to about 2 mm (e.g., such as any range described herein).

Changes in Width Along the Depth

The present invention allows for tissue portions having changes in width. Benefits for optimizing such changes include improved ablated tissue portion closing (e.g., a larger diameter at skin surface and smaller diameter in the skin depth will facilitate hole closing or, alternatively, a small diameter at skin surface and larger diameter in skin depth may accelerate closure of the epidermal layer and therefore minimize risk of adverse events, such as infections, and minimize healing time), increased surface area of the inside of the ablated tissue portion or hole, or improved directional healing response by having an offset increase of diameter, thus biasing hole closure upon compression in a single direction. Exemplary changes include a change in width of between about 10 μm to about 1000 μm as a function of depth, such as any range described herein. In one non-limiting embodiment, the change is about 100 μm at the skin surface and about 500 μm at the bottom of the dermal layer (e.g., to minimize closure time of the epidermal layer, such as reepithelialization). In another non-limiting embodiment, the change is about 400 μm at the skin surface and between about 0 to about 200 μm at the bottom of the dermal layer (e.g., to facilitate hole mechanical closure).

Serrated Cross-Sectional Dimension

The present invention also allows for tissue portions having a serrated or scalloped cross-sectional dimension. Benefits for serrated cross-sectional dimensions include increased surface area for binding tissue together with or without glues or sealants, thus improving the strength of a closure. In addition, serrated edges provide a mechanism to bias hole closing. For example, the serrated internal pattern of an ablated tissue portion may be configured such that when compressed in a first direction, the serrated structures from opposite sides of the wound interlock, thus allowing complete closure of the hole. In some embodiments, the serrated or scalloped cross-sectional dimensions occur in the x-axis, y-axis, or xy-axis. In other embodiments, the serrated or scalloped cross-sectional dimensions occur in the z-axis. Exemplary serrated cross-sectional dimensions include regular or irregular ridges or depressions in the side wall of an ablated tissue portion or hole equal in height to 10% of the hole diameter. In other embodiments, the height of the regular or irregular ridges or depressions is between 5% and 70% of the diameter of the ablated tissue portion (e.g., between 5% and 10%, 5% and 20%, 5% and 30%, 5% and 40%, 5% and 50%, 5% and 60%, 5% and 70%, 10% and 20%, 10% and 30%, 10% and 40%, 10% and 50%, 10% and 60%, 10% and 70%, 20% and 30%, 20% and 40%, 20% and 50%, 20% and 60%, 20% and 70%, 30% and 40%, 30% and 50%, 30% and 60%, 30% and 70%, 40% and 50%, 40% and 60%, 40% and 70%, 50% and 60%, 50% and 70%, or 60% and 70%).

Ablation Apparatuses and Methods for Non-Thermal Ablation of Tissue

The present invention features methods, apparatuses and devices for generating ablated tissue portions (e.g., microwounds or incised or excised tissue portions) without imparting thermal energy to the surrounding tissue. Exemplary devices include those which selectively generate an ablated tissue portion using a drill, driver (e.g., a pile driver (e.g., a tattoo gun that uses solid needles), which compresses, shears, and destroys the tissue as it cycles up and down in the z-axis), wire or flexible fiber, blade, high pressure fluid jet, cryoprobes or cryoneedles, chemical treatment, non-thermal energy, or direct vacuum. In particular, wounds generated without the use of thermal energy by methods and devices of this invention may desirably have an areal dimension of less than 4 mm$^2$ and/or a volumetric dimension that is less than about 6 mm$^3$. Methods and devices for non-thermal ablation may form holes with multiple diameters along the wound depth. The present invention also features methods and devices for making ablated tissue portions with serrated or non-uniform edges along the depth of the ablated tissue portion. One or more therapeutic agents (e.g. an anticoagulant) may be added prior to, during, or after ablation of tissue.

Drills

The present invention features methods, devices, and apparatuses for rotating a penetrating component that may be used to ablate skin in a fractional pattern. The mechanical fractional ablation apparatus includes a motor (e.g., electric or pneumatic motor) for rotation of a penetrating component or an array of penetrating components.

The penetrating component is positioned to be in contact with the skin outer surface (epidermis), the motor is activated, and the apparatus is pushed toward the skin until it reaches a pre-set depth. An optional adjustable depth stop may limit the ablation depth. The ablation depth may be adjusted to remove only a portion of the skin (i.e., epidermis and part of the dermis) or to remove the full epidermis and dermis thickness. Full thickness removal may be beneficial for skin tightening. Removing only part of the thickness of the skin region may be beneficial for improvement of the tissue texture and/or color and/or to accelerate healing. In one embodiment, a penetrating component may be a drill bit having spiral channels along its long axis to carve away the tissue and create the ablation and carry the tissue up the bit as it turns.

Ablative apparatuses may be designed to spin at a range of rotational speeds (e.g., greater than 50 rpm or between about 50 rpm to about 2500 rpm) that may be selected to produce the desired effect (e.g., ablation creates well defined regions of tissue with clean margins), while reducing or eliminating undesirable effects, such as heat production and tissue shredding. In another embodiment, a drill includes micro-augers in which the penetrating component consists of a spiral flange for cutting into the tissue and conveying the tissue up to the surface of the skin for elimination. In particular non-limiting embodiments, it might be beneficial to work at lower speed to minimize heating of the tissue and to improve cutting performance through soft materials. In this context, an exemplary non-limiting maximal rotational speed is about 2500 rpm while allowing for very low speeds above about 50 rpm. Exemplary rotational speeds include from about 50 rpm to about 2500 rpm (e.g., 50 rpm to 100 rpm, 50 rpm to 250 rpm, 50 rpm to 500 rpm, 50 rpm to 750 rpm, 50 rpm to 1000 rpm, 50 rpm to 1500 rpm, 50 rpm to 2000 rpm, 50 rpm to 2500 rpm, 75 rpm to 100 rpm, 75 rpm to 250 rpm, 75 rpm to 500 rpm, 75 rpm to 750 rpm, 75 rpm to 1000 rpm, 75 rpm to 1500 rpm, 75 rpm to 2000 rpm, 75 rpm to 2500 rpm, 100 rpm to 250 rpm, 100 rpm to 500 rpm, 100 rpm to 750 rpm, 100 rpm to 1000 rpm, 100 rpm to 1500 rpm, 100 rpm to 2000 rpm, 100 rpm to 2500 rpm, 250 rpm to 500 rpm, 250 rpm to 750 rpm, 250 rpm to 1000 rpm, 250 rpm to 1500 rpm, 250 rpm to 2000 rpm, 250 rpm to 2500 rpm, 500 rpm to 750 rpm, 500 rpm to 1000 rpm, 500 rpm to 1500 rpm, 500 rpm to 2000 rpm, 500 rpm to 2500 rpm, 750 rpm to 1000 rpm, 750 rpm to 1500 rpm, 750 rpm to 2000 rpm, 750 rpm to 2500 rpm, 1000 rpm to 1500 rpm, 1000 rpm to 2000 rpm, 1000 rpm to 2500 rpm, 1500 rpm to 2000 rpm, 1500 rpm to 2500 rpm, or 2000 rpm to 2500 rpm).

Alternatively, a micro-auger may be configured to move tissue and debris to another region where it may be eliminated. For example, the flange may have a spiral configured to push the cuttings downward away from the site of ablation. A spiral channel or flange may be on a portion of the penetrating component or along its entire length. The cuttings may be removed in a second step or left to be resorbed by the body in a subdermal location.

Many drill bit designs are contemplated, including drill bits which are employed for use in non-medical fields such as construction, engineering, and general mechanical applications. The drill bits may be fashioned from a wide variety of materials; non-limiting examples include: metals, plastics, silicon, crystalline materials, and non crystalline materials. The drill bits may be hollow or solid. Hollow drills may be fashioned to have a channel through their core that conveys a vacuum for elimination of tissue cuttings. Penetrating components may be cooled or heated to control the temperature of the surrounding tissue. The pattern of the flange or spiral channels may be fashioned to optimize the ablation and/or transport of tissue such as adipose tissue, dermis, or epidermal tissue.

In another embodiment, drilling through soft tissue (e.g., skin) may be achieved with a hollow tube having a sharp cutting edge (e.g., a paper drill). Ablated tissue is captured in the hollow drill bit. Alternatively, the hollow tube may be pushed through the skin by a high-frequency vibrating mechanism (e.g., a piezo actuator operated at high frequency). In another alternative, a tube having a sharp edge and cutting teeth (e.g., a hole saw) may be used. Similarly, tissue is captured in the hollow drill bit. A spoon bit may also be used to ablate tissue. A spoon bit is constituted of a grooved shank and is shaped like the bowl of a spoon. The edges of the bit are sharp and cut through tissue.

In another embodiment, tissue may be hardened before drilling, e.g., by local freezing. This allows use of twist drill bits having a cutting point at the tip of a cylindrical shaft with helical flutes for removal of cut tissue. Freezing may be achieved by application of a freezing agent (e.g. liquid nitrogen or argon gas) or by application of a freezing probe on the skin surface. Alternatively, a drill bit may be cooled such that it causes flash freezing of the tissue immediately surrounding the area of contact with the drill bit. Freezing of the tissue in this manner may enable an improved ablation pattern and/or reduce pain and bleeding during the procedure.

Exemplary drill bits for any of the above embodiments are a twist bit, hole saw bit, paper drill bit, step drill bit, unibit, lip or spur bit (brad point bit), spade bit, spoon bit, Forstner bit, center bit, auger bit, gimlet bit, installer bit, two-flute bit, three-flute bit, core drill bit, countersink bit, gun drill bit, microauger, tube with cutting teeth, and other drill bits known in the art.

Drill bits according to any of the above embodiments of the invention can be made from many materials, including metals, metal alloys, shape memory materials, plastics, ceramics, and composite materials such as metals and metal alloys coated with black oxide, titanium nitride, titanium aluminum nitride, titanium carbon nitride, diamond powder, zirconium nitride, and other hardening agents and combinations of the materials herein.

Wires and Fibers

The invention further features devices, methods, and apparatuses that include wires (e.g. metallic or non-metallic wires or fibers) or an array of wires or fibers that can be used to ablate skin in a fractional pattern.

In one embodiment, a wire is attached to a very thin axle (e.g., a needle) at one point or at two points to form a loop. The axle has a point at one end to facilitate insertion into the skin. The other end of the axle may be attached to a motor that drives the axle. When the motor is activated, the axle rotates along the longitudinal axis, driving the wire loop at high speed to cut through the skin tissue. The axle can rotate at any useful speed, such as about 500 rpm to about 5000 rpm (e.g., from 500 rpm to 1000 rpm, 500 rpm to 2000 rpm, 500 rpm to 3000 rpm, 500 rpm to 4000 rpm, 750 rpm to 1000 rpm, 750 rpm to 2000 rpm, 750 rpm to 3000 rpm, 750 rpm to 4000 rpm, 750 rpm to 5000 rpm, 1000 rpm to 2000 rpm, 1000 rpm to 3000 rpm, 1000 rpm to 4000 rpm, 1000 rpm to 5000 rpm, 1500 rpm to 2000 rpm, 1500 rpm to 3000 rpm, 1500 rpm to 4000 rpm, 1500 rpm to 5000 rpm, 2000 rpm to 3000 rpm, 2000 rpm to 4000 rpm, 2000 rpm to 5000 rpm, 2500 rpm to 3000 rpm, 2500 rpm to 4000 rpm, or 2500 rpm to 5000 rpm).

In another embodiment, a wire is attached to an axle having the same diameter as the hole to be created. The wire may be attached off-center and to the outer diameter of the axle. The wire is parallel to the long axis of the axle. When the axle is rotating at high speed along its long axis, the wire trajectory defines a cylinder, co-axial with and of the same diameter as the axle. The wire or fiber may be inserted in the skin while the axle is rotating to cut a cylindrical hole. In one embodiment, the wire or fiber is of a fixed shape and length. In other embodiments, the shape and length of the wire may be changed to produce different ablation diameters along the Z axis. Specifically, a larger diameter hole portion may be produced on top of a narrower diameter hole portion. This may be desirable when targeting certain tissues for ablation such as subdermal fat. A wire or fiber may be fed through a hollow channel in the penetrating component. The amount of wire fed through the penetrating component may be adjusted as the component penetrates the tissue. The wire/fiber may also be retracted as the penetrating component is translated through the tissue, thus creating a gradient of hole diameters along the hole depth. The wire or fiber may be stiff and possess shape memory, may be flexible, or possess a mixture of the both rigidity and ductility along the length of the wire or fiber. In some embodiments, the wire or fiber includes preset volumetric contours. In other embodiments, the wire or fiber includes vertical mire loops (e.g., to slice away tissue, like potato peeler from the surface across the x-y plane of the skin).

In other embodiments a fiber can be used in place of a wire. Fibers can be attached at a single point or at dual points along the axis of a rotating member. Fibers can be rigid (e.g. a hard plastic such as PEEK) or ductile (e.g., a flexible plastic such as polyethylene). The fiber can be a composite (e.g., glass filled polypropylene) to improve or alter the mechanical properties.

Many types of wires or fibers can be used in the present invention. For example, wires can be single stranded, braided, or composites of individual wires of a single or multiple gauges or diameters. Wires can have diameters such that the wire can be attached to a rotating component and ablate tissue within the desired hole diameter. For example, a wire can have a diameter ranging from 30 gauge to 40 gauge (American gauge wire, 255 µm to 80 µm). The diameter of the wire can be less than 80 µm. In some embodiments, the length of the wire can be between about 100 µm and about 5000 µm (e.g., 100 µm and 250 µm, 100 µm and 500 µm, 100 µm and 750 µm, 100 µm and 1000 µm, 100 µm and 1500 µm, 100 µm and 2000 µm, 100 µm and 2500 µm, 100 µm and 3000 µm, 100 µm and 3500 µm, 100 µm and 4000 µm, 100 µm and 4500 µm, 200 µm and 250 µm, 200 µm and 500 µm, 200 µm and 750 µm, 200 µm and 1000 µm, 200 µm and 1500 µm, 200 µm and 2000 µm, 200 µm and 2500 µm, 200 µm and 3000 µm, 200 µm and 3500 µm, 200 µm and 4000 µm, 200 µm and 4500 µm, 300 µm and 500 µm, 300 µm and 750 µm, 300 µm and 1000 µm, 300 µm and 1500 µm, 300 µm and 2000 µm, 300 µm and 2500 µm, 300 µm and 3000 µm, 300 µm and 3500 µm, 300 µm and 4000 µm, 300 µm and 4500 µm, 400 µm and 500 µm, 400 µm and 750 µm, 400 µm and 1000 µm, 400 µm and 1500 µm, 400 µm and 2000 µm, 400 µm and 2500 µm, 400 µm and 3000 µm, 400 µm and 3500 µm, 400 µm and 4000 µm, 400 µm and 4500 µm, 500 µm and 750 µm, 500 µm and 1000 µm, 500 µm and 1500 µm, 500 µm and 2000 µm, 500 µm and 2500 µm, 500 µm and 3000 µm, 500 µm and 3500 µm, 500 µm and 4000 µm, 500 µm and 4500 µm, 600 µm and 750 µm, 600 µm and 1000 µm, 600 µm and 1500 µm, 600 µm and 2000 µm, 600 µm and 2500 µm, 600 µm and 3000 µm, 600 µm and 3500 µm, 600 µm and 4000 µm, 600 µm and 4500 µm, 700 µm and 750 µm, 700 µm and 1000 µm, 700 µm and 1500 µm, 700 µm and 2000 µm, 700 µm and 2500 µm, 700 µm and 3000 µm, 700 µm and 3500 µm, 700 µm and 4000 µm, 700 µm and 4500 µm, 800 µm and 1000 µm, 800 µm and 1500 µm, 800 µm and 2000 µm, 800 µm and 2500 µm, 800 µm and 3000 µm, 800 µm and 3500 µm, 800 µm and 4000 µm, 800 µm and 4500 µm, 900 µm and 1000 µm, 900 µm and 1500 µm, 900 µm and 2000 µm, 900 µm and 2500 µm, 900 µm and 3000 µm, 900 µm and 3500 µm, 900 µm and 4000 µm, 900 µm and 4500 µm, 1000 µm and 1500 µm, 1000 µm and 2000 µm, 1000 µm and 2500 µm, 1000 µm and 3000 µm, 1000 µm and 3500 µm, 1000 µm and 4000 µm, 1000 µm and 4500 µm, 1500 µm and 2000 µm, 1500 µm and 2500 µm, 1500 µm and 3000 µm, 1500 µm and 3500 µm, 1500 µm and 4000 µm, 1500 µm and 4500 µm, 2000 µm and 2500 µm, 2000 µm and 3000 µm, 2000 µm and 3500 µm, 2000 µm and 4000 µm, or 2000 µm and 4500 µm).

Blades

The invention also features blades or an array of blades that may ablate skin in a fractional pattern. In one embodiment, a cylindrical blade having the diameter of the hole to be generated may be pushed into the skin to cut a cylindrical hole (e.g., a cylindrical tube with a blade edge or a microcoring component). The blade may be rotated to assist in the tissue ablation. The depth of the hole may be controlled by manually controlling the depth of the blade or by using a depth stop. The ablated tissue portion inside the cylindrical blade may be removed with a pin, vacuum, positive pressure or other methods described herein.

In another embodiment, straight blade(s) may be used to generate holes that are not cylindrical. Different patterns of holes may be cut depending on the geometry and number of blades (e.g. triangle, hexagon, or octagon). Blades may be inserted into the tissues with sufficient force and speed to produce a desired effect. Alternatively, the blades may be oscillated or vibrated at high frequency to enable insertion at lower speed and force (e.g., similar to vibration enhanced commercially available electric knives and scalpels).

In another embodiment, a plurality of blades is assembled into an array to simultaneously cut multiple holes. For example, four blades may be assembled as to generate a blade with a square hole. Several of these square blades may be combined to form an array of blades. The square blades may be spaced within the array and sized to provide a 5-40% areal removal of skin once pressed into the tissue and removed. The ablated tissue portions may be closed with a variety of methods (e.g., dressings, sutures, closures, and other compressive means). Upon healing the skin volume will be reduced, thus tightening or reducing the laxity of the skin region.

In another embodiment, the pattern of ablations may be adjusted with a variety of flat cutting blades by changing the pattern of cuts in the tissue. For example, diamond patterns or octagonal patterns may be produced with a single blade or multiple cutting blades. Ablations of desired geometries may be generated by sequential insertion of a single blade in which the orientation of the blade is changed with respect to the previous incision.

The removal of the ablated tissue (e.g., the circumscribed tissue region) may be accomplished with a variety of mechanisms. Mechanical means (e.g., a hook, a scoop, an adhesive), negative pressure (e.g., a vacuum), or positive pressure (e.g., fluid or gas pressure) may be used to remove the ablated tissue portion from the ablation apparatus.

Non-limiting exemplary blades include; taps, cutters, corers, reamers, awls, broaches, step core, pinch, core, rotary, and punches. Exemplary blade materials include: metal (e.g., a stainless steel tube, 304 stainless steel, a surgical stainless steel), metal alloys, polymer or plastic, glass, ceramics, or other structural materials. Blades may be a composite of one or more materials including: metals and metal alloys coated with black oxide, titanium nitride, titanium aluminum nitride, titanium carbon nitride, diamond powder, zirconium nitride, and other hardening agents and combinations of materials such as polymers, plastics, ceramics and other structural materials. Additional exemplary coatings include a lubricant, a low-friction material (e.g., Teflon™), a chromium coating (e.g., ME-92™, such as to increase material strength), a plastic, a polymer (e.g., nylon or polyethylene), a polished metal alloy, or the like.

Further, the tubes, blades, pins, and ablation apparatuses can be formed from any useful material and optionally coated or chemically treated to promote incision or excision of a tissue portion and/or to increase precision or effectiveness for treating the skin region. Exemplary materials include metal, a biopsy needle, an epoxy, a glass, a polymer, a plastic, a resin, another structurally rigid material, or a similar structure.

High Pressure Fluid Jet

In other embodiments, the invention features high pressure fluid jets or an array of high pressure fluid jets that may ablate skin in a fractional pattern.

In one embodiment, an ablation apparatus containing at least one high pressure fluid jet (e.g., fluid pressure of greater than 1380 kPa or 200 psi) may be positioned external to the skin surface. The high pressure fluid jet is applied to the skin surface, thus producing a hole. The size of the hole may be determined by the fluid jet size and length of exposure. For example, to provide an ablated skin portion with a shallower depth, the fluid jet may be applied for a shorter time. Alternatively, to provide an ablated skin portion with a greater depth or diameter, the fluid jet may be applied to the skin region for a longer time. A high pressure fluid jet is a non-thermal ablative mechanism and does not generate a thermal injury to the surrounding tissue. An exemplary method for removing excess fluid, tissue or debris generated during ablation is using a vacuum source (negative pressure) or a pressurized air stream (positive pressure).

Exemplary non-limiting pressures include from about 200 psi to about 100000 psi (e.g., from 200 psi to 1000 psi, 200 psi to 5000 psi, 200 psi to 10000 psi, 200 psi to 50000 psi, 500 psi to 1000 psi, 500 psi to 5000 psi, 500 psi to 10000 psi, 500 psi to 50000 psi, 500 psi to 100000 psi, 750 psi to 1000 psi, 750 psi to 5000 psi, 750 psi to 10000 psi, 750 psi to 50000 psi, 750 psi to 100000 psi, 1000 psi to 5000 psi, 1000 psi to 10000 psi, 1000 psi to 50000 psi, 1000 psi to 100000 psi, 1500 psi to 5000 psi, 1500 psi to 10000 psi, 1500 psi to 50000 psi, 1500 psi to 100000 psi, 2000 psi to 5000 psi, 2000 psi to 10000 psi, 2000 psi to 50000 psi, 2000 psi to 100000 psi, 2500 psi to 5000 psi, 2500 psi to 10000 psi, 2500 psi to 50000 psi, 2500 psi to 100000 psi, 4000 psi to 5000 psi, 4000 psi to 10000 psi, 4000 psi to 50000 psi, 4000 psi to 100000 psi, 5000 psi to 10000 psi, 5000 psi to 50000 psi, 5000 psi to 100000 psi, 7500 psi to 10000 psi, 7500 psi to 50000 psi, 7500 psi to 100000 psi, 10000 psi to 50000 psi, 10000 psi to 100000 psi, 50000 psi to 100000 psi, or 75000 psi to 100000 psi).

In another embodiment, an ablation apparatus containing fluid jets is inserted in the fatty layer, under the dermis and epidermis. The array of high pressure fluid jets emits fluid at very high pressure to ablate the tissue above. A low pressure out-flow tube may be positioned on the surface of the skin to remove fluid and debris. In another embodiment, a discontinuous fluid flow may be used to allow removal of fluid and debris before reactivating the high-pressure jet. In another embodiment, the jet array can be moved (e.g., in a circular fashion) in relation to the skin so as to produce an array of cylindrical ablations.

High pressure fluid jets of the invention may be a coherent fluid stream or an incoherent fluid stream. One or more nozzles may be used to form the fluid jet. For example, a convergent nozzle may be used which reduces the diameter of the outlet, thus increasing the velocity of the fluid jet.

Many fluids may be used to make the high pressure fluid jet. Non-limiting examples include: aqueous and non aqueous solutions, such as isotonic and non isotonic buffers, and saline solutions, and may include additional ingredients that have a desirable medical or aesthetic activity or utility. Exemplary additional therapeutic agents include but are not limited to heparin, fibrin, antibiotics, lidocaine and other analgesics.

Cryosurgery

Tissue ablation according to the invention may also be accomplished by cryosurgery, in which extreme cold is used to destroy tissue. Cryosurgery is a less invasive alternative to surgery; and generally has less complications and side effects. Cold temperature is typically generated with a cryogen, such as liquid nitrogen (−196 degrees C.), carbon dioxide (−78.5 degrees C.), argon gas (−185.5 degrees C.), and/or dimethyl ether-propane (−41 degrees C.), or cold probes.

Ablation of tissue in a fractional pattern may be achieved by cryosurgery. Ablated columns of tissue resorb and are replaced by healthy tissue. This fractional ablation technology is less invasive than fractional surgical ablation. This results in faster healing and may limit side effects and other complications (e.g., no bleeding, lower risk of infection). Following fractional cryosurgery, a compressive wound dressing may be applied to the skin to enhance skin tightening.

In one embodiment an array of miniature cold probes is applied to a skin region. The probes locally decrease the skin temperature, thus freezing and destroying and/or ablating the tissue at the skin region surface. The resulting ablation is superficial (e.g., only at the skin surface) which provides ablated tissue portions with high width to depth ratios. Therefore, this technique is well suited to improvement of skin texture and color.

In another embodiment, cold needles are inserted into the skin region. This embodiment allows ablation of deep skin tissue. One may envision the formation of full depth skin ablations (i.e. ablation of the epidermis and dermis layer). Ablated tissue portions spanning both the epidermis and dermis layers of the skin are best suited for skin tightening. To maximize the skin tightening treatment, the ablation is followed by a compressive wound dressing. The penetrating components may be temperature controlled and may consist of a temperature conductive material. The temperature conductive material may be brought into proximity with a heat sink. Given the small size of the penetrating components, such cooling may occur within seconds or sub-second timeframes. Such temperature conductive materials include metals such as copper and stainless steel.

In another embodiment, penetrating components may be fashioned to include regions composed of temperature non-conductive (e.g., insulator) materials to help shield regions of the tissue or imbed patterns into the tissue from exposure to extremes of temperature. For example, a cryoneedle can be coated with an insulating material on only one side, thus leaving the other side of the needle thermally conducting. After reducing the temperature of the cryoneedle with a heat sink, the thermally conductive side will freeze tissue while the sides coated with an insulator will not, thus forming asymmetric hole diameters (e.g. non-circular).

Needles can be cooled by any useful process. In one non-limiting example, one can envision attaching the needles to a Peltier cell (heat pump) that cools the needles, while the other side of the Pelletier cell is heated and heat is dissipated through radiators. In another non-limiting example, a cooling fluid may be circulated in the needle (e.g., the apparatus can include an internal needle and an external needle, where the internal needle includes a first material having conductive properties (e.g., a metal, such as any described herein) and includes a cryogen within the lumen of the internal needle, thereby cooling the external needle). In other embodiments, the external needle includes a second material on its distal end (e.g., silver). In yet another non-limiting example, the needle may be used as a micro-evaporator in a refrigerating circuit.

Chemical or Bioactive Agents

In another embodiment, chemical or bioactive agents may also be used to destroy or ablate skin tissue. Typical chemical or bioactive agents used include trichloracetic acid, alpha hydroxy acids, beta hydroxy acids, liquid nitrogen, hypoosmotic fluids, hyperosmotic fluids, and bioactive proteins (e.g., one or more hormones, antibodies, and/or enzymes, such as enzymes that liquefy tissue, such as one or more proteases, DNases, hyaluronidase, and collagenases, or combinations thereof). Chemicals or bioactive agents are used to create an injury, ablated tissue portion, and/or stimulate new tissue formation.

In one embodiment, tissue may be denatured, ablated, and/or destroyed in a fractional pattern with chemical or bioactive agents. For example, an array of needles with side-holes along the needle body may be introduced in the skin. The multiple side-holes in the needles allows for injection of a chemical or bioactive denaturizing agent at multiple depths, allowing for full-thickness denaturation of columns of skin tissue.

In another embodiment, the needle side-holes can be configured to supply a chemical or bioactive agent to specific areas along the needle or in a specific pattern. In addition, the size of the needle side holes may control the amount of chemical or bioactive agent delivered to a particular location. This embodiment allows for the formation of ablated tissue portions with multiple diameters along the length, asymmetric structures, and serrated cross-sectional dimension.

Microelectrodes

In yet another embodiment, ablation may be accomplished by non-thermal irreversible electroporation, which involves the application of very short bursts of electricity (microsecond duration range) at a specific voltage and frequency to form nanopores in the cell membrane. The electroporation parameters may be selected to form reversible pores (i.e., the cell may repair and restore normal function) or irreversible pores (i.e., the treatment produces cell apoptosis). The electroporation may be configured to use a set of parameters such that the energy only affects targeted tissue. For example, a specific cell type may be destroyed without affecting an extracellular matrix, nerves, or blood vessels. Small electrodes (diameter in the mm range) are typically used for electroporation.

In one embodiment, a non-thermal irreversible electroporation may be used for fractional skin region or tissue ablation. Carefully selected treatment parameters limit the effect of the electroporation to the skin region, thus leaving blood vessels and nerve fibers substantially unaffected and without significant heating of the surrounding tissue. For example, a pair of needle electrodes may be inserted into a skin region. A first electrode of the electrode pair may be an active electrode and the second electrode of the pair may be a return electrode. The ablated tissue portion occurs in the tissue volume between the electrode pair. The electrical parameters (e.g., the voltage, current and power) between the active and return electrode may be selected to affect only the desired tissue and provide ablation in a specific location.

In another embodiment, the electrodes may be configured to affect only cells in the dermal layer while leaving the epidermal cells unaffected. The electrode or electrode pair may be located only at the tip of the needle (e.g., the upper portion of the needle is not conductive). In this embodiment, the electroporation between the electrode pair only occurs in the dermal layer, thus providing selective ablation of the dermis.

Another embodiment for irreversible electroporation includes insertion of an array of needles into a skin region. The needles are connected to a generator that emits pulses of electricity of pre-selected duration, frequency, and intensity. The array includes pairs of electrodes, each having an active electrode and a return electrode located in close proximity to generate a pulsed and high intensity electrical field between the pairs of electrodes. The electrical field leads to non-thermal, irreversible electroporation of the tissue located between electrode pairs. The treatment parameters are selected as to only generate apoptosis of skin cells. In a further embodiment, the electrode pairs can be positioned in a non-parallel configuration, thus producing ablated tissue portions with varied geometry, diameters, and serrated cross-sectional dimensions.

In another embodiment, a probe or needle containing multiple electrodes (e.g., each having an active and a return electrode pair) may be used to form bi-polar electrodes for the electroporation of tissue. Bi-polar electrodes consist of two conductive surfaces separated by an electrical insulator. One conductive surface acts as an active electrode while the other surface acts as a return electrode. Ablated tissue portions can be formed around the bi-polar electrode as the electrical energy moves through the tissue adjacent to the bi-polar electrode. In a further embodiment, the bi-polar electrode may have different shapes or geometric configurations, thus producing ablated tissue portions with varied geometry, diameters, and serrated cross-sectional dimensions. In other embodiments, the electrodes may be monopolar.

Exemplary conductive materials include metals (e.g., copper and aluminum), metal alloys, electrolyte gels, and conductive polymers. Exemplary insulator materials include polyvinylchloride (PVC), glass, polytetrafluoroethylene (PTFE), and ceramics.

The microelectrodes, probes, and needles can be have useful voltage, amperage, and/or frequency. The electric field generated on the skin can be, e.g., from about 500 V/cm to 5000 V/cm (e.g., from 500 V/cm to 1000 V/cm, 500 V/cm to 2000 V/cm, 500 V/cm to 3000 V/cm, 500 V/cm to 4000 V/cm, 600 V/cm to 1000 V/cm, 600 V/cm to 2000 V/cm, 600 V/cm to 3000 V/cm, 600 V/cm to 4000 V/cm, 600 V/cm to 5000 V/cm, 700 V/cm to 1000 V/cm, 700 V/cm to 2000 V/cm, 700 V/cm to 3000 V/cm, 700 V/cm to 4000 V/cm, 700 V/cm to 5000 V/cm, 800 V/cm to 1000 V/cm, 800 V/cm to 2000 V/cm, 800 V/cm to 3000 V/cm, 800 V/cm to 4000 V/cm, 800 V/cm to 5000 V/cm, 900 V/cm to 1000 V/cm, 900 V/cm to 2000 V/cm, 900 V/cm to 3000 V/cm, 900 V/cm to 4000 V/cm, or 900 V/cm to 5000 V/cm).

In addition, the voltage-loaded area average electric field can be between, e.g., about 5 V/cm to about 900 V/cm (e.g., from 5 V/cm to 100 V/cm, 5 V/cm to 200 V/cm, 5 V/cm to 300 V/cm, 5 V/cm to 400 V/cm, 5 V/cm to 500 V/cm, 5 V/cm to 600 V/cm, 5 V/cm to 700 V/cm, 5 V/cm to 800 V/cm, 10 V/cm to 100 V/cm, 10 V/cm to 200 V/cm, 10 V/cm to 300 V/cm, 10 V/cm to 400 V/cm, 10 V/cm to 500 V/cm, 10 V/cm to 600 V/cm, 10 V/cm to 700 V/cm, 10 V/cm to 800 V/cm, 10 V/cm to 900 V/cm, 15 V/cm to 100 V/cm, 15 V/cm to 200 V/cm, 15 V/cm to 300 V/cm, 15 V/cm to 400 V/cm, 15 V/cm to 500 V/cm, 15 V/cm to 600 V/cm, 15 V/cm to 700 V/cm, 15 V/cm to 800 V/cm, 15 V/cm to 900 V/cm, 25 V/cm to 100 V/cm, 25 V/cm to 200 V/cm, 25 V/cm to 300 V/cm, 25 V/cm to 400 V/cm, 25 V/cm to 500 V/cm, 25 V/cm to 600 V/cm, 25 V/cm to 700 V/cm, 25 V/cm to 800 V/cm, 25 V/cm to 900 V/cm, 50 V/cm to 100 V/cm, 50 V/cm to 200 V/cm, 50 V/cm to 300 V/cm, 50 V/cm to 400 V/cm, 50 V/cm to 500 V/cm, 50 V/cm to 600 V/cm, 50 V/cm to 700 V/cm, 50 V/cm to 800 V/cm, 50 V/cm to 900 V/cm, 75 V/cm to 100 V/cm, 75 V/cm to 200 V/cm, 75 V/cm to 300 V/cm, 75 V/cm to 400 V/cm, 75 V/cm to 500 V/cm, 75 V/cm to 600 V/cm, 75 V/cm to 700 V/cm, 75 V/cm to 800 V/cm, or 75 V/cm to 900 V/cm).

The voltage (e.g., RF voltage in pulse or continuous mode) can be from about 10 $V_{RMS}$ to about 200 $V_{RMS}$ (e.g., 10 $V_{RMS}$ to 50 $V_{RMS}$, 10 $V_{RMS}$ to 100 $V_{RMS}$, 10 $V_{RMS}$ to 150 $V_{RMS}$, 15 $V_{RMS}$ to 50 $V_{RMS}$, 15 $V_{RMS}$ to 100 $V_{RMS}$, 15 $V_{RMS}$ to 150 $V_{RMS}$, 15 $V_{RMS}$ to 200 $V_{RMS}$, 20 $V_{RMS}$ to 50 $V_{RMS}$, 20 $V_{RMS}$ to 100 $V_{RMS}$, 20 $V_{RMS}$ to 150 $V_{RMS}$, 20 $V_{RMS}$ to 200 $V_{RMS}$, 30 $V_{RMS}$ to 50 $V_{RMS}$, 30 $V_{RMS}$ to 100 $V_{RMS}$, 30 $V_{RMS}$ to 150 $V_{RMS}$, 30 $V_{RMS}$ to 200 $V_{RMS}$, 40 $V_{RMS}$ to 50 $V_{RMS}$, 40 $V_{RMS}$ to 100 $V_{RMS}$, 40 $V_{RMS}$ to 150 $V_{RMS}$, or 40 $V_{RMS}$ to 200 $V_{Rms}$) In some non-limiting embodiments, the load voltage can be from about 300 V to about 600 V. In other embodiments, the applied voltage is from about 100 V to about 2000 V (e.g., from 100 V to 500 V, 100 V to 1000 V, 100 V to 1500 V, 250 V to 500 V, 250 V to 1000 V, 250 V to 1500 V, 250 V to 2000 V, 500 V to 1000 V, 500 V to 1500 V, 500 V to 2000 V, 750 V to 1000 V, 750 V to 1500 V, or 750 V to 2000 V). In general, high-voltage (e.g., more than about 150V) results in electroporation of skin. Furthermore, transdermal voltage for electroporation can be temperature dependent. For the non-limiting example of human stratum corneum, electroporation occurs at a transdermal voltage difference of 80 V<Uskin<100 V at 4° C. or 10 V<Uskin<20 V at 60° C. (see, e.g., Pliquett et al., J Theor Biol. 2008 Mar. 21; 251(2): 195-201).

Further, voltage can be provided in pulse or continuous mode. Non-limiting exemplary protocols include (i) 10 pulses of 1000 V (applied voltage) of 100 ms duration (10×1000 V-100 ms) and (ii) 10 pulses of 335 V, each with a duration of 5 ms.

Current (e.g., DC or AC) can be of any amplitude that allows for ablation. Non-limiting exemplary ranges include from about 0.1 A to 5 A, from about 10 mA to 500 mA, or from about 100 µA to about 1000 µA. In general, small electrical currents (e.g., more than about 0.4 mA/cm$^2$) results in iontophoresis across the skin. The frequency of the applied current (e.g., DC or AC) can be of any useful range, such as from about 1 Hz to 1000 Hz (e.g., for DC). For AC, the frequency can be, e.g., from about 100 kHz to about 250 kHz.

Further voltage, current, and frequency ranges are described in U.S. Pat. Nos. 5,885,211 and 8,209,006; EP 0027974; EP 1224949 A1; EP 2409727 A1; WO 2012052986; Dujardin et al., J Control Release. 2002 Feb. 19; 79(1-3):219-27; Cevc, Expert Opin Investig Drugs. 1997 December; 6(12):1887-937; Pliquett et al., J Theor Biol. 2008 Mar. 21; 251(2): 195-201; and Prausnitz et al., Proc Natl Acad Sci USA. 1993 Nov. 15; 90(22): 10504-10508, each of which is incorporated in its entirety by reference.

Femtosecond Lasers

Femtosecond lasers (e.g., an excimer laser) also allow for non-thermal ablation of tissue. High intensity femtosecond pulses induce non-linear multiphoton absorption, generating free electron emission. As a result, the surface becomes positively charged. An intense electrical field results in the distribution of negative and positive charges and pulls positive ions out of the surface (Coulomb explosion). The local temperature rise is negligible.

In one embodiment, a femtosecond laser may be used to ablate a tissue portion from a skin region. The ablation depth of femtosecond lasers is in the nanometer to micrometer range for a pulse train. This allows for very accurate control of the total ablation depth. Therefore, the ablation occurs slowly with each pulse, forming an ablated tissue portion with highly controlled dimensions. The femtosecond laser provides non-thermal ablation and does not transfer thermal energy to the surrounding tissue. The tissue may be compressed to improve healing and tighten the skin using methods similar to methods used for surgically excised tissue.

The laser can have any useful parameter for ablation, including wavelength, pulse energy, intensity, or pulse duration. Exemplary non-limiting lasers and related wavelengths (in nm) include argon (488-514 nm), intense pulse light (500-1200 nm), dye (540 nm or 570-640 nm), copper (510 or 578 nm), krypton (416, 531, 568, 752, or 800 nm), KTP/diode (532 nm), diode (800, 940, 980, or 1450 nm, such as DPSS (diode pumped solid state)), Nd:YAG (1064, 1320, 1440, or 1550 nm), Nd:YVO$_4$ (1064 nm), Nd:YLF (1047 or 1053 nm), Er:YAG (1550 or 2940 nm), Er:glass (1540 nm), thulium (1927 nm), Er:YSGG (2780 nm), holmium (2100 nm), CO$_2$ (10600 nm), ruby (694 nm), and alexandrite (755 nm), as well as combinations thereof. In some embodiments, the beam of radiation can have a wavelength from about 380 nm to about 2600 nm (e.g., from 1200 nm to 2600 nm, from 1200 nm to 1800 nm, or from 1300 nm to 1600 nm). In other embodiments, the beam of radiation can have a wavelength of about 1500 nm, 2100 nm, or 2200 nm. In yet other embodiments, the laser is an excimer laser (e.g., an excimer of any one of the following molecules and associated wavelength: $Ar_2$ (126 nm), $Kr_2$ (146 nm), $Xe_2$ (172 and 175 nm), ArF (193 nm), KrF (248 nm), XeBr (282 nm), XeCl (308 nm), XeF (351 nm), or KrCl (222 nm)).

In various non-limiting embodiments, a particular penetration depth of light into the skin (and a corresponding depth of ablation) can be targeted by selecting a wavelength of a beam of radiation. For example, a water absorption coefficient [μa] can be taken from G. M. Hale and M. R. Querry, "Optical constants of water in the 200 nm to 200 μm wavelength region," Appl. Opt., 12, 555-563, (1973) and an Optical Penetration Depth (OPD) can be calculated using a diffusion approximation. The μa of skin is taken as μa of water multiplied by 0.7, and the product of scattering coefficient is taken as 12 $cm^{-1}$. Exemplary wavelengths (in nm) and related optical penetration depths (in mm) include, without limitation, 1180 nm (1.9 mm), 1240 nm (2.07 mm), 1300 nm (1.83 mm), 1340 nm (1.40 mm), 1360 nm (1.11 mm), 1400 (0.43 mm), 1540 nm (0.45 mm), 1640 nm (0.79 mm), 1780 nm (0.58 mm), 1880 nm (0.21 mm), 2360 nm (0.18 mm), or 2600 nm (0.05 mm).

Exemplary pulse durations include from about 1 fs and 400 ns (e.g., using Q-switched short pulsed Nd:YAG laser) or from about 0.1 ms to about 500 ms (e.g., millisecond long pulsed Nd:YAG laser energy). Exemplary fluence (or intensity) includes from about 0.1 $J/cm^2$ to about 300 $J/cm^2$ (e.g., from 0.1 $J/cm^2$ to 5 $J/cm^2$, 0.1 $J/cm^2$ to 10 $J/cm^2$, 0.1 $J/cm^2$ to 25 $J/cm^2$, 0.1 $J/cm^2$ to 50 $J/cm^2$, 0.1 $J/cm^2$ to 100 $J/cm^2$, 0.1 $J/cm^2$ to 150 $J/cm^2$, 0.1 $J/cm^2$ to 200 $J/cm^2$, 0.1 $J/cm^2$ to 250 $J/cm^2$, 0.5 $J/cm^2$ to 5 $J/cm^2$, 0.5 $J/cm^2$ to 10 $J/cm^2$, 0.5 $J/cm^2$ to 25 $J/cm^2$, 0.5 $J/cm^2$ to 50 $J/cm^2$, 0.5 $J/cm^2$ to 100 $J/cm^2$, 0.5 $J/cm^2$ to 150 $J/cm^2$, 0.5 $J/cm^2$ to 200 $J/cm^2$, 0.5 $J/cm^2$ to 250 $J/cm^2$, 0.5 $J/cm^2$ to 300 $J/cm^2$, 1 $J/cm^2$ to 5 $J/cm^2$, 1 $J/cm^2$ to 10 $J/cm^2$, 1 $J/cm^2$ to 25 $J/cm^2$, 1 $J/cm^2$ to 50 $J/cm^2$, 1 $J/cm^2$ to 100 $J/cm^2$, 1 $J/cm^2$ to 150 $J/cm^2$, 1 $J/cm^2$ to 200 $J/cm^2$, 1 $J/cm^2$ to 250 $J/cm^2$, 1 $J/cm^2$ to 300 $J/cm^2$, 1.5 $J/cm^2$ to 5 $J/cm^2$, 1.5 $J/cm^2$ to 10 $J/cm^2$, 1.5 $J/cm^2$ to 25 $J/cm^2$, 1.5 $J/cm^2$ to 50 $J/cm^2$, 1.5 $J/cm^2$ to 100 $J/cm^2$, 1.5 $J/cm^2$ to 150 $J/cm^2$, 1.5 $J/cm^2$ to 200 $J/cm^2$, 1.5 $J/cm^2$ to 250 $J/cm^2$, 1.5 $J/cm^2$ to 300 $J/cm^2$, 2 $J/cm^2$ to 5 $J/cm^2$, 2 $J/cm^2$ to 10 $J/cm^2$, 2 $J/cm^2$ to 25 $J/cm^2$, 2 $J/cm^2$ to 50 $J/cm^2$, 2 $J/cm^2$ to 100 $J/cm^2$, 2 $J/cm^2$ to 150 $J/cm^2$, 2 $J/cm^2$ to 200 $J/cm^2$, 2 $J/cm^2$ to 250 $J/cm^2$, 2 $J/cm^2$ to 300 $J/cm^2$, 3 $J/cm^2$ to 5 $J/cm^2$, 3 $J/cm^2$ to 10 $J/cm^2$, 3 $J/cm^2$ to 25 $J/cm^2$, 3 $J/cm^2$ to 50 $J/cm^2$, 3 $J/cm^2$ to 100 $J/cm^2$, 3 $J/cm^2$ to 150 $J/cm^2$, 3 $J/cm^2$ to 200 $J/cm^2$, 3 $J/cm^2$ to 250 $J/cm^2$, 3 $J/cm^2$ to 300 $J/cm^2$, 5 $J/cm^2$ to 10 $J/cm^2$, 5 $J/cm^2$ to 25 $J/cm^2$, 5 $J/cm^2$ to 50 $J/cm^2$, 5 $J/cm^2$ to 100 $J/cm^2$, 5 $J/cm^2$ to 150 $J/cm^2$, 5 $J/cm^2$ to 200 $J/cm^2$, 5 $J/cm^2$ to 250 $J/cm^2$, or 5 $J/cm^2$ to 300 $J/cm^2$). As wavelength between about 380 nm and about 2600 nm is absorbed by water and skin is about 70% water, the absorption coefficient of skin can be approximated as 70% of the absorption coefficient of water. Further, as the absorption coefficient of water is a function of the wavelength of radiation, the desired fluence depends on the chosen wavelength of radiation, as can be determined by a skilled artisan. For example, for short pulses of radiation, the fluence can be, e.g., in a range of between about 0.1 $J/cm^2$ to about 10 $J/cm^2$, and more preferably between about 1.5 $J/cm^2$ to about 5 $J/cm^2$.

The pulse energy can be, e.g., from about 0.01 J to about 5 J (e.g., from 0.01 J to 0.05 J, 0.01 J to 0.1 J, 0.01 J to 0.5 J, 0.01 J to 1 J, 0.01 J to 2 J, 0.01 J to 3 J, 0.01 J to 4 J, 0.05 J to 0.1 J, 0.05 J to 0.5 J, 0.05 J to 1 J, 0.05 J to 2 J, 0.05 J to 3 J, 0.05 J to 4 J, 0.05 J to 5 J, 0.1 J to 0.5 J, 0.1 J to 1 J, 0.1 J to 2 J, 0.1 J to 3 J, 0.1 J to 4 J, 0.1 J to 5 J, 0.5 J to 1 J, 0.5 J to 2 J, 0.5 J to 3 J, 0.5 J to 4 J, 0.5 J to 5 J, 1 J to 2 J, 1 J to 3 J, 1 J to 4 J, 1 J to 5 J, 1.5 J to 2 J, 1.5 J to 3 J, 1.5 J to 4 J, or 1.5 J to 5 J). In other embodiments, about 12 J of energy is delivered to a skin section of 0.8 $cm^2$ in one second.

Non-limiting exemplary protocols include the following: a pulse duration of about 10 ns, pulse energy of 1.2 J, beam cross sectional area of about 0.8 $cm^2$, and repetition rate of about 1-10 Hz for an alexandrite laser (755 nm with a beam cross sectional area of about 0.5 $cm^2$); a pulse duration of about 10 ns, a beam diameter of about 10 mm, and a beam pulse fluence of about 2 $J/cm^2$; a 10 mm diameter beam at a beam pulse energy density, or fluence, of about 1 $J/cm^2$, using a 10 ns pulse at a frequency of 10 pulses per minute with a ruby laser (694 nm); a beam diameter of about 8-12 mm (e.g., about 8 mm), fluence of about 0.1 $J/cm^2$ to about 10 $J/cm^2$ (e.g., about 3 $J/cm^2$), pulse duration of about 5 ns to about 50 ns (e.g., about 10 ns) with a Q-switched Nd:YAG laser (1064 nm); light with wavelengths of between about 400 nm and about 1500 nm (e.g., between about 600 nm and about 1300 nm) having a pulse duration between about 100 μs and about 200 ms (e.g., in the range of about 10 ms to about 100 ms) and a beam diameter of about 8 mm to about 12 mm; a titanium sapphire near-infrared laser (e.g., a Coherent Radiation Mira Titanium Sapphire mode-locked laser) emitting 200 fsec pulses with a 76 MHz repetition rate, which can be pumped by an argon ion laser operated at 12 watts in a multi-line mode, where optionally, the method of pumping a pulsed laser could be performed according to any of the generally accepted methodologies, including but not limited to, single or multi-line optical pumping, electrical pumping or chemical pumping; a laser having an operating wavelength of 780 nm using a beam scanning system used in confocal microscopy over a tissue region (95 $μm^2$) having a dwell time of tens of microseconds at each of the approximately 250,000 pixels in the scan (the entire scan time being 5-20 seconds) and power between 10 to 30 mwatts (e.g., about 20 mwatts); a pulse duration of about 10 to 30 ns a pulse repetition rate between about 8 and 100 Hz with an excimer laser (e.g., having power between 20 and 100 mW); or a pulse duration of about 100 ms, a beam cross section of 0.8 $cm^2$, a repetition rate of up to about 5 HZ, and a pulse intensity or fluence of about 80 $J/cm^2$ with a long pulse alexandrite laser (755 nm), where each protocol can optionally include a layer of particles (e.g., carbon particles) on the skin. Exemplary protocols and parameters are described in U.S. Pub. No. 20120253333; U.S. Pat. Nos. 8,435,791 and 8,246,611; WO 2012135828; and WO 1999029243, each of which is incorporated by reference in its entirety.

Direct Vacuum Ablation

In yet another embodiment of the invention, penetrating components that are joined to a source of an extremely high vacuum may be brought into contact with a tissue. The high level of vacuum is sufficient to remove tissue through either a suctioning mechanism or through conveyance of damage to the tissue that is targeted for removal or destruction. In one embodiment, a hollow coring needle or another penetrating component, configured to connect an external tissue portion to the vacuum inside (e.g., a hollow coring needle or a needle with side-holes or slots, thereby allowing for connection tissue along the long axis of the needle), may be inserted into a skin region. A vacuum is applied (e.g., a vacuum with an absolute pressure less than about 6.3 kPa or any ranges described herein), and tissue adjacent to the needle is damaged by the vacuum. The size of an ablated tissue portion may be controlled by the level of vacuum and the duration of exposure. In one embodiment, vacuum can ablate tissue by causing local boiling off or vaporization of tissue at ambient temperatures. In another embodiment, vacuum can ablate tissue by causing desiccation or freeze-drying of tissue.

Ultrasound Ablation

In yet another embodiment of the invention, penetrating components that are joined to a source of a high intensity ultrasound wave may be bought into contact with a tissue. The high intensity of ultrasound wave conducts vibrational energy, which is sufficient to cause cellular and tissue disruption. In one embodiment, a needle or another penetrating component configured to connect to an external tissue portion to the ultrasound wave may be inserted into a skin region. An ultrasound wave is applied (e.g., an ultrasound wave with a frequency greater than about 20 kHz) and tissue, either in direct contact with the needle or in proximity of the needle, is damaged by the ultrasound wave. The size of an ablated tissue portion may be controlled by the intensity of ultrasound wave and the duration of exposure. In one embodiment, ultrasound can ablate tissue by causing liquefaction of the tissue. Liquefied tissue may be removed either by squeezing the tissue or by using an absorbent tool or material (e.g., a straw).

Ablation Apparatus Arrays

The ablation apparatuses described herein may be assembled into arrays of ablation apparatuses to facilitate skin treatment over larger areas and in less time. An array may contain a homogeneous set of ablation apparatuses (e.g., all the apparatuses are identical square blades) or the array may contain a heterogeneous array of ablation apparatuses (e.g., a mixture of blade geometries or a mixture of cryoprobes and blades). The ablation apparatus array may include one or more tissue removal apparatuses or tissue positioning apparatuses. The ablation apparatus array may be included in a device which allows for an improved user interface, including sensors, therapeutic agents, guides, and sanitizing/cleaning features.

The apparatuses for making ablations (e.g., drill, blades, probe and/or tubes) can be provided in any useful arrangement (e.g., a linear array, a radial array, or any described herein) of one or more components (e.g., two, three, four, five, ten, thirty, fifty, hundred, or more). The spacing between each ablation apparatus (e.g., drill, blade and/or tube) can be of any useful dimension, such as between about 0.5 mm and 50 mm (e.g., between about 1 mm and 40 mm, 1 mm and 30 mm, 1 mm and 25 mm, 1 mm and 20 mm, 1 mm and 15 mm, 1 mm and 10 mm, 1 mm and 5 mm, 1 mm and 3 mm, 3 mm and 50 mm, 3 mm and 40 mm, 3 mm and 30 mm, 3 mm and 25 mm, 3 mm and 20 mm, 3 mm and 15 mm, 3 mm and 10 mm, 3 mm and 5 mm, 5 mm and 50 mm, 5 mm and 40 mm, 5 mm and 30 mm, 5 mm and 25 mm, 5 mm and 20 mm, 5 mm and 15 mm, 5 mm and 10 mm, 10 mm and 50 mm, 10 mm and 40 mm, 10 mm and 30 mm, 10 mm and 25 mm, 10 mm and 20 mm, 10 mm and 15 mm, 15 mm and 50 mm, 15 mm and 40 mm, 15 mm and 30 mm, 15 mm and 25 mm, 15 mm and 20 mm, 20 mm and 50 mm, 20 mm and 40 mm, 20 mm and 30 mm, 20 mm and 25 mm, 30 mm and 50 mm, 30 mm and 40 mm, or 40 mm and 50 mm).

Such arrangements can include one or more ablation apparatuses (e.g., about 2, 3, 4, 5, 6, 7, 8, 9, 10, 15, 20, 25, 30, 35, 40, 45, 50, 75, 100, or more ablation apparatuses, such as between about 2 and 100 ablation apparatuses (e.g., between 2 and 10, 2 and 15, 2 and 20, 2 and 25, 2 and 30, 2 and 35, 2 and 40, 2 and 45, 2 and 50, 2 and 75, 5 and 10, 5 and 15, 5 and 20, 5 and 25, 5 and 30, 5 and 35, 5 and 40, 5 and 45, 5 and 50, 5 and 75, 5 and 100, 10 and 20, 10 and 25, 10 and 30, 10 and 35, 10 and 40, 10 and 45, 10 and 50, 10 and 75, 10 and 100, 15 and 20, 15 and 25, 15 and 30, 15 and 35, 15 and 40, 15 and 45, 15 and 50, 15 and 75, 15 and 100, 20 and 25, 20 and 30, 20 and 35, 20 and 40, 20 and 45, 20 and 50, 20 and 75, 20 and 100, 25 and 30, 25 and 35, 25 and 40, 25 and 45, 25 and 50, 25 and 75, 25 and 100, 30 and 35, 30 and 40, 30 and 45, 30 and 50, 30 and 75, 30 and 100, 35 and 40, 35 and 45, 35 and 50, 35 and 75, 35 and 100, 40 and 45, 40 and 50, 40 and 75, 40 and 100, 50 and 75, or 50 and 100)).

Such arrangements of ablation apparatuses can be any of various two-dimensional or three-dimensional patterns along a base holding one or more components for making ablations (e.g., blades and/or tubes). The base can be optionally mounted on a roller apparatus having a cylindrical body with a longitudinal rotational axis, where the one or more blades and/or tubes are arranged on the longitudinal surface of the cylindrical body. In some embodiments, the blade or tube extends as substantially coplanar extensions of the cylindrical body. In use, rotation of the cylindrical body along the skin results in the ablation of tissue portions by the ablation apparatuses. Exemplary roller apparatuses are provided in FIGS. 11A-11B and its associated text in U.S. Pub. No. 2011/0251602, in FIGS. 3A-3B and its associated text in International Pub. No. WO 2012/103492, which are hereby incorporated by reference in its entirety.

Additional Components

Any of the devices, apparatuses, and methods herein can be integrated with other useful components. For instance, an ablation apparatus including a drill bit could benefit from use with a cryosource, such as to cool the skin prior to drilling. Accordingly, this ablation apparatus can include a cryosource, such as any described herein. In a similar manner, any of the apparatuses herein (e.g., an ablation apparatus) can include one or more of a cryosource, a vacuum, a motor, a generator, an insulator, and/or a sensor.

Another additional component is an alignment feature. In devices of the invention that combine an ablation apparatus with a tissue removal or tissue positioning apparatus, an aligning feature may provide a means to ensure the ablated tissue portion is removed correctly (e.g., the tissue removal apparatus is aligned with the ablated tissue portions) or to ensure the skin region is flat prior to ablation (e.g., the tissue positioning apparatus holds the skin region in a flat position under tension).

Removal Apparatuses and Methods for Removing Tissue

Mechanical or Physical Methods

An ablated tissue portion may require removal from a skin region or an ablation apparatus of the invention. For example, an ablated tissue portion may be captured in a hollow micro-coring needle, a micro-coring paper drill, a micro-coring hole saw, or a micro-coring blade array. After capture, the ablation apparatus (e.g., the hollow micro-coring needle, micro-coring paper drill, micro-coring hole saw, or micro-coring blade array) may be removed from the skin region, but the ablated tissue portion still lodged inside the ablation apparatus. The ablated tissue portion needs to be removed in order to continue the skin treatment procedure. In one embodiment, a pin may be inserted from one side to the ablation apparatus and used to push out the ablated tissue portion. In another embodiment, the tissue may be pushed out using compressed air or a pressurized fluid.

In another embodiment, a separate tool may be used to remove the ablated tissue portion from the skin region. For example, micro-tweezers may be used to pull tissue out of an ablated tissue portion or hole. In another embodiment, the tissue removal apparatus may be configured with a surface that adheres to the ablated tissue. When the tissue removal apparatus is removed, the ablated tissue is pulled out of the holes. In one embodiment, the removal apparatus is configured with a flexible support layer attached to an adhesive layer (e.g., tape). The apparatus is applied on the skin region. The tissue removal device adheres to the ablated tissue as well as to the surrounding skin region. When the tissue removal apparatus is lifted from the skin, the ablated tissue portion is pulled out of the holes and the adhesion between the apparatus and the surrounding tissue is broken. In another embodiment, an array of probes is attached to the tissue removal apparatus and the probes are applied to the skin region. The probes are aligned to be placed in contact with the ablated tissue portions. The probe may be constituted of a rigid cylinder in which the bottom surface is covered with an adhesive. Alternatively, the probe may be configured with a cold probe that adheres to the skin due to low temperature. The probes may be combined with the surgical cutting mechanism or ablation apparatus.

In another embodiment, an ablated tissue portion may be removed by applying a compressive force on the treatment area to squeeze the tissue out of the skin region. The compressive force can be applied by the fingers of the physician performing the ablation or by a tool, apparatus or device applying a controlled compressive force to the treatment area.

Vacuum

In one embodiment, a tissue removal apparatus with a vacuum may be applied to an ablation apparatus or a skin region after formation of an ablated tissue portion. For example, a tissue removal apparatus may be configured with an array of small access ports along the bottom of the chamber which may be applied to a skin region. The access ports that contact an ablated tissue portion may form a seal with the tissue. Upon separation of the tissue removal apparatus from the skin region, the ablated tissue portions are also removed.

In one embodiment, vacuum can ablate tissue by causing local boiling off or vaporization of tissue at ambient temperatures. In another embodiment, a vacuum is applied to micro-coring needle(s) or to circular blade(s) to facilitate detachment and removal of the tissue after insertion of the ablating member through the skin.

Thermal Removal

Thermal ablation can be used to remove an ablated tissue portion when the tissue portion is thermally isolated (e.g., ablated tissue or tissue for removal is surrounded by a thermal insulating material) from the surrounding tissue. In one embodiment, a micro-coring member (e.g. micro-coring needles, micro-coring paper drill, micro-coring hole saw, or micro-coring blade assembly) may be inserted in the skin to ablate and circumscribe the tissue without generation of thermal injury. While the micro-coring member is still in the skin, an ablative laser may be used to vaporize the tissue contained in the micro-coring member. The micro-coring apparatus material may be chosen to act as a thermal insulator to prevent heating of the tissue outside of the micro-coring apparatus. In additional embodiments, any form of thermal ablation may be used to remove a thermally isolated ablated tissue portion. For example and without limitation, any other method to convey heat in a shielded configuration may also work, such as use of a heated inner core needle, radiofrequency, ultrasound, and/or microscale application of a hot liquid or gas.

Resorption

Denatured tissue may also be resorbed in a skin region and replaced by newly formed tissue. In an exemplary embodiment, an ablated tissue portion may be formed using a cryoneedle. The cryoneedle is removed and a compressive force is applied to the surrounding tissue, including the ablated tissue portion. A dressing or closure may be applied to sustain the compressive force. The ablated or damaged tissue from the cryosurgery may be resorbed thus allowing for the growth of new tissue. In another embodiment, an ablated tissue portion is desiccated (e.g., water removed) using a strong vacuum. The desiccated tissue may then be resorbed in the skin region and be replaced by newly formed tissue. In yet another embodiment, the tissue might not be compressed after exposure to cold temperature, which can optionally lead to improved tissue texture and appearance without significant tissue tightening Liquefaction Another apparatus and method for tissue removal includes liquefying the tissue with mechanical means. In one embodiment, a thin wire frame or grid may be moved rapidly around an ablated tissue portion. The rapid and continuous cutting of the tissue eventually forms a liquid or gel from the ablated tissue portion. The tissue may be removed or drawn away by vacuum. Another embodiment includes the use of a wire or fiber that may be attached to an axle and then rotated at or otherwise moved at a high speed to liquefy an ablated tissue portion. A pile driver, as described herein, can cause liquefaction of tissue.

Positioning Apparatuses and Methods for Positioning Tissue

Holding tissue in place prior to, during or after ablation, and/or tissue removal may be more difficult when treating very lax tissue. Tissue positioning apparatuses of the invention facilitate ablation and tissue removal and also reduce errors in the skin treatment procedure. A skin positing apparatus may provide a compressive force and/or may be used to hold the skin in a desired xy dimension or lift the skin to elevate the dermis away from the underlying structures (e.g., sub-dermal muscle layer, blood vessels, and nerve fibers) and prevent injuries to these structures. Tissue positioning apparatuses may be combined with an ablation apparatus and/or a tissue removal apparatus.

Tensioning

Surgeons put tissue under tension with their fingers before creating an incision with a scalpel. Prior to fractional ablation or tissue removal, the tissue may be placed under tension and/or provided as a flat surface, which can be important for improving treatment outcome. In one embodiment, two parallel rigid rods are applied on the skin. The rod material is chosen to maximize its friction coefficient with the skin (e.g., rubber). The rods are first pushed toward the skin and then away from each other in order to apply a tension on the skin surface. The skin region between the rods essentially becomes planar. The formation of a flat surface allows for accurate positioning of an ablation apparatus above the skin region. When the ablation apparatus is an array of ablation apparatuses, the flat skin region allows for co-planar positioning (e.g., x-y positioning) of the array. The skin region under tension facilitates the insertion of the penetrating components of an ablation apparatus (e.g., a needle, drill, wire, or blade) into the tissue. The rods can rotate while maintaining the skin under tension to allow displacement of the ablation array. Another embodiment includes the use of micro-hooks or micro-barbs to maintain tension in the skin region. The micro-hooks are put under tension to flatten the skin in the treatment area.

Figure 22:
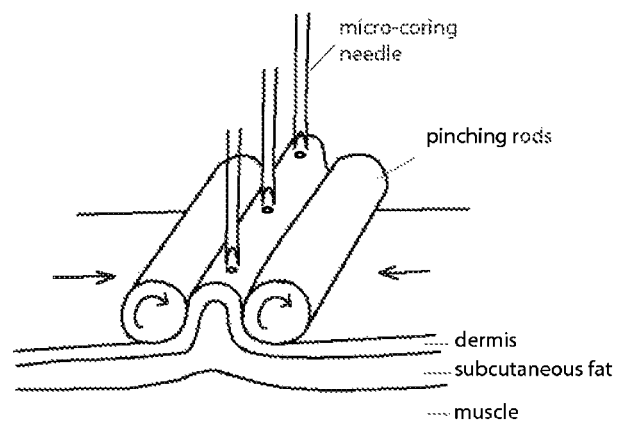
FIG. 22 shows an exemplary tissue positioning apparatus including two cylindrical pinching rods to provide tension (e.g., a compressive force applied across the skin, indicated by arrows) to a tissue area. The application of tension to the skin region may provide a protruded surface region of the skin in which the dermis is lifted from underlying layers (e.g., subcutaneous fat and muscle), for skin treatment using micro-corning needles placed between the pinching rods.

In yet another embodiment, instead of pulling the rods away from each other, the rods can be pushed or rotated towards each other to pinch the skin and to exert a compressive force across the skin to elevate the dermis away from the underlying structures (e.g., sub-dermal muscle layer, blood vessels, and nerve fibers) (FIG. 22). A linear array of micro-coring needles may be placed in between the rods, which can be rotated towards each other and allow movement of the apparatus across the skin surface to be treated. The control of the rotation angle of the rods allows control of the displacement of the treatment mechanism and the treatment coverage. In this embodiment, using the rods to pinch the skin allows displacement of the treatment mechanism without releasing the skin, thus, increasing treatment speed and allowing better control of the treatment coverage.

Figure 23:
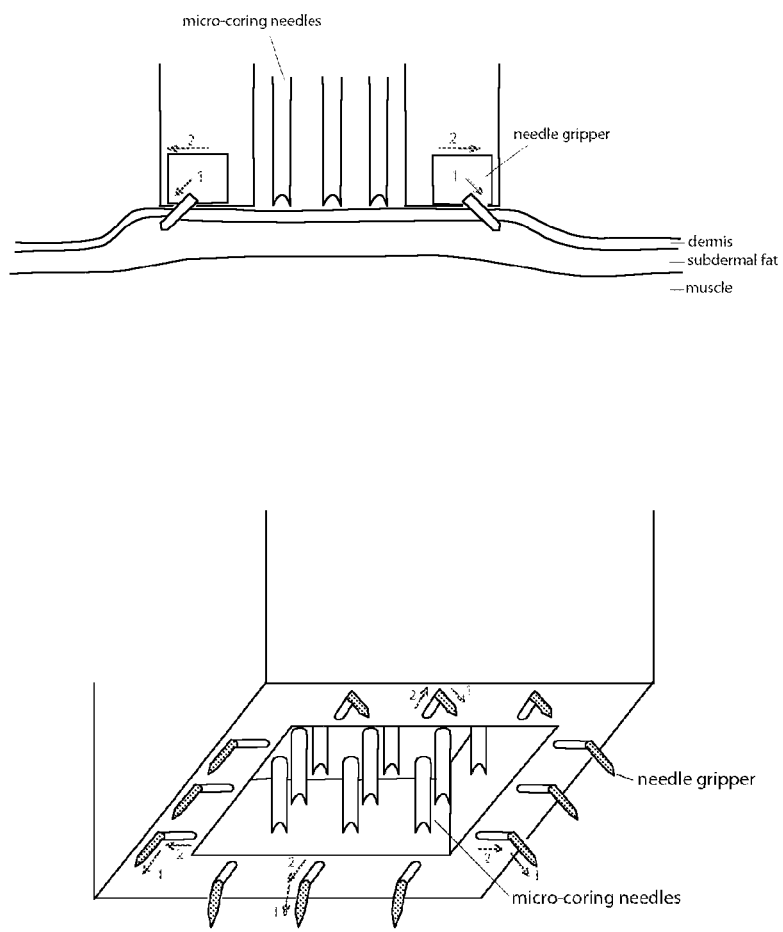
FIG. 23 shows an exemplary tissue positioning apparatus having a series of needles ("needle grippers") that surround micro-corning needles to attach and hold tension (e.g., a gripping force) in a tissue or skin region. The needle grippers may be inserted in the skin (arrow 1) and pulled (arrow 2) to provide tension to the skin and lift the dermis from underlying skin layers. Top figure provides a side-view and bottom figure provides a top-view of the apparatus.

In another embodiment, needles that provide a gripping force ("needle grippers") may be deployed in the dermis layer to lift the skin and elevate the dermis away from the underlying structures (e.g., sub-dermal muscle layer, blood vessels, and nerve fibers). Once inserted in the skin (FIG. 23, arrow 1), opposite needles may be pulled away (FIG. 23, arrow 2) from each other to generate skin tension. The needles can then be pulled away from the skin surface to create a displacement of the dermis away from the underlying structures to prevent injury to muscle, blood vessels, and nerve fibers by the micro-coring needles. The level of skin tension may be adjusted by pulling opposite needles away from each other in one direction to create a unidirectional skin tension. The needles may be retracted to release the skin. Needle grippers work on wet skin (i.e., when skin is covered with a liquid (e.g., blood)) and on partially treated skin (i.e. surface already punctured by micro-coring needles).

In another embodiment, a flat surface with at least a hole is applied on the skin, and the applied member is pushed towards the skin. The hole(s) in the surface allow access to the skin to the ablation member(s). For example and without limitation, one can envision a circular surface of 3-4 cm in diameter with a hole in its center of 5 mm-1 cm. The circular member is applied on the skin and pushed towards the skin as to put the skin exposed through the central hole under tension. The ablation member(s) (e.g., one or more needles) are then positioned on top of the central hole and pushed through the skin.

In some embodiments, small non-circular holes are generated to promote wound healing. For example, pre-stretching the skin before ablation with a circular coring needle generates an elliptical hole in a non-stretched skin, such as when the skin is once again relaxed. The long axis of the ellipse is perpendicular to the pre-stretching direction. An elliptical hole will generate skin tightening preferentially in the direction of the short axis of the ellipse.

In order to provide a tissue in a planar area positioned and under tension, a force may be provided to a skin region. A compression (or compressive force, e.g., lateral compression), expansion (e.g., lateral expansion), tension (e.g., as measured by tensile stress), stress (e.g., as measured by compressive stress, shear stress, or tensile stress), load (e.g., load per millimeter width of at least 0.1 Newtons at a strain of at least 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or higher), or strain (e.g., as measured by deflection, deformation, strain at failure, or ultimate strain (extension before rupture), e.g., greater than about 30% (e.g., greater than about 40%, 50%, 60%, 70%, 75%, 80%, 90%, 95%, 100%, 110%, 115%, or 120%) or from about 30% to 130%) may be to be applied to the skin region.

Vacuum

Vacuum may be used to pull lax skin under tension and pre-position a skin region prior to fractional ablation. In one embodiment, a tube with a diameter large enough to surround an ablation apparatus or array of ablation apparatuses may be positioned on a skin region. A vacuum is applied to the tube. As a result, the skin is pulled toward the tube opening. The skin surface that faces the tube end is under tension and essentially flat. The skin region position is fixed relative to the tube and to the ablation apparatus or array. Another benefit of this embodiment is that the vacuum provides high gripping force and pulls the epidermal and dermal layer away from underlying structures (e.g. blood vessels, nerve fibers, muscle). Without wishing to be limited by mechanism, use of vacuum could decrease the risk of collateral damage should the ablation be too deep. In a further benefit of this embodiment, the vacuum approach works to pull skin under tension even when skin is wet (e.g., when skin is covered with a liquid (e.g., blood)). Further, the vacuum may be used to pull the skin towards the fractional ablation tool (instead of lowering the tool towards the skin).

Airflow

A tissue positioning apparatus may alternatively include grippers that use airflow to adhere to the skin without physical contact. In one embodiment, a gripper may use Bernoulli airflow ("a Bernoulli gripper") to position the skin. A Bernoulli gripper relies on a pressurized air jet that generates a sub-atmospheric pressure of a radial airflow in a small gap between the skin and the gripper (Dini et al., *CIRP Annals—Manufacturing Tech.* 58:21-24, 2009), thus creating a vacuum-like effect without the use of a vacuum. One of the benefits of the Bernoulli gripper is that it does not contact the skin. Without wishing to be limited by mechanism, use of Bernoulli airflow could limit the risk of contamination. In another embodiment, a gripper may use the Coanda ejector ("a Coanda gripper") to position the skin. The Coanda ejector generates a gripping force by deflection of a pressurized airflow (Lien et al., *CIRP Annals—Manufacturing Tech.* 57:33-36, 2008). A Coanda gripper may include an array of Coanda ejectors, which can position the skin by suction.

Cold Temperature

Cold objects adhere to the skin by freezing to the moisture from the tissue. A tissue positioning apparatus may include a cold surface that may be applied to the skin of the patient (e.g., a metal material at, for example, about −10 degrees C.). The tissue positioning apparatus may also include a series of channels through the cold surface to provide access to an ablation apparatus of a skin region. Tension may be applied on the positioning device to lift the epidermal and dermal layer away from underlying tissues prior to ablation. The cold temperature also reduces pain perception by the patient. To release the skin from the freeze gripper, the skin can be mechanically detached from the gripper, e.g., by a "knife" mechanism introduced between the gripper and the skin. A benefit of the freeze gripper is that the freeze gripper works to pull skin under tension even when skin is wet (e.g., when skin is covered with a liquid (e.g., blood)) or when skin is partially treated by mechanical fractional ablation.

Adhesive

In a further embodiment, tissue can be positioned using an apparatus that includes an adhesive to hold a skin region. The adhesive may be on a surface of the device or on features attached to the device. In one embodiment, a tissue positioning apparatus having an adhesive surface and a series of channels configured to accept an array of ablation apparatuses may be used to position a skin region by adhering to the skin region after being put under tension. The adhesive surface joins with the skin region, thus maintaining the tension and providing a flat skin region. An array of ablation apparatuses may be moved through the access ports and used to ablate the tissue of the skin region.

Sensing

When the positioning and/or tensioning feature is integrated in the fractional ablation device, i.e. the device both allows positioning of the skin and tissue removal, it may be advantageous to have a mechanism that ensures that the ablation apparatus is appropriately positioned before activation of the fractional ablation. One can envision a number of sensing modalities including: a mechanical sensor (switch) that is activated when the device presses on the skin, a temperature sensor that detects a temperature increase when the device is applied to the skin surface, an optical sensor that detects skin proximity or microcontours or ablations (e.g., to avoid overstrikes and/or to promote control of spacing of ablations), or an inductive sensor that senses changes in inductive coupling due to the presence of electrically conductive skin.

The sensor can also be continuously monitored during the treatment to ensure appropriate positioning of the device. The device may be stopped when the sensor detects that the skin is not in contact with the device.

Exemplary Ablation Devices

An ablation apparatus, tissue removal apparatus, and tissue position apparatus may be configured into a single device. Such a device provides several benefits, including ease of use, less time for the procedure, less time between ablation and closing of the ablated tissue portion, and more robust removal of ablated tissue portions. In one embodiment, an ablation apparatus is coupled into a device with a tissue removal apparatus using vacuum. The vacuum can be isolated from the device during the ablation. After the ablation (e.g., drilling of a tissue portion to form a hole), the vacuum source may be joined to the device and the vacuum ports positioned over the drill holes to remove tissue and debris, thus completing the formation of an ablated tissue portion. In another embodiment, the tissue removal apparatus is configured to also be a tissue positioning apparatus, both using vacuum. In this embodiment, the ablation apparatus (e.g., a drill), tissue positioning apparatus, and tissue removal apparatus form a device which may be joined to a vacuum apparatus configured to supply vacuum in two geometries (e.g., a first vacuum geometry for positioning tissue and a second vacuum, geometry for removing tissue). Prior to ablation, the vacuum source is joined to the tissue positioning configuration in the device and the skin region placed under tension. The device is brought into contact with the skin region and the tissue is held in a planar position by the first vacuum geometry. The ablation component of the device is aligned and the drill enters the tissue to form holes. After drilling, the second vacuum geometry is connected to the vacuum source, thus removing tissue and debris from the ablated tissue portions. Finally, the vacuum source is removed from the device releasing the skin region from the positioning component of the device.

Healing of Skin Regions after Removal of Ablated Tissue Portions

A compressive wound dressing may be applied after ablation and subsequent compression leads to skin tightening. The ablated tissue portion may be closed with a suture, staple, dressing, tunable dressing, glue, sealant, and other compression retaining devices. Such dressings may be applied in the proximity of the treatment zone or at a distant site provided that it conveys the appropriate mechanical force on the treatment site (e.g., by gluing the surrounding area into a compressed state, which then confers compression to the treated area).

In one exemplary technique, a photosensitizer is applied to the tissue (e.g., Rose Bengal (RB) at concentration of less than 1.0% weight per volume in a buffer, e.g., phosphate buffered saline to form a skin tissue-RB complex), and then the tissue is irradiated with electromagnetic energy to produce a seal (e.g., irradiated at a wavelength of at least 488, at less than 2000 J/cm$^2$, and/or less than 1.5 W/cm$^2$, e.g., about 0.6 W/cm$^2$). This exemplary technique is described in U.S. Pat. No. 7,073,510, which is incorporated by reference in its entirety. In another exemplary technique, a laser can be used for tissue welding. In yet another exemplary technique, a photochemical agent is applied to the tissue, and then the tissue is irradiated with visible light to produce a seal. In any of these embodiments, the technique includes use of a bioerodible, unstable material that degrades spontaneously or in reaction to a treatment (e.g., such as any resorbable or biodegradable material, including any described herein).

Materials

The methods, devices and apparatuses of the invention can include any useful materials.

Polymers and Plastics

An ablation apparatus, tissue removal apparatus, or tissue positioning apparatus may be formed from any useful polymer or plastic. Exemplary polymers and plastics include, e.g., alginate, benzyl hyaluronate, carboxymethylcellulose, cellulose acetate, chitosan, collagen, dextran, epoxy, gelatin, hyaluronic acid, hydrocolloids, nylon (e.g., nylon 6 or PA6), pectin, poly (3-hydroxyl butyrate-co-poly (3-hydroxyl valerate), polyalkanes, polyalkene, polyalkynes, polyacrylate (PA), polyacrylonitrile (PAN), polybenzimidazole (PBI), polycarbonate (PC), polycaprolactone (PCL), polyester (PE), polyethylene glycol (PEG), polyethylene oxide (PEO), PEO/polycarbonate/polyurethane (PEO/PC/PU), poly(ethylene-co-vinyl acetate) (PEVA), PEVA/polylactic acid (PEVA/PLA), polyethylene, polypropylene, poly (ethylene terephthalate) (PET), PET/poly (ethylene naphthalate) (PET/PEN) polyglactin, polyglycolic acid (PGA), polyglycolic acid/polylactic acid (PGA/PLA), polyimide (PI), polylactic acid (PLA), poly-L-lactide (PLLA), PLLA/PC/polyvinylcarbazole (PLLA/PC/PVCB), poly (β-malic acid)-copolymers (PMLA), polymethacrylate (PMA), poly (methyl methacrylate) (PMMA), polystyrene (PS), polyurethane (PU), poly (vinyl alcohol) (PVA), polyvinylcarbazole (PVCB), polyvinyl chloride (PVC), polyvinylidenedifluoride (PVDF), polyvinylpyrrolidone (PVP), silicone, rayon, polytetrafluoroethylene (PTFE), polyether ether ketone (PEEK), or combinations thereof. The polymer or plastic of the invention may be composite materials in which additives to the plastic, such as ceramics or particles, alter the mechanical properties.

Metals and Metal Alloys

An ablation apparatus, tissue removal apparatus, or tissue positioning apparatus may be formed from any useful metal or metal alloy. Exemplary metals and alloys include stainless steel; titanium; a nickel-titanium (NiTi) alloy; a nickel-titanium-niobium (NiTiNb) alloy; a nickel-iron-gallium (NiFeGa) alloy; a nickel-manganese-gallium (NiMnGa) alloy; a copper-aluminum-nickel (CuAlNi) allow; a copper-zinc (CuZn) alloy; a copper-tin (CuSn) alloy; a copper-zinc-aluminum (CuZnAl) alloy; a copper-zinc-silicon (CuZnSi) alloy; a copper-zinc-tin (CuZnSn) alloy; a copper-manganese alloy; a gold-cadmium (AuCd) alloy; a silver-cadmium (AgCd) alloy; an iron-platinum (FePt) alloy; an iron-manganese-silicon (FeMnSi) alloy; a cobalt-nickel-aluminum (CoNiAl) alloy; a cobalt-nickel-gallium (CoNiGa) alloy; or a titanium-palladium (TiPd) alloy.

Adhesive Materials

A tissue removal apparatus and/or tissue positioning apparatus may use an adhesive. An adhesive may be located on an apparatus surface, the end of a probe, or another surface attached to a tissue removing or tissue positioning apparatus.

The adhesive can be a pressure-sensitive adhesive (PSA). The properties of pressure sensitive adhesives are governed by three parameters, tack (initial adhesion), peel strength (adhesion), and shear strength (cohesion). Pressure-sensitive adhesives can be synthesized in several ways, including solvent-borne, water-borne, and hot-melt methods. Tack is the initial adhesion under slight pressure and short dwell time and depends on the adhesive's ability to wet the contact surface. Peel strength is the force required to remove the PSA from the contact surface. The peel adhesion depends on many factors, including the tack, bonding history (e.g. force, dwell time), and adhesive composition. Shear strength is a measure of the adhesive's resistance to continuous stress. The shear strength is influenced by several parameters, including internal adhesion, cross-linking, and viscoelastic properties of the adhesive. Permanent adhesives are generally resistant to debonding and possess very high peel and shear strength.

Exemplary adhesives include a biocompatible matrix (e.g., those including at least one of collagen (e.g., a collagen sponge), low melting agarose (LMA), polylactic acid (PLA), and/or hyaluronic acid (e.g., hyaluranon); a photosensitizer (e.g., Rose Bengal, riboflavin-5-phosphate (R-5-P), methylene blue (MB), N-hydroxypyridine-2-(1H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); a biologic sealant (e.g., a mixture of riboflavin-5-phosphate and fibrinogen, a fibrin-based sealant, an albumin-based sealant, or a starch-based sealant); or a hook or loop and eye system (e.g., as used for Velcro®). In particular embodiments, the adhesive is biodegradable.

Exemplary pressure-sensitive adhesives include natural rubber, synthetic rubber (e.g., styrene-butadiene and styrene-ethylene copolymers), polyvinyl ether, polyurethane, acrylic, silicones, and ethylene-vinyl acetate copolymers. A copolymer's adhesive properties can be altered by varying the composition (via monomer components) changing the glass transition temperature (Tg) or degree of cross-linking. In general, a copolymer with a lower Tg is less rigid and a copolymer with a higher Tg is more rigid. The tack of PSAs can be altered by the addition of components to alter the viscosity or mechanical properties. Exemplary pressure sensitive adhesives are described in Czech et al., "Pressure-Sensitive Adhesives for Medical Applications," in Wide Spectra of Quality Control, Dr. Isin Akyar (Ed., published by InTech), Chapter 17 (2011), which is hereby incorporated by reference in its entirety.

Therapeutic Agents

The ablation apparatuses and methods of the invention can include one or more useful therapeutic agents. Exemplary agents include one or more growth factors (e.g., vascular endothelial growth factor (VEGF), platelet-derived growth factor (PDGF), transforming growth factor beta (TGF-β), fibroblast growth factor (FGF), epidermal growth factor (EGF), and keratinocyte growth factor); one or more stem cells (e.g., adipose tissue-derived stem cells and/or bone marrow-derived mesenchymal stem cells); one or more skin whitening agents (e.g., hydroquinone); one or more vitamin A derivatives (e.g., tretinoin), one or more analgesics (e.g., paracetamol/acetaminophen, aspirin, a non-steroidal antiinflammatory drug, as described herein, a cyclooxygenase-2-specific inhibitor, as described herein, dextropropoxyphene, co-codamol, an opioid (e.g., morphine, codeine, oxycodone, hydrocodone, dihydromorphine, pethidine, buprenorphine, tramadol, or methadone), fentanyl, procaine, lidocaine, tetracaine, dibucaine, benzocaine, p-butylaminobenzoic acid 2-(diethylamino) ethyl ester HCl, mepivacaine, piperocaine, dyclonine, or venlafaxine); one or more antibiotics (e.g., cephalosporin, bactitracin, polymyxin B sulfate, neomycin, bismuth tribromophenate, or polysporin); one or more antifungals (e.g., nystatin); one or more antiinflammatory agents (e.g., a non-steroidal antiinflammatory drug (NSAID, e.g., ibuprofen, ketoprofen, flurbiprofen, piroxicam, indomethacin, diclofenac, sulindac, naproxen, aspirin, ketorolac, or tacrolimus), a cyclooxygenase-2-specific inhibitor (COX-2 inhibitor, e.g., rofecoxib (Vioxx®), etoricoxib, and celecoxib (Celebrex®)), a glucocorticoid agent, a specific cytokine directed at T lymphocyte function), a steroid (e.g., a corticosteroid, such as a glucocorticoid (e.g., aldosterone, beclometasone, betamethasone, cortisone, deoxycorticosterone acetate, dexamethasone, fludrocortisone acetate, hydrocortisone, methylprednisolone, prednisone, prednisolone, or triamcinolone) or a mineralocorticoid agent (e.g., aldosterone, corticosterone, or deoxycorticosterone)), or an immune selective antiinflammatory derivative (e.g., phenylalanine-glutamine-glycine (FEG) and its D-isomeric form (feG))); one or more antimicrobials (e.g., chlorhexidine gluconate, iodine (e.g., tincture of iodine, povidone-iodine, or Lugol's iodine), or silver, such as silver nitrate (e.g., as a 0.5% solution), silver sulfadiazine (e.g., as a cream), or $Ag^+$ in one or more useful carriers (e.g., an alginate, such as Acticoat® including nanocrystalline silver coating in high density polyethylene, available from Smith & Nephew, London, U.K., or Silvercel® including a mixture of alginate, carboxymethylcellulose, and silver coated nylon fibers, available from Systagenix, Gatwick, U.K.; a foam (e.g., Contreet® Foam including a soft hydrophilic polyurethane foam and silver, available from Coloplast A/S, Humlebæk, Denmark); a hydrocolloid (e.g., Aquacel® Ag including ionic silver and a hydrocolloid, available from Conva Tec Inc., Skillman, N.J.); or a hydrogel (e.g., Silvasorb® including ionic silver, available from Medline Industries Inc., Mansfield, Mass.)); one or more antiseptics (e.g., an alcohol, such as ethanol (e.g., 60-90%), 1-propanol (e.g., 60-70%), as well as mixtures of 2-propanol/isopropanol; boric acid; calcium hypochlorite; hydrogen peroxide; manuka honey and/or methylglyoxal; a phenol (carbolic acid) compound, e.g., sodium 3,5-dibromo-4-hydroxybenzene sulfonate, trichlorophenylmethyl iodosalicyl, or triclosan; a polyhexanide compound, e.g., polyhexamethylene biguanide (PHMB); a quaternary ammonium compound, such as benzalkonium chloride (BAC), benzethonium chloride (BZT), cetyl trimethylammonium bromide (CTMB), cetylpyridinium chloride (CPC), chlorhexidine (e.g., chlorhexidine gluconate), or octenidine (e.g., octenidine dihydrochloride); sodium bicarbonate; sodium chloride; sodium hypochlorite (e.g., optionally in combination with boric acid in Dakin's solution); or a triarylmethane dye (e.g., Brilliant Green)); one or more antiproliferative agents (e.g., sirolimus, tacrolimus, zotarolimus, biolimus, or paclitaxel); one or more emollients; one or more hemostatic agents (e.g., collagen, such as microfibrillar collagen, chitosan, calcium-loaded zeolite, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g., II, V, VII, VIII, IX, X, XI, XIII, or Von Willebrand factor, as well as activated forms thereof), a procoagulant (e.g., propyl gallate), an anti-fibrinolytic agent (e.g., epsilon aminocaproic acid or tranexamic acid), and the like); one or more procoagulative agents (e.g., any hemostatic agent described herein, desmopressin, coagulation factor(s) (e.g., II, V, VII, VIII, IX, X, XI, XIII, or Von Willebrand factor, as well as activated forms thereof), procoagulants (e.g., propyl gallate), antifibrinolytics (e.g., epsilon aminocaproic acid), and the like); one or more anticoagulative agents (e.g., heparin or derivatives thereof, such as low molecular weight heparin, fondaparinux, or idraparinux; an anti-platelet agent, such as aspirin, dipyridamole, ticlopidine, clopidogrel, or prasugrel; a factor Xa inhibitor, such as a direct factor Xa inhibitor, e.g., apixaban or rivaroxaban; a thrombin inhibitor, such as a direct thrombin inhibitor, e.g., argatroban, bivalirudin, dabigatran, hirudin, lepirudin, or ximelagatran; or a coumarin derivative or vitamin K antagonist, such as warfarin (coumadin), acenocoumarol, atromentin, phenindione, or phenprocoumon); one or more immune modulators, including corticosteroids and non-steroidal immune modulators (e.g., NSAIDS, such as any described herein); one or more proteins; or one or more vitamins (e.g., vitamin A, C, and/or E).

For the skin tightening methods described herein, the use of anticoagulative and/or procoagulative agents may be of particular relevance. For instance, by controlling the extent of bleeding and/or clotting in the ablations, the skin tightening effect can be more effectively controlled. Thus, in some embodiments, the methods and devices herein include one or more anticoagulative agents, one or more procoagulative agents, one or more hemostatic agents, or combinations thereof. In particular embodiments, the therapeutic agent controls the extent of bleeding and/or clotting in the treated skin region, including the use one or more anticoagulative agents (e.g., to inhibit clot formation prior to skin healing or slit/hole closure) and/or one or more hemostatic or procoagulative agents.

Kits, Optionally Including One or More Ablation Apparatuses, Tissue Removal Apparatuses, and/or Tissue Positioning Apparatuses Also described herein are kits for skin tightening or for treating diseases, disorders, and conditions that would benefit from skin restoration or tightening. Accordingly, the present invention includes kits having one or more ablation apparatuses, tissue removal apparatuses, and/or tissue positioning apparatuses, as well as kits having a combination of two or more apparatuses, where at least one device is an ablation apparatus as described herein. In addition, kits of the invention may include one or more devices incorporating one or more ablation apparatuses, tissue removal apparatuses, and/or tissue positioning apparatuses in combination or individually.

The kit can include any other useful components. Exemplary components include instructions on how to use the device(s), an air blower, a heat gun, a heating pad, one or more therapeutic agents (e.g., any described herein, such as an anticoagulative and/or procoagulative agent, and optionally in combination with a useful dispenser for applying the therapeutic agent, such as a brush, spray, film, ointment, cream, lotion, or gel), one or more wound cleansers (e.g., including any antibiotic, antimicrobial, or antiseptic, such as those described herein, in any useful form, such as a brush, spray, film, ointment, cream, lotion, or gel), one or more compression dressings (e.g., as described herein), one or more closures (e.g., bandage, hemostats, sutures, or adhesives), one or more debriding agents, one or more adhesives (e.g., any described herein), one or more cosmetics (e.g., as described herein), and/or other suitable or useful materials.

Methods for Treating Skin Regions

The present invention relates to apparatuses, methods, and devices that can be applied to treat one or more skin regions. In particular embodiments, these regions are treated with one or more procedures to improve skin appearance. Accordingly, the devices, ablation apparatuses, tissue removing and tissue positioning apparatuses, and methods herein can be useful for skin rejuvenation (e.g., removal of pigment, veins (e.g., spider veins or reticular veins), and/or vessels in the skin) or for treating acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., crow's feet, age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, skin laxity (e.g., loose or sagging skin or other skin irregularities), striae (or stretch marks), tattoo removal, vascular lesions (e.g., angioma, erythema, hemangioma, papule, port wine stain, rosacea, reticular vein, or telangiectasia), or any other unwanted skin irregularities.

Such treatments can be include any parts of the body, including the face (e.g., eyelid, cheeks, chin, forehead, lips, or nose), neck, chest (e.g., as in a breast lift), arms, hands, legs, abdomen, and/or back. Accordingly, the apparatuses of the invention can be arranged or configured to be amenable to the size or geometry of different body regions. Such arrangements and configurations can include any useful shape (e.g., linear, curved, or stellate), size, and/or depth.

In general, the treatment methods include forming a series of small wounds formed by the ablation of tissue (e.g., removal of ablated tissue portions). These small wounds (e.g., microwounds) reduce tissue volume or improve tissue quality upon healing. For example, a series of ablated tissue portions (e.g., ablation of about 5-40% (e.g., 10-40%) of the total skin area) in high laxity skin region can be compressed to close the wounds and promote the growth of new skin (i.e. improved tissue). Healing of the tissue under compression allows for the existing tissue to span the gap introduced by the ablated tissue portion, therefore reducing the skin volume and skin areal dimension (i.e. tightening the skin).

In one embodiment, ablated tissue portions are formed using a hollow blade or micro-coring needle. Prior to ablation, the skin region can be put under tension to create a flat skin region using a tissue positioning device. The tissue positioning device maintains the tension force on the skin region during the ablation. An ablation apparatus is positioned over the skin region. The hollow blades are inserted into the skin region to circumscribe tissue with a dimension less than 1 mm. The hollow blade is removed leaving behind the ablated tissue portion. The ablated tissue portion is removed from the skin region using a tissue removal apparatus, such as an adhesive device or vacuum device. Once the ablated tissue portion is formed, the resulting hole can be compressed and sealed using a dressing, closure, glue, or suture.

In one exemplary procedure, a plurality of tissue portions are ablated from a skin region in a subject (e.g., about 2, 3, 4, 5, 6, 7, 8, 9, 10, 15, 20, 25, 30, 35, 40, 45, 50, 75, 100, or more tissue portions, such as between about 2 and 100 tissue portions (e.g., between 2 and 10, 2 and 15, 2 and 20, 2 and 25, 2 and 30, 2 and 35, 2 and 40, 2 and 45, 2 and 50, 2 and 75, 5 and 10, 5 and 15, 5 and 20, 5 and 25, 5 and 30, 5 and 35, 5 and 40, 5 and 45, 5 and 50, 5 and 75, 5 and 100, 10 and 20, 10 and 25, 10 and 30, 10 and 35, 10 and 40, 10 and 45, 10 and 50, 10 and 75, 10 and 100, 15 and 20, 15 and 25, 15 and 30, 15 and 35, 15 and 40, 15 and 45, 15 and 50, 15 and 75, 15 and 100, 20 and 25, 20 and 30, 20 and 35, 20 and 40, 20 and 45, 20 and 50, 20 and 75, 20 and 100, 25 and 30, 25 and 35, 25 and 40, 25 and 45, 25 and 50, 25 and 75, 25 and 100, 30 and 35, 30 and 40, 30 and 45, 30 and 50, 30 and 75, 30 and 100, 35 and 40, 35 and 45, 35 and 50, 35 and 75, 35 and 100, 40 and 45, 40 and 50, 40 and 75, 40 and 100, 50 and 75, or 50 and 100)). In another exemplary procedure, hundreds to thousands of hole per square centimeters are ablated from a skin region in a subject (e.g., many thousands of holes in total to treat a large area (e.g., the arm)), such as from about 10 to about 10000 ablated tissue portions per cm$^2$ area of the skin region, as described herein and in Table 1.

Such tissue portions can be included in any useful geometric, non-geometric, or random array (e.g., such as those described herein for an array of tubes and/or blades). Such tissue portions can have any useful dimension that promotes wound or skin healing. Non-limiting dimensions of a tissue portion includes at least one dimension that is less than about 2.0 mm (e.g., less than or equal to about 1.5 mm, 1 mm, 0.75 mm, 0.5 mm, 0.3 mm, 0.2 mm, 0.1 mm, 0.075 mm, 0.05 mm, or 0.025 mm) or between about 0.025 mm and 2.0 mm (e.g., between about 0.025 mm and 1.5 mm, 0.025 mm and 1.0 mm, 0.025 mm and 0.75 mm, 0.025 mm and 0.5 mm, 0.025 mm and 0.3 mm, 0.025 mm and 0.2 mm, 0.025 mm and 0.1 mm, 0.025 mm and 0.075 mm, 0.025 mm and 0.05 mm, 0.05 mm and 2.0 mm, 0.05 mm and 1.5 mm, 0.05 mm and 1.0 mm, 0.05 mm and 0.75 mm, 0.05 mm and 0.5 mm, 0.05 mm and 0.3 mm, 0.05 mm and 0.2 mm, 0.05 mm and 0.1 mm, 0.05 mm and 0.075 mm, 0.075 mm and 2.0 mm, 0.075 mm and 1.5 mm, 0.075 mm and 1.0 mm, 0.075 mm and 0.75 mm, 0.075 mm and 0.5 mm, 0.075 mm and 0.3 mm, 0.075 mm and 0.2 mm, 0.075 mm and 0.1 mm, 0.1 mm and 2.0 mm, 0.1 mm and 1.5 mm, 0.1 mm and 1.0 mm, 0.1 mm and 0.75 mm, 0.1 mm and 0.5 mm, 0.1 mm and 0.3 mm, 0.1 mm and 0.2 mm, 0.2 mm and 2.0 mm, 0.2 mm and 1.5 mm, 0.2 mm and 1.0 mm, 0.2 mm and 0.75 mm, 0.2 mm and 0.5 mm, 0.2 mm and 0.3 mm, 0.3 mm and 2.0 mm, 0.3 mm and 1.5 mm, 0.3 mm and 1.0 mm, 0.3 mm and 0.75 mm, 0.3 mm and 0.5 mm, 0.5 mm and 2.0 mm, 0.5 mm and 1.5 mm, 0.5 mm and 1.0 mm, 0.5 mm and 0.75 mm, 0.75 mm and 2.0 mm, 0.75 mm and 1.5 mm, or 0.75 mm and 1.0 mm).

In some embodiments, the ablated tissue portions forms a hole in the skin region, where the diameter or width of the hole is less than about 1.0 mm and results in a tissue portion having a diameter or width that is less than about 1.0 mm. In further embodiments, the tissue portion has a diameter or width that is less than about 1.0 mm and a length of more than about 1.0 mm (e.g., about 1.0 mm, 1.5 mm, 2.0 mm. 2.5 mm, 3.0 mm, or 3.5 mm). In particular embodiments, relatively small dimensions of the tissue portions can promote healing while minimizing the formation of scars. In some embodiments, the ablated tissue portions have width to depth ratios including ratios between 1:0.3 to 1:75 (e.g., 1:0.3 to 1:50, 1:0.3 to 1:25, 1:0.3 to 1:5, 1:0.3 to 1:1, 1:1 to 1:75, 1:1 to 1:50, 1:1 to 1:25, 1:1 to 1:5). In other embodiments, the ablated tissue portions have width to depth ratios including ratios between 1:0.3 to 1:1 (e.g., 1:0.3 to 1:1, 1:0.35 to 1:1, 1:0.4 to 1:1, 1:0.45 to 1:1, 1:0.5 to 1:1, 1:0.55 to 1:1, 1:0.6 to 1:1, 1:0.65 to 1:1, 1:0.7 to 1:1, 1:0.75 to 1:1, 1:0.8 to 1:1, 1:0.85 to 1:1, 1:0.9 to 1:1, 1:0.95 to 1:1, 1:0.3 to 1:0.95, 1:0.35 to 1:0.95, 1:0.4 to 1:0.95, 1:0.45 to 1:0.95, 1:0.5 to 1:0.95, 1:0.95 to 0.55 to 1:0.95, 1:0.6 to 1:0.95, 1:0.65 to 1:0.95, 1:0.7 to 1:0.95, 1:0.75 to 1:0.95, 1:0.8 to 1:0.95, 1:0.85 to 1:0.95, 1:0.9 to 1:0.95, 1:0.3 to 1:0.9, 1:0.35 to 1:0.9, 1:0.4 to 1:0.9, 1:0.45 to 1:0.9, 1:0.5 to 1:0.9, 1:0.9 to 0.55 to 1:0.9, 1:0.6 to 1:0.9, 1:0.65 to 1:0.9, 1:0.7 to 1:0.9, 1:0.75 to 1:0.9, 1:0.8 to 1:0.9, 1:0.85 to 1:0.9, 1:0.3 to 1:0.85, 1:0.35 to 1:0.85, 1:0.4 to 1:0.85, 1:0.45 to 1:0.85, 1:0.5 to 1:0.85, 1:0.85 to 0.55 to 1:0.85, 1:0.6 to 1:0.85, 1:0.65 to 1:0.85, 1:0.7 to 1:0.85, 1:0.75 to 1:0.85, 1:0.8 to 1:0.85, 1:0.3 to 1:0.8, 1:0.35 to 1:0.8, 1:0.4 to 1:0.8, 1:0.45 to 1:0.8, 1:0.5 to 1:0.8, 1:0.8 to 0.55 to 1:0.8, 1:0.6 to 1:0.8, 1:0.65 to 1:0.8, 1:0.7 to 1:0.8, 1:0.75 to 1:0.8, 1:0.3 to 1:0.75, 1:0.35 to 1:0.75, 1:0.4 to 1:0.75, 1:0.45 to 1:0.75, 1:0.5 to 1:0.75, 1:0.75 to 0.55 to 1:0.75, 1:0.6 to 1:0.75, 1:0.65 to 1:0.75, 1:0.7 to 1:0.75, 1:0.3 to 1:0.65, 1:0.35 to 1:0.65, 1:0.4 to 1:0.65, 1:0.45 to 1:0.65, 1:0.5 to 1:0.65, 1:0.65 to 0.55 to 1:0.65, 1:0.6 to 1:0.65, 1:0.3 to 1:0.65, 1:0.35 to 1:0.65, 1:0.4 to 1:0.65, 1:0.45 to 1:0.65, 1:0.5 to 1:0.65, 1:0.65 to 0.55 to 1:0.65, 1:0.6 to 1:0.65, 1:0.3 to 1:0.6, 1:0.35 to 1:0.6, 1:0.4 to 1:0.6, 1:0.45 to 1:0.6, 1:0.5 to 1:0.6, 1:0.6 to 0.55 to 1:0.6, 1:0.3 to 1:0.55, 1:0.35 to 1:0.55, 1:0.4 to 1:0.55, 1:0.45 to 1:0.55, 1:0.5 to 1:0.55, 1:0.3 to 1:0.5, 1:0.35 to 1:0.5, 1:0.4 to 1:0.5, 1:0.45 to 1:0.5, 1:0.5 to 1:0.5, 1:0.3 to 1:0.45, 1:0.35 to 1:0.45, 1:0.4 to 1:0.45, 1:0.3 to 1:0.4, 1:0.35 to 1:0.4, or 1:0.3 to 1:0.35) and 1:25 to 1:75 (e.g., 1:25 to 1:75, 1:30 to 1:75, 1:35 to 1:75, 1:40 to 1:75, 1:45 to 1:75, 1:50 to 1:75, 1:55 to 1:75, 1:60 to 1:75, 1:65 to 1:75, 1:70 to 1:75, 1:25 to 1:70, 1:30 to 1:70, 1:35 to 1:70, 1:40 to 1:70, 1:45 to 1:70, 1:50 to 1:70, 1:55 to 1:70, 1:60 to 1:70, 1:65 to 1:70, 1:25 to 1:65, 1:30 to 1:65, 1:35 to 1:65, 1:40 to 1:65, 1:45 to 1:65, 1:50 to 1:65, 1:55 to 1:65, 1:60 to 1:65, 1:25 to 1:60, 1:30 to 1:60, 1:35 to 1:60, 1:40 to 1:60, 1:45 to 1:60, 1:50 to 1:60, 1:55 to 1:60, 1:25 to 1:55, 1:30 to 1:55, 1:35 to 1:55, 1:40 to 1:55, 1:45 to 1:55, 1:50 to 1:55, 1:25 to 1:50, 1:30 to 1:50, 1:35 to 1:50, 1:40 to 1:50, 1:45 to 1:50, 1:25 to 1:45, 1:30 to 1:45, 1:35 to 1:45, 1:40 to 1:45, 1:25 to 1:40, 1:30 to 1:40, 1:35 to 1:40, 1:25 to 1:35, 1:30 to 1:35, or 1:25 to 1:30).

Exemplary ablated tissue portion widths include from about 0.1 mm to about 0.8 mm (e.g., 0.1 mm to 0.8 mm, 0.1 mm to 0.6 mm, 0.1 mm to 0.4 mm, 0.1 mm to 0.2 mm, 0.2 mm to 0.8 mm, 0.2 mm to 0.6 mm, 0.2 mm to 0.4 mm, 0.2 mm to 0.3 mm, 0.3 mm to 0.8 mm, 0.3 mm to 0.6 mm, 0.3 mm to 0.4 mm, 0.4 mm to 0.8 mm, 0.4 mm to 0.6 mm, 0.4 mm to 0.5 mm, 0.5 mm to 0.8 mm, 0.5 mm to 0.6 mm, 0.6 mm to 0.8 mm, 0.6 mm to 0.7 mm, or 0.7 mm to 0.8 mm). Exemplary ablated tissue portion widths includes 0.9 mm to 20 mm (e.g., 0.9 mm to 20 mm, 0.9 mm to 17 mm, 0.9 mm to 14 mm, 0.9 mm to 11 mm, 0.9 mm to 8 mm, 0.9 mm to 5 mm, 0.9 mm to 3 mm, 3 mm to 20 mm, 3 mm to 17 mm, 3 mm to 14 mm, 3 mm to 11 mm, 3 mm to 8 mm, 3 mm to 5 mm, 5 mm to 20 mm, 5 mm to 17 mm, 5 mm to 14 mm, 5 mm to 11 mm, 5 mm to 8 mm, 8 mm to 20 mm, 8 mm to 17 mm, 8 mm to 14 mm, 8 mm to 11 mm, 11 mm to 20 mm, 11 mm to 17 mm, 11 mm to 14 mm, 14 mm to 20 mm, 14 mm to 17 mm, or 17 mm to 20 mm) and 0.01 mm to 0.25 mm (e.g., 0.01 mm to 0.25 mm, 0.02 mm to 0.25 mm, 0.03 mm to 0.25 mm, 0.05 mm to 0.25 mm, 0.075 mm to 0.25 mm, 0.1 mm to 0.25 mm, 0.15 mm to 0.25 mm, 0.2 mm to 0.25 mm, 0.01 mm to 0.2 mm, 0.02 mm to 0.2 mm, 0.03 mm to 0.2 mm, 0.05 mm to 0.2 mm, 0.075 mm to 0.2 mm, 0.1 mm to 0.2 mm, 0.15 mm to 0.2 mm, 0.01 mm to 0.15 mm, 0.02 mm to 0.15 mm, 0.03 mm to 0.15 mm, 0.05 mm to 0.15 mm, 0.075 mm to 0.15 mm, 0.1 mm to 0.15 mm, 0.01 mm to 0.1 mm, 0.02 mm to 0.1 mm, 0.03 mm to 0.1 mm, 0.05 mm to 0.1 mm, 0.075 mm to 0.1 mm, 0.01 mm to 0.075 mm, 0.02 mm to 0.075 mm, 0.03 mm to 0.075 mm, 0.05 mm to 0.075 mm, 0.01 mm to 0.05 mm, 0.02 mm to 0.05 mm, 0.03 mm to 0.05 mm, 0.01 mm to 0.03 mm, 0.02 mm to 0.03 mm, 0.03 mm to 0.03 mm, 0.01 mm to 0.03 mm, 0.02 mm to 0.03 mm, or 0.01 mm to 0.02 mm).

In other embodiments, the ablated tissue portions forms a slit in the skin region, where the length or width of the slit is less than about 1.0 mm and results in a tissue portion having a length or width that is less than about 1.0 mm. In further embodiments, the tissue portion has a length or width that is less than about 1.0 mm and a length of more than about 1.0 mm (e.g., about 1.0 mm, 1.5 mm, 2.0 mm. 2.5 mm, 3.0 mm, 3.5 mm, 4.0 mm, 4.5 mm, 5.0 mm, 5.5 mm, or 6.0 mm). In particular embodiments, relatively small dimensions of the tissue portions can promote healing while minimizing the formation of scars.

When viewed from the top of the skin (i.e., along the z-direction or within the xy-plane of the skin), the shape of the hole can be circular or non-circular (e.g., elliptical). Exemplary shapes of tissue portions are provided in FIGS. 1A-1C and 3A-3C and its associated text of U.S. Pub. No. 2012/0041430, which are hereby incorporated by reference in its entirety.

Any beneficial areal fraction of the skin region can be removed, such as an areal fraction of less than about 70% (e.g., less than about 65%, 60%, 55%, 50%, 45%, 40%, 35%, 30%, 25%, 20%, 10%, or 5%) or such as between about 5% and 80% (e.g., between about 5% and 10%, 5% and 10%, 5% and 20%, 5% and 25%, 5% and 30%, 5% and 35%, 5% and 40%, 5% and 45%, 5% and 50%, 5% and 55%, 5% and 60%, 5% and 65%, 5% and 70%, 5% and 75%, 10% and 10%, 10% and 20%, 10% and 25%, 10% and 30%, 10% and 35%, 10% and 40%, 10% and 45%, 10% and 50%, 10% and 55%, 10% and 60%, 10% and 65%, 10% and 70%, 10% and 75%, 10% and 80%, 15% and 20%, 15% and 25%, 15% and 30%, 15% and 35%, 15% and 40%, 15% and 45%, 15% and 50%, 15% and 55%, 15% and 60%, 15% and 65%, 15% and 70%, 15% and 75%, 15% and 80%, 20% and 25%, 20% and 30%, 20% and 35%, 20% and 40%, 20% and 45%, 20% and 50%, 20% and 55%, 20% and 60%, 20% and 65%, 20% and 70%, 20% and 75%, or 20% and 80%).

The skin region can be removed with various hole density (i.e., number of holes per unit area) for different skin-penetrating component sizes and different areal fractions. As a non-limiting example, Table 1 below provides the calculated number of holes for a particular areal fraction (column labeled "Percentage removed") of a treatment region (column labeled "Treatment area length" and "Treatment area width") using a particular needle gauge. In some embodiments, 21 to 24 gauge needles are preferred. In particular, 22 gauge needles are preferred. In some preferred embodiments, 5-20% of treatment region is removed, for example, using 21-24 gauge needles (e.g., 22 gauge needles). The number of holes can be attained by using a single needle and actuating the needle across the treatment area. Alternatively, the number of holes can be attained by using an array of needles and repeatedly actuating the across the treatment area. For example, for 14 holes using a 19 gauge needle (first row, excluding header, in Table 1), a single needle can be actuated 14 times, or an array having about 5 needles can be actuated three times (to provide an average of 15 holes in the treatment area) in the treatment area. As can be seen by the latter example, the number of holes obtained from a calculation are only approximations to guide the user. Taking another example, for 4,366 holes using a 33 gauge needle (last row in Table 1), a single needle can be actuated 4,366 times. Alternatively, an array having an x number of needles can be actuated 4,366/x times. For instance, if the array has 10 needles, the array can be actuated about 437 times to obtain the intended areal coverage. In another instance, if the array has 20 needles, the array can be actuated about 218 times to obtain the intended areal coverage. Further guidance are provided herein, e.g., in Example 11 for providing calculations to determine the surface of tissue removed by a single skin-penetrating component and the time required to remove the total tissue surface.

TABLE 1

| Needle gauge | Hole diameter [μm] | Surface/hole [mm$^2$] | Treatment area length [mm] | Treatment area width [mm] | Percentage removed | Number of holes | Holes per area [1/cm$^2$] |
|---|---|---|---|---|---|---|---|
| 19 | 686 | 0.370 | 10 | 10 | 5% | 14 | 13.53 |
| 19 | 686 | 0.370 | 10 | 10 | 10% | 27 | 27.06 |
| 19 | 686 | 0.370 | 10 | 10 | 40% | 108 | 108.22 |
| 20 | 603 | 0.286 | 10 | 10 | 5% | 18 | 17.51 |
| 20 | 603 | 0.286 | 10 | 10 | 10% | 35 | 35.02 |
| 20 | 603 | 0.286 | 10 | 10 | 40% | 140 | 140.07 |
| 21 | 514 | 0.207 | 10 | 10 | 5% | 24 | 24.10 |
| 21 | 514 | 0.207 | 10 | 10 | 10% | 48 | 48.19 |
| 21 | 514 | 0.207 | 10 | 10 | 40% | 193 | 192.77 |
| 22 | 413 | 0.134 | 10 | 10 | 5% | 37 | 37.32 |
| 22 | 413 | 0.134 | 10 | 10 | 10% | 75 | 74.65 |
| 22 | 413 | 0.134 | 10 | 10 | 40% | 299 | 298.59 |
| 24 | 311 | 0.076 | 10 | 10 | 5% | 66 | 65.82 |
| 24 | 311 | 0.076 | 10 | 10 | 10% | 132 | 131.64 |
| 24 | 311 | 0.076 | 10 | 10 | 40% | 527 | 526.56 |
| 25 | 260 | 0.053 | 10 | 10 | 5% | 94 | 94.17 |
| 25 | 260 | 0.053 | 10 | 10 | 10% | 188 | 188.35 |
| 25 | 260 | 0.053 | 10 | 10 | 40% | 753 | 753.40 |
| 27 | 210 | 0.035 | 10 | 10 | 5% | 144 | 144.36 |
| 27 | 210 | 0.035 | 10 | 10 | 10% | 289 | 288.72 |
| 25 | 210 | 0.035 | 10 | 10 | 40% | 1,155 | 1154.87 |
| 33 | 108 | 0.009 | 10 | 10 | 5% | 546 | 545.80 |
| 33 | 108 | 0.009 | 10 | 10 | 10% | 1,092 | 1091.60 |
| 33 | 108 | 0.009 | 10 | 10 | 40% | 4,366 | 4366.39 |

A plurality of tissue portions can be ablated from a treatment region. In particular embodiments, the apparatus or device, e.g., any described herein, are configured to provide more than about 10 ablated tissue portions per cm$^2$ area of the skin region (e.g., more than about 15, 20, 30, 40, 50, 60, 70, 80, 90, 100, 150, 200, 250, 300, 350, 400, 450, 500, 550, 600, 650, 700, 750, 800, 850, 900, 950, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, or 10000 ablated tissue portions per cm$^2$ area of the skin region). In other embodiments, the apparatus or device, e.g., any described herein, are configured to provide from about 10 to about 10000 ablated tissue portions per cm$^2$ area of the skin region (e.g., from 15 to 500, 20 to 500, 30 to 500, 40 to 500, 50 to 500, 60 to 500, 70 to 500, 80 to 500, 90 to 500, 100 to 500, 150 to 500, 200 to 500, 250 to 500, 300 to 500, 350 to 500, 400 to 500, 450 to 500, 15 to 1000, 20 to 1000, 30 to 1000, 40 to 1000, 50 to 1000, 60 to 1000, 70 to 1000, 80 to 1000, 90 to 1000, 100 to 1000, 150 to 1000, 200 to 1000, 250 to 1000, 300 to 1000, 350 to 1000, 400 to 1000, 450 to 1000, 500 to 1000, 550 to 1000, 600 to 1000, 650 to 1000, 700 to 1000, 750 to 1000, 800 to 1000, 850 to 1000, 900 to 1000, 950 to 1000, 15 to 5000, 20 to 5000, 30 to 5000, 40 to 5000, 50 to 5000, 60 to 5000, 70 to 5000, 80 to 5000, 90 to 5000, 100 to 5000, 150 to 5000, 200 to 5000, 250 to 5000, 300 to 5000, 350 to 5000, 400 to 5000, 450 to 5000, 500 to 5000, 550 to 5000, 600 to 5000, 650 to 5000, 700 to 5000, 750 to 5000, 800 to 5000, 850 to 5000, 900 to 5000, 950 to 5000, 1000 to 5000, 1250 to 5000, 1500 to 5000, 1750 to 5000, 2000 to 5000, 2250 to 5000, 2500 to 5000, 2750 to 5000, 3000 to 5000, 3250 to 5000, 3500 to 5000, 3750 to 5000, 4000 to 5000, 4250 to 5000, 4500 to 5000, 4750 to 5000, 15 to 7500, 20 to 7500, 30 to 7500, 40 to 7500, 50 to 7500, 60 to 7500, 70 to 7500, 80 to 7500, 90 to 7500, 100 to 7500, 150 to 7500, 200 to 7500, 250 to 7500, 300 to 7500, 350 to 7500, 400 to 7500, 450 to 7500, 500 to 7500, 550 to 7500, 600 to 7500, 650 to 7500, 700 to 7500, 750 to 7500, 800 to 7500, 850 to 7500, 900 to 7500, 950 to 7500, 1000 to 7500, 1250 to 7500, 1500 to 7500, 1750 to 7500, 2000 to 7500, 2250 to 7500, 2500 to 7500, 2750 to 7500, 3000 to 7500, 3250 to 7500, 3500 to 7500, 3750 to 7500, 4000 to 7500, 4250 to 7500, 4500 to 7500, 4750 to 7500, 5000 to 7500, 5250 to 7500, 5500 to 7500, 5750 to 7500, 6000 to 7500, 6250 to 7500, 6500 to 7500, 6750 to 7500, 7000 to 7500, 7250 to 7500, 15 to 10000, 20 to 10000, 30 to 10000, 40 to 10000, 50 to 10000, 60 to 10000, 70 to 10000, 80 to 10000, 90 to 10000, 100 to 10000, 150 to 10000, 200 to 10000, 250 to 10000, 300 to 10000, 350 to 10000, 400 to 10000, 450 to 10000, 500 to 10000, 550 to 10000, 600 to 10000, 650 to 10000, 700 to 10000, 750 to 10000, 800 to 10000, 850 to 10000, 900 to 10000, 950 to 10000, 1000 to 10000, 1250 to 10000, 1500 to 10000, 1750 to 10000, 2000 to 10000, 2250 to 10000, 2500 to 10000, 2750 to 10000, 3000 to 10000, 3250 to 10000, 3500 to 10000, 3750 to 10000, 4000 to 10000, 4250 to 10000, 4500 to 10000, 4750 to 10000, 5000 to 10000, 5250 to 10000, 5500 to 10000, 5750 to 10000, 6000 to 10000, 6250 to 10000, 6500 to 10000, 6750 to 10000, 7000 to 10000, 7250 to 10000, 7500 to 10000, 7750 to 10000, 8000 to 10000, 8250 to 10000, 8500 to 10000, 8750 to 10000, 9000 to 10000, 9250 to 10000, 9500 to 10000, and 9750 to 10000 ablated tissue portions per cm$^2$ area of the skin region).

Furthermore, the plurality of tissue portions can be ablated in any beneficial pattern within the skin region. Exemplary patterns within the skin region include tile patterns or fractal-like shapes, where the array of hollow tubes can be arranged, e.g., in a base, to effectuate such a pattern. For example, a higher density and/or smaller spacing of tissue portions (e.g., slits and/or holes) can be ablated in the skin in center of the pattern or in thicker portions of the skin. In another example, the pattern within the skin can be random, staggered rows, parallel rows, a circular pattern, a spiral pattern, a square or rectangular pattern, a triangular pattern, a hexagonal pattern, a radial distribution, or a combination of one or more such patterns of the ablated tissue portions. The pattern can arise from modifications to the average length, depth, or width of an ablated tissue portion, as well as the density, orientation, and spacing between such ablations (e.g., by using an ablation apparatus or an array of ablation apparatuses having one or more blades or tubes with differing lengths, widths, or geometries that are arranged in a particular density or spacing pattern). Such patterns can be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying the average length, depth, width, density, orientation, and/or spacing between ablations.

Any useful portion of the skin or underlying structures (e.g. SMAS) can be ablated. Such tissue portions can include epidermal tissue, dermal tissue, and/or cells or tissue proximal to the dermal/fatty layer boundary (e.g., stem cells). In particular embodiments, ablated tissue portions forms a hole in the skin region, where the depth of the hole is more than about 1.0 mm and results in a tissue portion having a length that is more than about 1.0 mm (e.g., about 1.0 mm, 1.5 mm, 2.0 mm. 2.5 mm, 3.0 mm, 3.5 mm, 4.0 mm. 4.5 mm, 5.0 mm, 5.5 mm, or 6.0 mm). In particular embodiments, the ablated tissue portions forms a slit in the skin region, where the depth of the slit is more than about 1.0 mm and results in a tissue portion having a length that is more than about 1.0 mm (e.g., about 1.0 mm, 1.5 mm, 2.0 mm. 2.5 mm, 3.0 mm, 3.5 mm, 4.0 mm. 4.5 mm, 5.0 mm, 5.5 mm, or 6.0 mm). In some embodiments, the tissue portion has a length that corresponds to a typical total depth of the skin layer (e.g., epidermal and dermal layers). Based on the part of the body, the total depth of the epidermal and dermal layers can vary. In some embodiments, the depth of the epidermal layer is between about 0.8 mm to 1.4 mm, and/or the depth of the dermal layer is between about 0.3 mm to 6.0 mm. In other embodiments, the total depth of the skin layer (e.g., epidermal and dermal layers) is between about 0.9 mm and 6.0 mm, thereby resulting in a tissue portion having a length between about 0.9 mm and 6.0 mm (e.g., between about 0.9 mm and 1.5 mm, 0.9 mm and 2.0 mm, 0.9 mm and 2.5 mm, 0.9 mm and 3.0 mm, 0.9 mm and 3.5 mm, 0.9 mm and 4.0 mm, 0.9 mm and 4.5 mm, 0.9 mm and 5.0 mm, 0.9 mm and 5.5 mm, 0.9 mm and 6.0 mm, 1.5 mm and 2.0 mm, 1.5 mm and 2.5 mm, 1.5 mm and 3.0 mm, 1.5 mm and 3.5 mm, 1.5 mm and 4.0 mm, 1.5 mm and 4.5 mm, 1.5 mm and 5.0 mm, 1.5 mm and 5.5 mm, 1.5 mm and 6.0 mm, 2.0 mm and 2.5 mm, 2.0 mm and 3.0 mm, 2.0 mm and 3.5 mm, 2.0 mm and 4.0 mm, 2.0 mm and 4.5 mm, 2.0 mm and 5.0 mm, 2.0 mm and 5.5 mm, 2.0 and 6.0 mm, 2.5 mm and 3.0 mm, 2.5 mm and 3.5 mm, 2.5 mm and 4.0 mm, 2.5 mm and 4.5 mm, 2.5 mm and 5.0 mm, 2.5 mm and 5.5 mm, 2.5 mm and 6.0 mm, 3.0 mm and 3.5 mm, 3.0 mm and 4.0 mm, 3.0 mm and 4.5 mm, 3.0 mm and 5.0 mm, 3.0 mm and 5.5 mm, 3.0 and 6.0 mm, 3.5 mm and 4.0 mm, 3.5 mm and 4.5 mm, 3.5 mm and 5.0 mm, 3.5 mm and 5.5 mm, 3.5 and 6.0 mm, 4.0 mm and 4.5 mm, 4.0 mm and 5.0 mm, 4.0 mm and 5.5 mm, 4.0 and 6.0 mm, 4.5 mm and 5.0 mm, 4.5 mm and 5.5 mm, 4.5 and 6.0 mm, 5.0 mm and 5.5 mm, 5.0 mm and 6.0 mm, or 5.5 mm and 6.0 mm). In yet other embodiments, the average total depth of the tissue portion or the skin layer (e.g., epidermal and dermal layers) is about 1.5 mm. In yet other embodiments, the average total depth of the tissue portion or the skin layer (e.g., epidermal and dermal layers) is about 3 mm. In other embodiments, the average total depth of the tissue portion or the skin layer (e.g., epidermal and dermal layers) is about 6 mm. In further embodiments, the tissue portion does not include a significant amount of subcutaneous tissue, and any apparatus described herein can be optimized (e.g., with one or more stop arrangements) to control the depth of the ablation and/or the length of the ablated tissue portions.

Such components for making ablations (e.g., drills, blades and/or tubes) can include one or more stop arrangements (e.g., one or more collars, which can be coupled to the blade to allow for adjustment along the long axis of the blade or which can be coupled to the outer portion of the tube and be adjusted along the long axis of the tube to control the depth of ablation in the biological tissue); one or more sleeves around a portion of a blade and/or a tube, such that the sleeve is slidably translatable along the longitudinal axis of the tube or blade (e.g., to ablate tissue portions below the surface of the skin region); a vibrating arrangement (e.g., a piezoelectric element, a solenoid, a pneumatic element, or a hydraulic element) that mechanically couples to at least one blade or hollow tube (e.g., to promote insertion of one or more blades or tubes into the skin region, such as by providing an amplitude of vibration in the range of about 50-500 µm (e.g., between about 100-200 µm) or by providing a frequency of the induced vibrations to be between about 10 Hz and about 10 kHz (e.g., between about 500 Hz and about 2 kHz, or even about 1 kHz)); a suction or pressure system (e.g., by squeezing a flexible bulb or deformable membrane attached thereto or by opening a valve leading from a source of elevated pressure, such as a small pump) to stabilize the surrounding skin region prior to ablation and/or to facilitate removal of the skin portions from the tube; a pin within the lumen to the tube to facilitate removal of the skin portions from the tube; one or more actuators for positioning, translating, and/or rotating the one or more blades and/or tubes relative to the skin portion or relative to the optional one or more pins; a housing or frame to stabilize the surrounding skin region prior to ablation; one or more actuators for positioning and/or translating the one or more pins relative to the skin portion or relative to one or more tubes; one or more sensors (e.g., force sensors, optical sensors, laser fibers, photodetectors, and/or position sensors) in communication with one or more tubes, blades, pins, actuators, valves, or pressure systems to detect the position of the tubes or pins, the presence of a tissue portion in the tube, the position of the apparatus relative to the treated skin portion; a reciprocating arrangement attached to a base or a substrate having one or more attached blades or tubes (e.g., a motor or actuator configured to repeatedly insert and/or withdrawn one or more blades or tubes); a fluid system coupled to the blades and/or tubes to facilitate removal of ablated tissue portions or to irrigate the skin portion, e.g., with saline or a phosphate buffered solution; a heat source (e.g., a resistive heater or current) in communication with the blade and/or tube to promote cauterization of ablation of tissue portions; an optical element (e.g., a lens, a prism, a reflector, etc.) to facilitate viewing of the skin portion beneath the apparatus, tube, or blade; and/or an abrading element optionally mounted on a rotating shaft (e.g., to promote dermabrasion).

EXAMPLES

Example 1: Drill Apparatus for Forming an Ablated Tissue Portion

An ablated tissue portion for the treatment of skin can be formed by mechanical means. For example, a drill equipped with a depth stop, a drill bit configured to remove tissue and having a diameter less than 1 mm, can be used to form an ablated tissue portion (FIG. 1). The drill is positioned over the skin region to be ablated. The drill bit is rotated using the drill motor to a rotational speed sufficient for the drill bit to incise the tissue (e.g., a drill rotational speed between about 50 to 2500 rpm, such as about 500 rpm or any ranges described herein). As the drill bit enters the tissue, the device is moved in the Z direction until the depth stop makes contact with the skin surface. The drill bit rotation can be reversed to remove the drill bit and complete the ablation to form an ablated tissue portion.

Many drill bit designs and materials can be used in the exemplary device and method. For example, a twist bit can be used to form a cylindrical shaped hole with uniform sides. A paper drill can be used to form larger diameter hole. A spoon bit (FIGS. 2A and 2B) can be used to make rounded bottom hole or ablated tissue portion. A microauger or tube with cutting teeth can be rotated using a drill to ablate tissue to form an ablated tissue portion. Drill bits can be made of a many materials including: steel, stainless steel, metals, metal alloys (e.g., surgical steel), cobalt steel alloys, metal carbides, polycrystalline diamond, plastic, and ceramics. Drill bits can be made from composite materials including metals and metal alloys coated with black oxide, titanium nitride, titanium aluminum nitride, titanium carbon nitride, diamond powder, zirconium nitride, and other hardening agents and combinations of the materials herein.

Example 2: Wire or Fiber Apparatus for Forming an Ablated Tissue Portion

The mechanical means for non-thermal ablation of tissue to form an ablated tissue portion can be a wire or a fiber attached to a rotating component. For example, a wire can be attached to a needle such that the wire creates an arc extending from the longitudinal axis of the needle (FIG. 3A). The wire can be attached to the needle adjacent to the needle tip and attached in a second location along the needle towards the proximal end of the needle (end attached to rotating component). In this configuration, the tip of the needle anchors itself into the tissue for ablation. The rotating component is activated and the wire rotates with the needle, sweeping out a volume of tissue as the wire turns. The rotational speed can be set to achieve the desired effect (e.g., slower rotation results in less aggressive ablation of tissue and faster rotation results in more aggressive ablation of tissue). The shape of the hole is dictated by the shape of the wire, thus the wire shown in FIG. 3A ablates a rounded bottomed hole. The needle can be moved into the skin to increase the depth. The rotating component can be stopped or reversed in order to back out the needle and wire.

In another example, a wire is attached to an axle having the same diameter as the hole to be created. The wire may be attached off-center and to the outer diameter of the axle. The wire is parallel to the long axis of the axle. When the axle is rotating at high speed along its long axis, the wire trajectory defines a cylinder, co-axial with the axle and of same diameter than the axle. The wire is inserted in the skin while the axle is rotating and it cuts a cylindrical hole. Removal of cut tissue can be accomplished by the tissue removal apparatuses and methods described herein.

In another example, a wire containing device can be used to form an ablated tissue portion with different diameters along the depth. For example, an ablation apparatus can be configured with an axle and a wire attached to the end of the axle (FIG. 3B). In this particular configuration, the wire direction can be adjusted from parallel to perpendicular relative to the longitudinal axis of the axle (e.g., the wire can be adjusted by up to 90 degrees). With the wire parallel to the longitudinal axis, the axle can be rotated at high speed (e.g., 500 to 5000 rpm). The hole formed will have a diameter defined by approximately the diameter of the axle. The axle and wire can be rotated at high speed and penetrate a skin region to a depth of 4 mm, thus forming a hole of a first diameter. The axle can be removed and the wire adjusted by 90 degrees into a position perpendicular to the longitudinal axis of the axle. In this configuration, the length of the wire plus the diameter of the axle will determine the diameter of the hole formed by the axle and wire. The reconfigured wire and axle (i.e., axle with wire perpendicular to the long axis of the axis) can be rotated at high speed and moved into the hole previously drilled to a first diameter. The wire and axle can be moved down the hole to a depth of 2 mm, thus forming a hole with a second diameter. The resulting ablated tissue portion has two different diameters: a first diameter defined by the axle of the ablation apparatus and the bottom 2 mm of the hole, and a second diameter defined by the sum of the axle diameter and the length of the wire and the top 2 mm of the hole. In some cases, ablated tissue portions with more than one diameter along the depth, in particular a larger diameter at the skin region surface than at the hole depth, can be more efficiently closed and have improved healing times. Fibers can be substituted for a wire in any of the above examples of embodiments.

Example 3: Blade Apparatus for Forming an Ablated Tissue Portion

Figure 4:
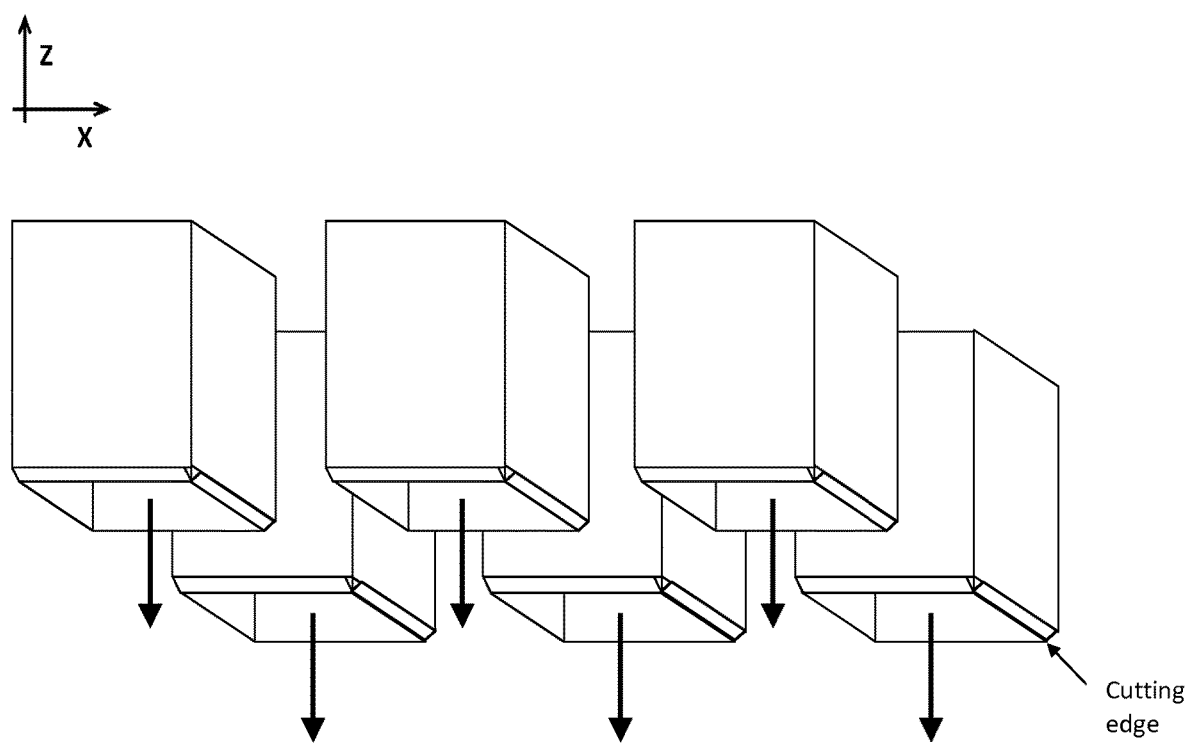
FIG. 4 is a depiction of an exemplary blade array ablation apparatus, each blade apparatus having a square geometry and a cutting edge around the bottom surface. The blade apparatuses are arranged in an array, thus allowing for ablation of multiple tissue portions with a single array device.

The mechanical means for ablation may include one or more blades. For example, an ablation apparatus can be formed by a square shaped tube having blades along the bottom edge of each wall of the square tube. In a further example, an array of square shaped tubes with blade edges (FIG. 4, an array of six square blades) having one or more square tubes separated by a distance configured to extract about 5-40% of the tissue area covered by the array (e.g., the sum of the area of all the square tubes is 5-40% of the total area covered by the array). The blades are pushed into the skin in the direction indicated by the arrow. Different hole patterns may be cut depending on the geometry and number of blades (e.g., a triangle, hexagon, or octagon). Blades may be inserted into the tissues with sufficient force and speed to produce a desired effect. The hole depth can be controlled by the depth of the blade or a stop feature on the apparatus or device.

Figure 5:
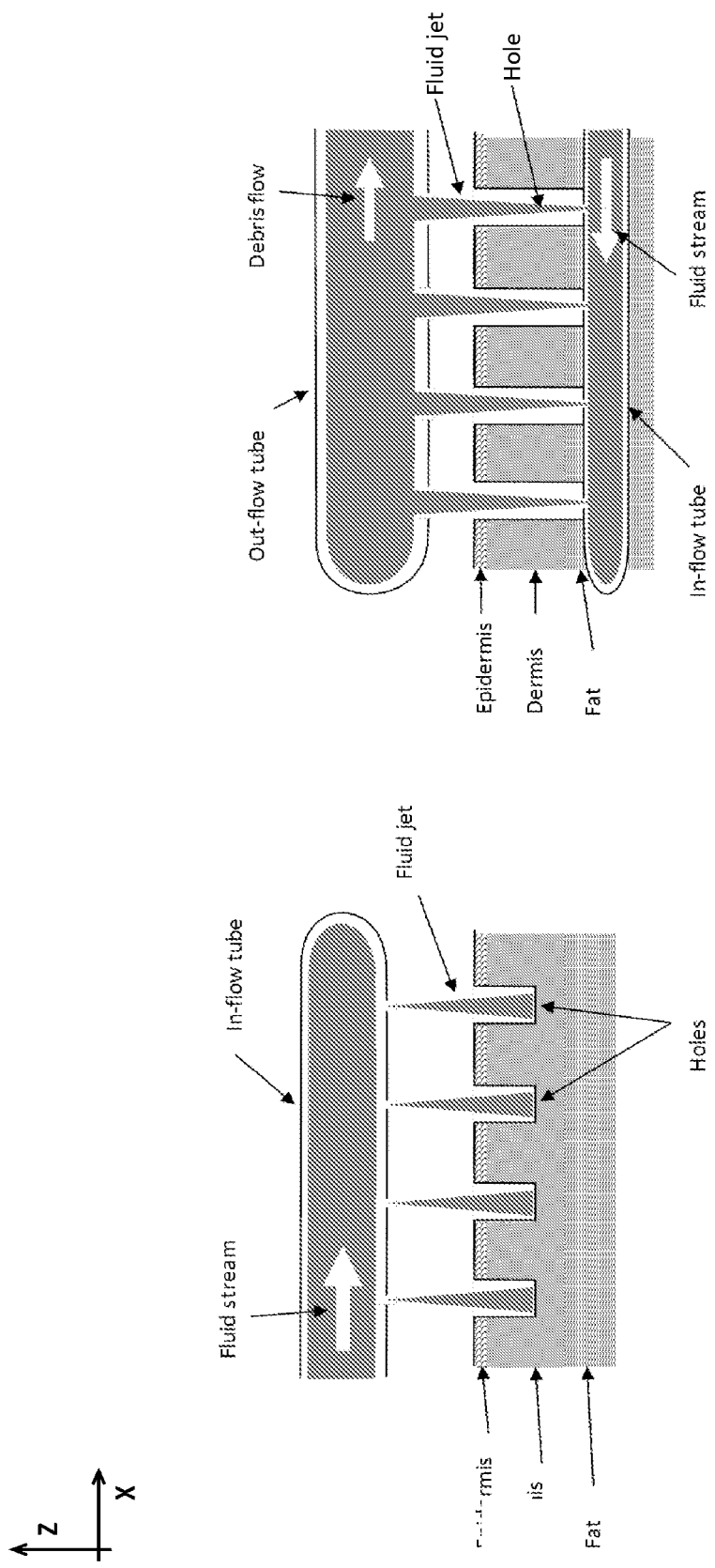
FIGS. 5A and 5B provide exemplary high-pressure fluid jet ablation apparatuses having a cylindrical tube structure with a series of holes to eject the fluid in a coherent stream (e.g., a fluid jet).

Example 4: High Pressure Fluid Jet Apparatus for Forming an Ablated Tissue Portion Non-thermal ablation of tissue can be achieved using high pressure fluid jets (e.g., fluid under pressures greater than about 1380 kPa or 200 psi, including up to 100000 psi). Optionally, operating pressure may be lowered by adding an abrasive (e.g., micro-particles) in the fluid (e.g., water). For example, a fluid stream can be contained in a cylindrical body under high pressure. Fluid jets are formed by holes in the cylindrical body. The cylindrical body and fluid jets can be located external to and with the fluid jets being directed at the skin surface (FIG. 5A). The fluid jets ablate tissue without thermal energy being transferred to the surrounding tissue. The fluid can be removed with a vacuum apparatus or similar means. In another embodiment, the jet array can be moved (e.g., in a circular fashion) in relation to the skin so as to produce an array of cylindrical ablations.

In another example, a cylindrical body containing a plurality of fluid jets that can be inserted in the fatty layer, under the dermis and epidermis (FIG. 5B). The array of fluid jets emits fluid at very high pressure and ablates tissue. A suction tube can be used to remove the fluid and debris. Alternatively, a low pressure out-flow tube can be positioned on the surface of the skin collecting fluid and debris (FIG. 5B). The high pressure fluid jet flow can be continuous or discontinuous fluid flow. Discontinuous fluid flow can provide a step to remove of fluid and debris prior to re-activating the high-pressure jet.

Example 5: Cryosurgery Apparatus for Forming an Ablated Tissue Portion

Figure 6:
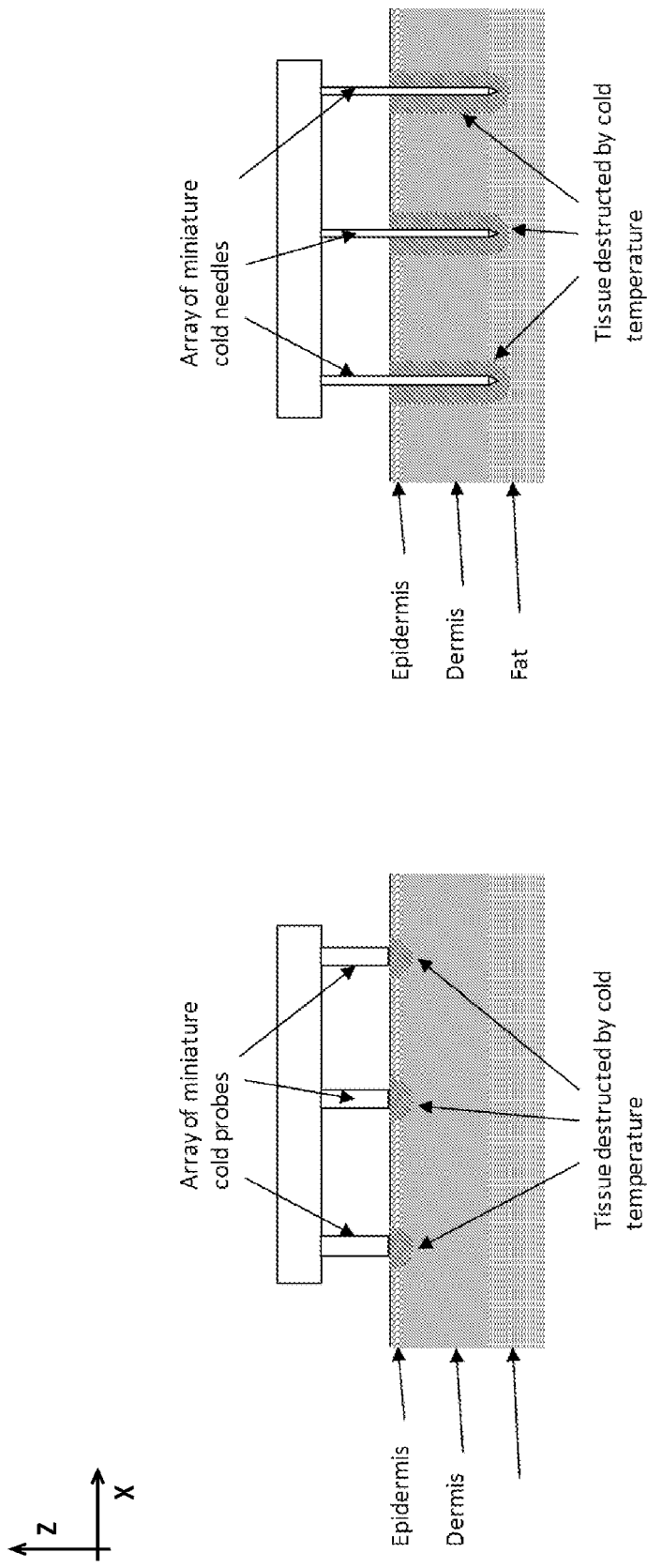
FIGS. 6A and 6B provide exemplary cryosurgery apparatus having a base to support an array of tubes, probes, or needles.

Non-thermal ablation can be achieved using cryosurgical apparatuses and methods. For example, an array of miniature cold probes mounted on a support structure can be applied to a skin surface (FIG. 6A). The probes locally decrease the skin temperature, freeze and destroy the tissue.

In another example, an array of miniature cold needles mounted in a support structure can be inserted into the skin (FIG. 6B). The needles can be made of a thermal conductive material (e.g., a metal). A longer needle can destroy deeper skin structures. The penetrating components can be temperature controlled (in contact with a heat sink or temperature control system).

In another example, penetrating components can have regions composed of temperature non-conductive (e.g., thermal insulator) materials to help shield specific regions or depths of the tissue from exposure to extremes of temperature of the cold needle. For example, a cold needle can be used with a layer of insulating material forming a spiral pattern along the length of the needle. In this manner, holes with many diameters and surface geometries (e.g., a spiral pattern) can be formed.

Example 6: Chemical Agent Apparatus for Forming an Ablated Tissue Portion

Figure 7:
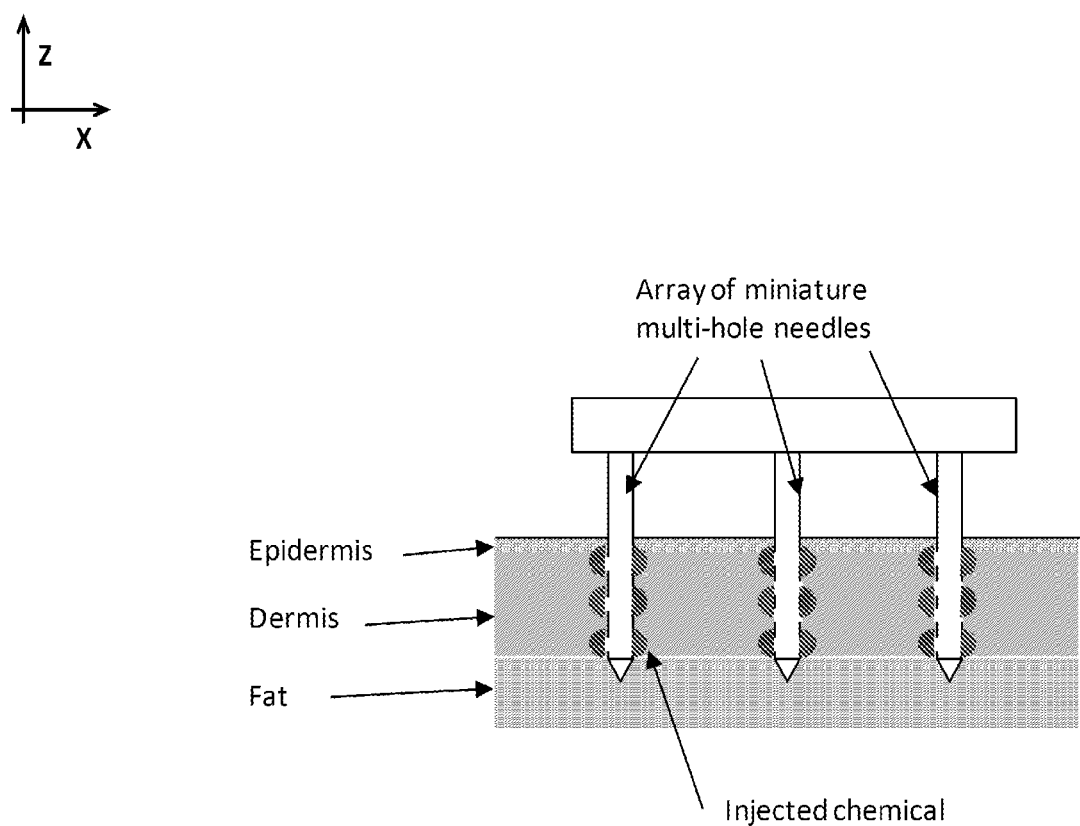
FIG. 7 shows an exemplary chemical ablation apparatus array having a series of needles capable of delivering a chemical or bioactive agent.

Ablated tissue portions can be formed using chemical agents distributed in a skin region by a penetrating component. For example, an array of needles containing holes can be introduced in a skin region (FIG. 7). The needle side holes can inject a chemical denaturizing agent at multiple depths, thus ablating regions of skin tissue. In another example, the needle can have holes spaced such that the chemical agent is not distributed along the entire length of the needle. In this configuration, ablation can occur at specific locations along the length of the needle, thus creating ablated tissue portions with different diameters along the depth or holes with serrated edges.

Example 7: Electroporation Apparatus for Forming an Ablated Tissue Portion

Figure 8:
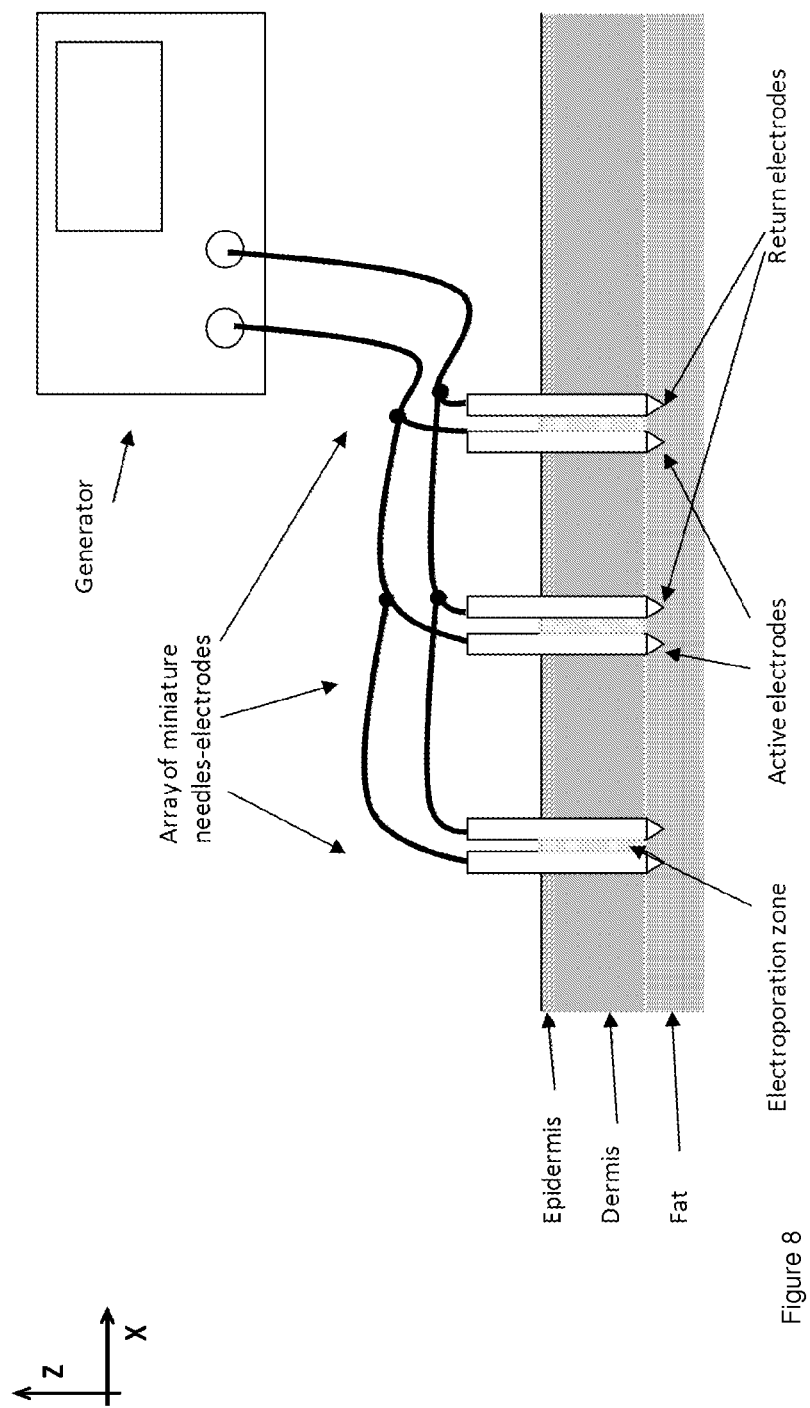
FIG. 8 shows an exemplary electroporation apparatus for ablation of tissue having an array of miniature needle-electrodes, each of which has an active electrode and a return electrode to form a bipolar electrode pair, and a generator to supply electrical energy to the electrodes.

Ablated tissue portions can be formed by the irreversible electroporation of tissue. An array of conductive needles, arranged as pairs of needles, can inserted into the skin (FIG. 8). The needles can be connected to a generator that emits pulses of electricity of a pre-selected duration, frequency and intensity. The needle array can be configured to have an equal number of active electrodes and return electrodes located in close proximity as to generate a pulsed and high intensity electrical field between pairs of electrodes (e.g., bipolar electrode pair). Once activated, an electrical field leads to non-thermal, irreversible electroporation of the tissue located between electrode pairs. The treatment parameters can be selected as to only generate apoptosis of skin cells. The shape of the ablated tissue portion is determined by the geometry of the area between the two needles or electrodes. For example, the two needles can be placed at different angles relative to each other (as opposed to parallel as shown in FIG. 8), thus creating a hole with non-parallel sides. In another example, the penetrating components can be different or complimentary shapes to provide ablated tissue portions with serrated edges and other structures.

Figure 9:
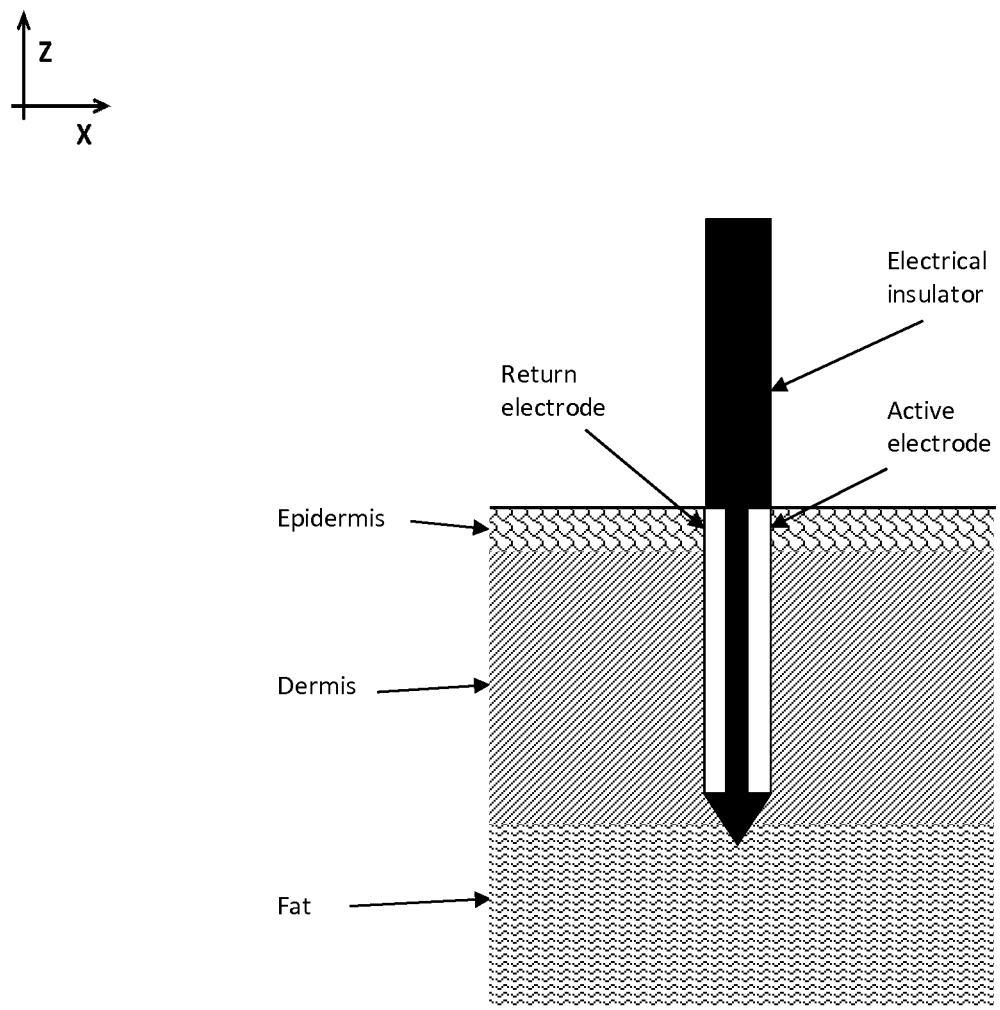
FIG. 9 shows an exemplary electrode or needle-electrode having a cylindrical body made of an electrically insulating material, a single bi-polar electrode where the active and return electrodes are separated by the insulating material.

In another example, a bipolar needle electrode having an active and a return electrode on a cylindrical body, separated by an electrically insulating material can be used in place of a pair of needles (FIG. 9). Activation of the electrode causes ablation around the cylindrical body as energy moves from the active electrode through the skin to the return electrode. The electrode can have many shapes, thus forming ablated tissue portions with different geometries.

Example 8: Tissue Removal Apparatus Using Physical or Mechanical Means

Figure 10B:
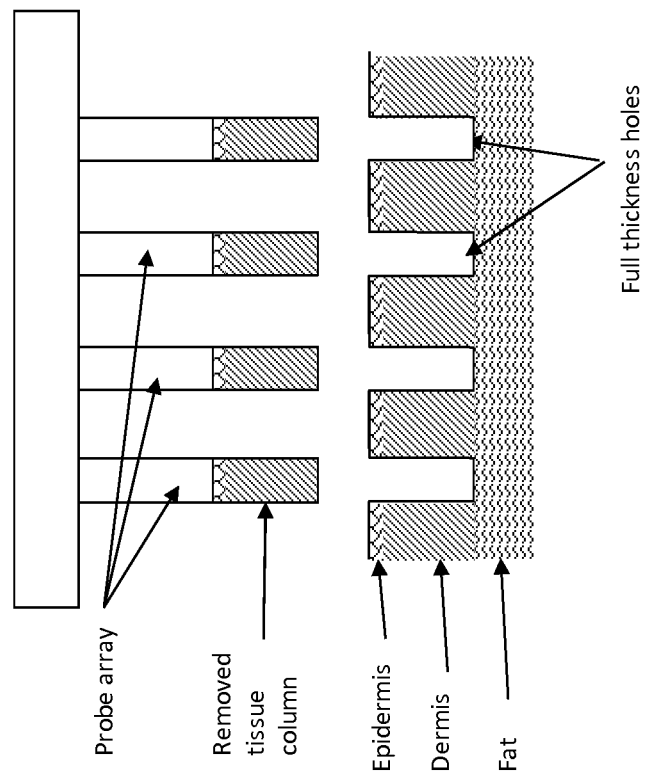
FIGS. 10A and 10B show an exemplary tissue removal array apparatus having a support layer and an adhesive layer.
Figure 10A:
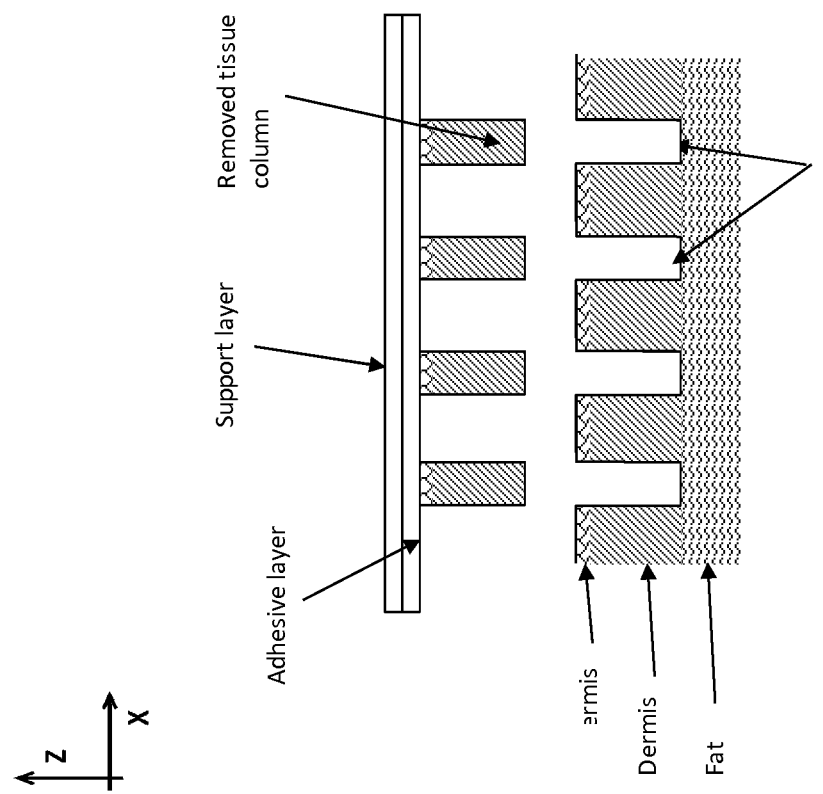

Following ablation, tissue and debris can be removed by physical or mechanical means. For example, a removal device can be configured with a flexible support layer attached to an adhesive layer (e.g., tape). This device can be applied on the skin following ablation (FIG. 10A). The adhesive layer attaches to the tissue to be removed as well as to the remaining skin surface. When the device is lifted from the skin, the tissue to be removed (e.g., ablated tissue portion) is pulled out of the holes. In another example, an array of probes can be applied on the tissue to be removed (FIG. 10B). The probe can be a rigid cylinder in which the bottom surface is covered with an adhesive. Alternatively, the probe can be a probe in which the bottom surface is temperature controlled and sticks to the skin due to freezing between the probe and skin region surfaces. The probes used for tissue removal may be combined with the ablation apparatuses discussed herein.

Example 9: Tissue Removal Apparatus Using Thermal Energy

Figure 12:
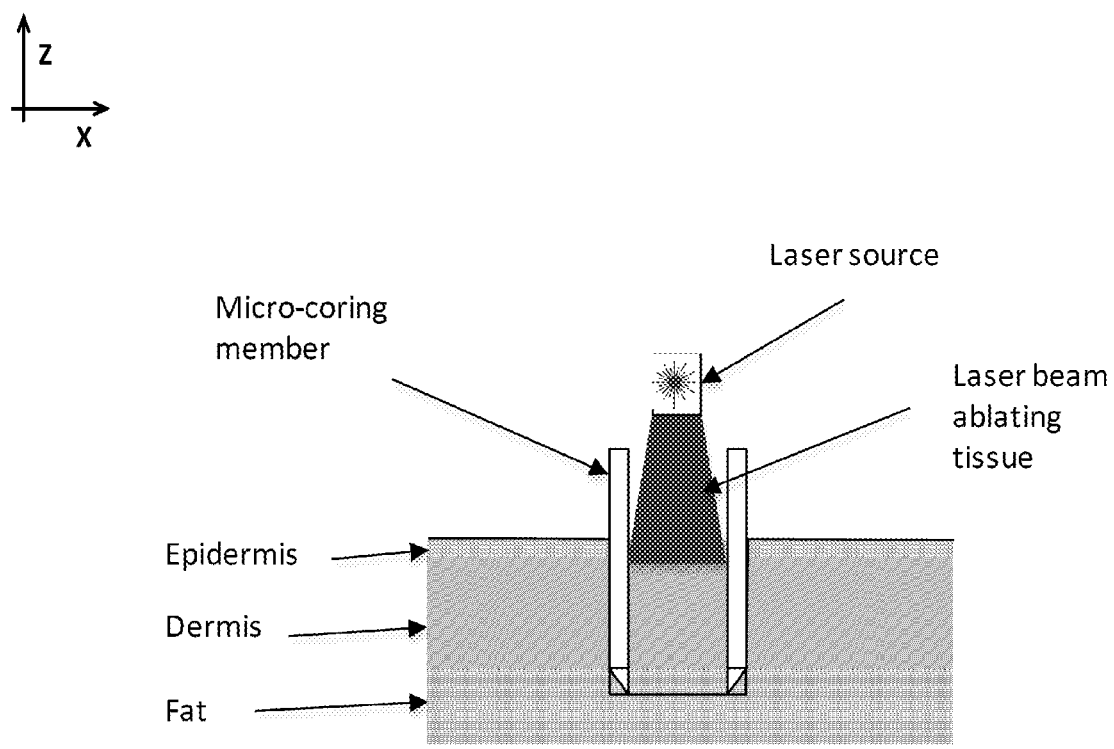
FIG. 12 shows an exemplary tissue removal apparatus having a thermal ablation source (e.g., a laser) and a micro-coring or blade ablation apparatus.

A mechanical ablation apparatus can be used to isolate a tissue region prior to removal of the circumscribed tissue by a thermal ablation method. By isolating the tissue portion to be removed (e.g., ablated tissue portion) from the surrounding tissue, a thermal ablation method can be used without inducing coagulation in the surrounding (e.g., non-ablated) tissues. For example, a micro-coring component (e.g. micro-coring needles, micro-coring paper drill, micro-coring hole saw or micro-coring blade assembly) may be inserted in the skin to cut the tissue without generation of thermal injury. While the micro-coring component is still in the skin, an ablative laser (e.g., a laser delivered by a light guide inside the micro-coring needle) may be used to vaporize the tissue contained in the micro-coring member (FIG. 12). The micro-coring component material may be chosen as to act as a thermal insulator to prevent heating of the tissue outside of the micro-coring component. In one non-limiting embodiment, thermal ablation can be performed first followed by coring to remove the coagulation zone.

Example 10: Tissue Positioning Apparatuses

Figure 13:
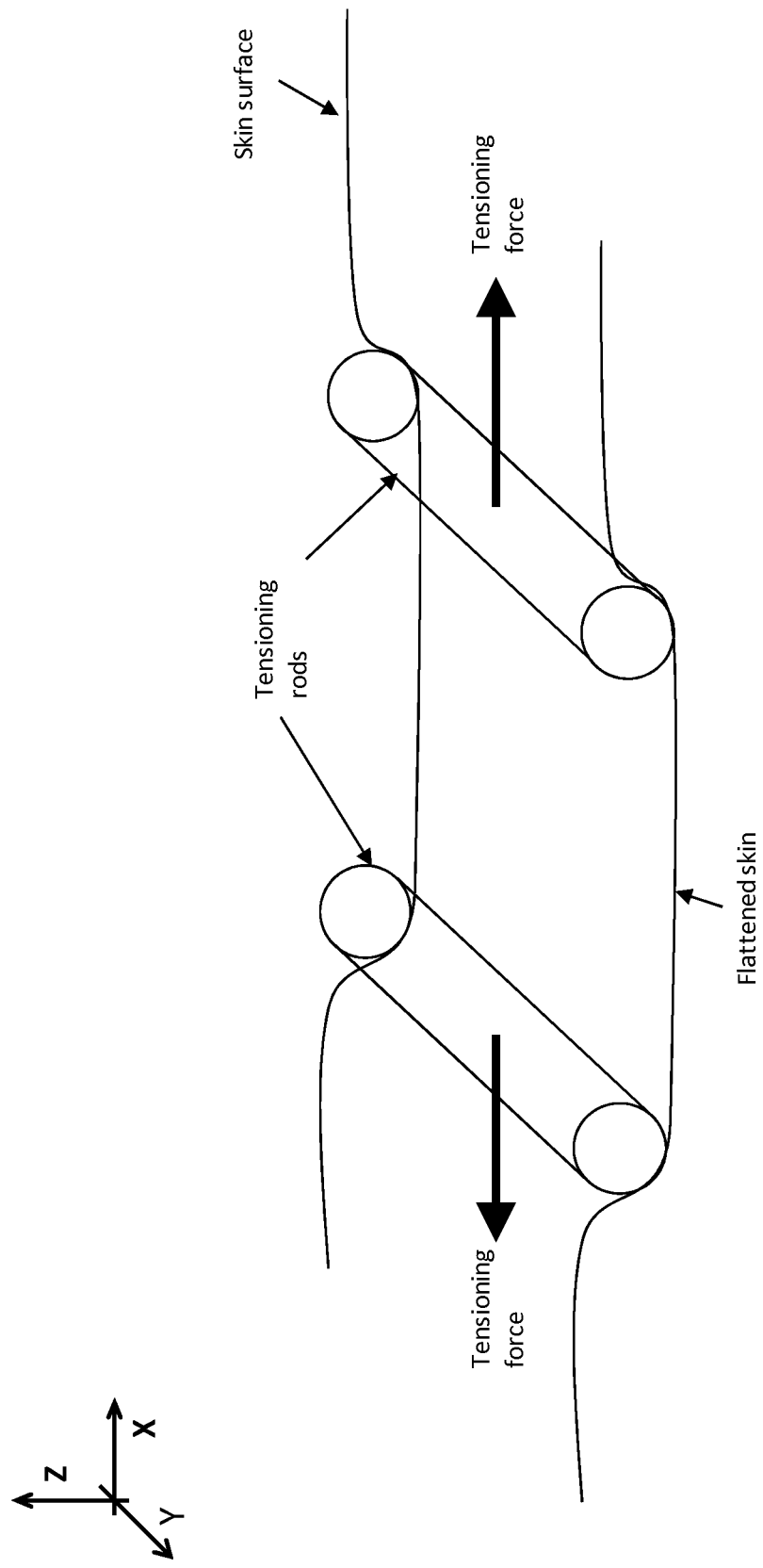
FIG. 13 shows an exemplary tissue positioning apparatus including two cylindrical rods to provide tension to a tissue area prior to, during, or after ablation or tissue removal. The application of tension to the skin region may provide a flat, more even surface for skin treatment.

A tissue positioning apparatus can provide a flat skin surface for non-thermal ablation or skin removal. Tensioning rods (FIG. 13) can be used to apply a force to the skin surface by moving the rods away from each other, thus providing a flat skin region in between. For example, two rubber rods can be positioned adjacent to one another on a skin region. The rods can be moved apart while a force is applied on the rods to provide tension on the skin region (e.g., a downward force of greater than about 10 N/mm$^2$). The tension force can be maintained during ablation and/or tissue removal. In some embodiments, tensioning rods can also be used to apply a force to the skin surface by moving the rods toward each other, thus pinching the skin to elevate the dermis away from the underlying structures (e.g., sub-dermal muscle layer, blood vessels, and nerve fibers) (FIG. 22).

Figure 14:
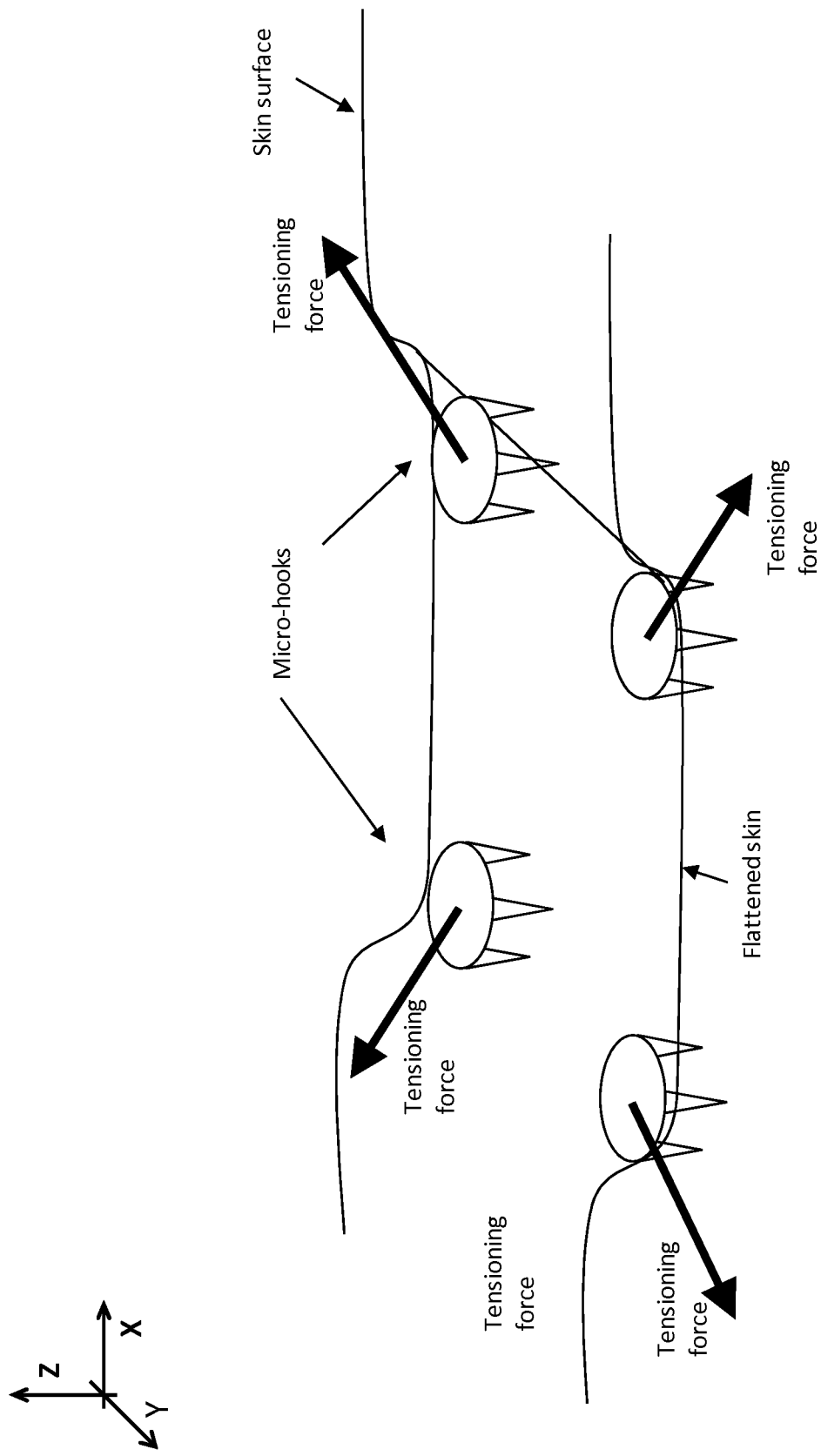
FIG. 14 shows an exemplary tissue positioning apparatus having a series of micro-hooks that can be attached to and hold tension in a tissue or skin region. The micro-hooks may be distributed to provide tension to the skin in order to provide a tensioned or flat surface in a variety of geometric configurations (shown as square region in FIG. 14).

A skin region can be held flat by a series of micro-hooks (FIG. 14) or micro-barbs. For example, four metal, multi-prong tabs can be placed in the four corners of a skin region under tension. The pronged tabs maintain the tension force and hold the skin region between the prongs flat during ablation and/or tissue removal.

Needles that provide a gripping force ("needle grippers") can be deployed in the dermis layer to lift the skin and elevate the dermis away from the underlying structures (e.g., sub-dermal muscle layer, blood vessels, and nerve fibers). Once inserted in the skin (FIG. 23, arrow 1), opposite needles can be pulled away (FIG. 23, arrow 2) from each other to generate skin tension. The needles can then be pulled away from the skin surface to create a displacement of the dermis away from the underlying structures to prevent injury to muscle, blood vessels, and nerve fibers by the micro-coring needles. The level of skin tension can be adjusted by pulling opposite needles away from each other in one direction to create a uni-directional skin tension. The needles can be retracted to release the skin.

Figure 15:
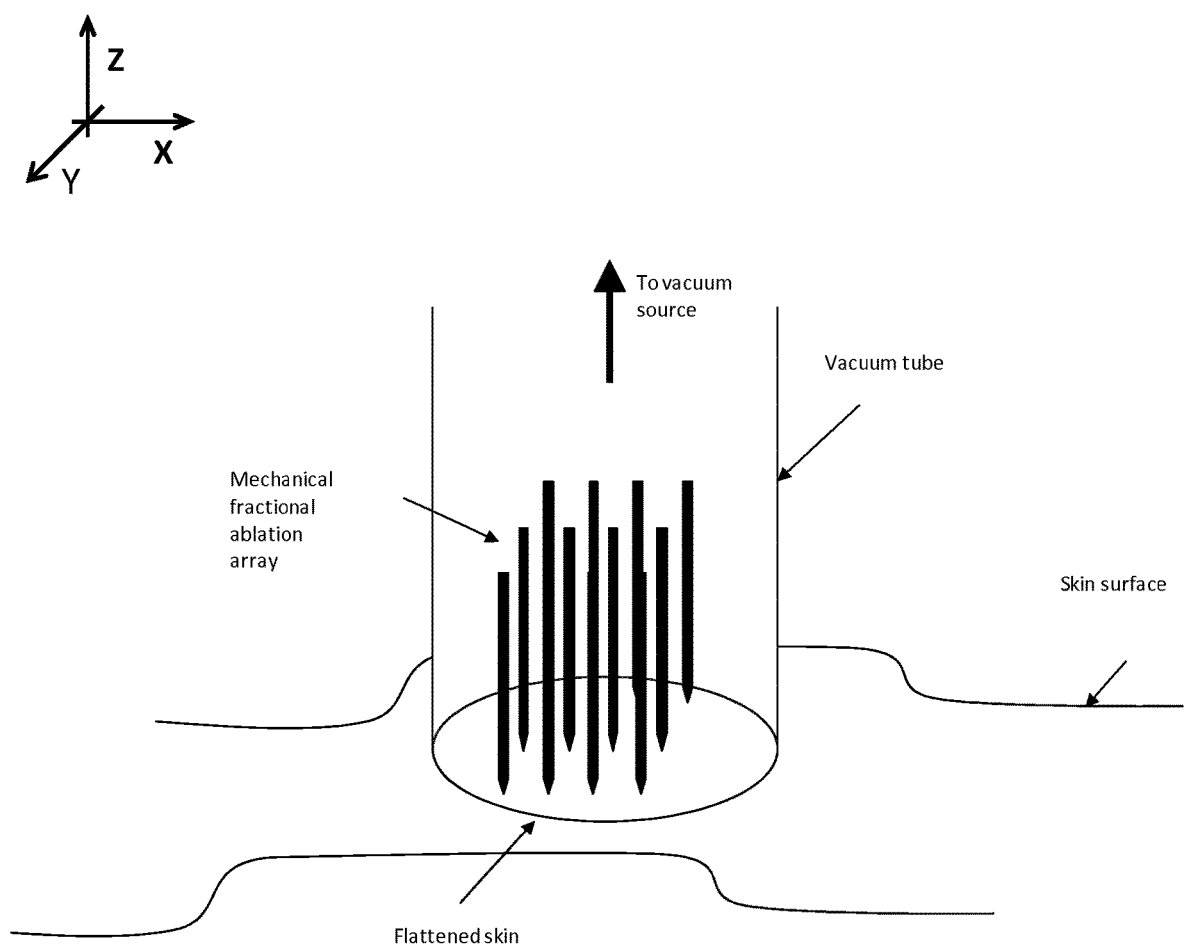
FIG. 15 shows an exemplary tissue positioning apparatus having a tube for applying vacuum around a tissue area to be ablated. The vacuum provides a seal between the tube and the tissue region, thus providing tension across the area. An ablation apparatus (shown as an array of needles) may be included inside the vacuum tube to ablate the skin region while the vacuum positions the tissue.

A vacuum can be applied to a tissue surface to provide a flat skin region (FIG. 15). For example, a housing (e.g., a vacuum tube) with an areal dimension of 10 cm$^2$, access ports for an array of ablation apparatuses, and attached to a vacuum source can be brought into contact with a skin region under tension. A vacuum of 101.3 kPa is applied to the housing, thus forming a seal between the skin region and the housing. The skin region sealed within the housing is held flat and under tension by the reduced pressure. An array of ablation apparatuses can be moved into the housing using the access ports. The tissue of the skin region within the housing can be ablated while the housing remains under a vacuum. In one non-limiting embodiment, the needles can also convey the vacuum.

Figure 16:
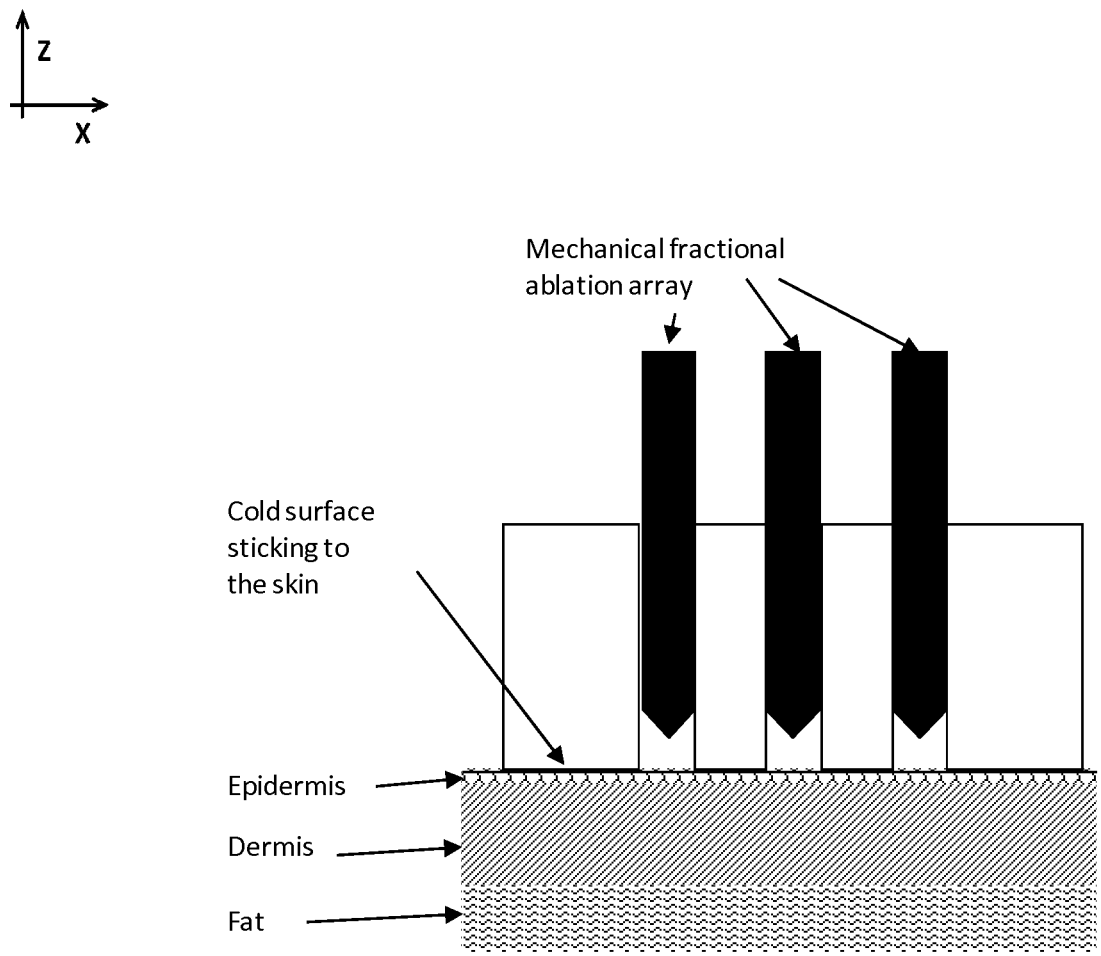
FIG. 16 shows an exemplary tissue positioning apparatus having a housing configured to control the temperature at the tissue interfacing surface and providing access through the housing for an ablation apparatus or array of ablation apparatuses. The temperature at the interface between the positioning device and the tissue surface is lowered until the tissue is held in place by the device.
Figure 18:
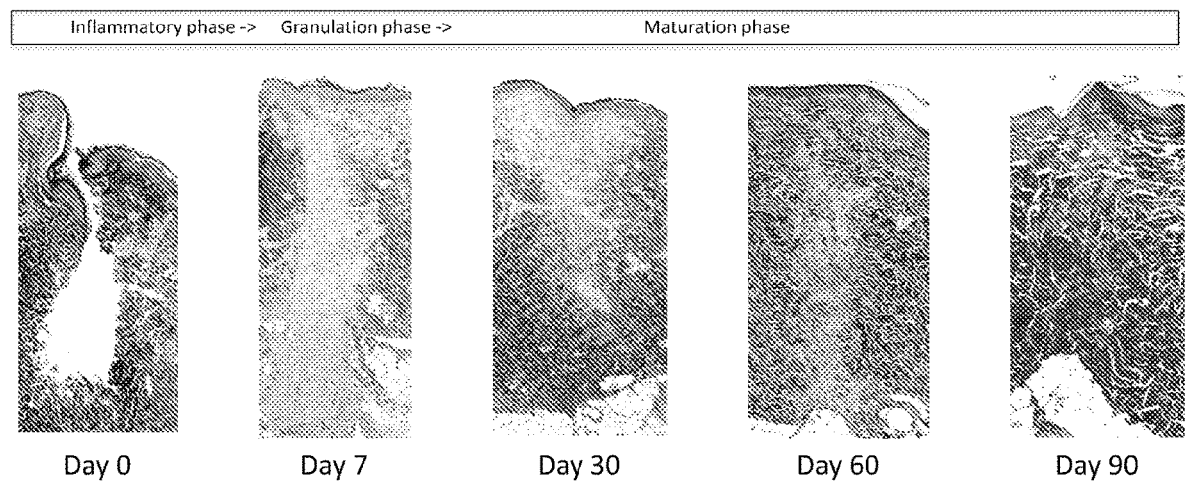
FIG. 18 shows the healing progression after treatment with micro-coring needles on the skin of a Yorkshire pig.

A tissue positioning apparatus having a cold surface and a series of channels configured to accept an array of ablation apparatuses can be used to position a skin region by freezing the skin to the cold surface (FIG. 16). For example, a housing containing a temperature controlled surface and access ports can be cooled to 0 degrees Celsius. The cold surface is brought in contact with a skin region under tension. The cold surface joins with the skin region once freezing occurs between the two surfaces. An array of ablation apparatuses can be moved through the access ports and used to ablate the tissue of the skin region.

A tissue positioning apparatus having an adhesive surface and a series of channels configured to accept an array of ablation apparatuses can be used to position skin by adhering the skin to the adhesive surface (FIG. 17). For example, a housing containing an adhesive covered surface and access ports can be brought in contact with a skin region under tension. The adhesive surface joins with the skin region, thus maintaining the tension and providing a flat skin region. An array of ablation apparatuses can be moved through the access ports and used to ablate the tissue of the skin region. In another embodiment, the ablation device, e.g., a needle or row of needles, inserts into the tissue and then moves laterally, creating tension on the skin, before the next row of needles inserts into the skin. As part of the same mechanism, the skin might be held back by a tension roller (e.g., as provided in FIG. 13).

Example 11: Duration of the Mechanical Fractional Ablation Procedure

The apparatuses, devices, and procedures of the invention can be optimized to perform an ablation procedure within a particular time frame. The following theoretical calculations are non-limiting and provided as an example only. In this non-limiting example, the theoretical calculation involves tightening the skin of the face. The calculation methodology is based on the following approximation: a surgical facelift procedure requires ablation of a tissue surface that could also be ablated by mechanical fractional ablation. Mechanical fractional ablation can involve, e.g., tissue coring by a micro-needle array, such as any described herein. The number of micro-coring events required to remove a tissue surface equivalent to a face-lift is calculated. The number of events is then multiplied by the duration of one micro-coring event to evaluate the duration of the ablation procedure.

Tightening of the tissue of the face is provided as an illustration for this theoretical analysis. This example may be relevant for other procedures, such as for determining the duration of other procedures (e.g., a brow lift, forehead lift, and/or blepharoplasty). Typical placement of incisions for a facelift include those beginning in the hairline at the temples, curving in front of the ear and then around the bottom of the ear, and generally ending near the hairline on the back of the neck. This incision is made on both sides of the head. Without being limited by this example, the length of the incision is generally about 250 mm. The skin is pulled towards the back of the head. A band of skin is excised; its width can be estimated to be less than about 5 mm. Therefore, the total skin surface removed is given by the following equation:

Skin removed=2×250 mm×5 mm=2500 mm$^2$

Mechanical ablation can be achieved by any useful method, such as any described herein. For example, Fernandes et al. demonstrated mechanical fractional ablation with 23G and 25G coring needles in a pig model (Fernandes et al., Micro-mechanical fractional skin rejuvenation, Plast Reconstr Surg. 2013 February; 131(2):216-23, which is hereby incorporated by reference in its entirety). Up to 40% of the tissue was removed in the treatment area, and the skin healed without visible scars. A coring needle can be used to remove a cylindrical volume of tissue which diameter is determined by the inner diameter of the needle, as well as the insertion depth of the needle in the skin. Thus, 23G and 25G needles remove tissue cylinders of about 337 μm and 260 μm in diameter, respectively. Fernandes et al. confirmed experimentally that the coring sites were about 300 μm in diameter. In another example, fractional lasers are broadly used clinically to rejuvenate the skin. They produce lesions that have similar dimensions to the micro-coring lesions described above. For example, Bedi et al. showed that a Fraxel system generates lesions of about 200 μm in diameter (Bedi et al., The effects of pulse energy variations on the dimensions of microscopic thermal treatment zones in nonablative fractional resurfacing, Lasers Surg Med. 2007 February; 39(2): 145-55, which is hereby incorporated by reference in its entirety).

For our calculation, we assume that the device uses 25G needles and generates lesions of similar size to fractional lasers. Using this assumption, the surface of tissue removed by a single 25G needle is:

$$\frac{\pi d^2}{4} = \frac{\pi 0.26^2}{4} = 0.05 \text{ mm}^2$$

In particular non-limiting embodiments, multiple coring needles are assembled in an array to expedite the procedure. There is robust evidence that multiple needles can penetrate the skin simultaneously while avoiding a "needle-bed" effect that would preclude penetration of the needles in the tissue. For instance, Fernandes et al. assembled 4 needles with a 8 mm separation in a piece of rubber for their animal study. In another example, the Dermaroller® is a micro-needling device currently used in clinical practice (Majid, Microneedling therapy in atrophic facial scars: an objective assessment, J Cutan Aesthet Surg. 2009 January; 2(1):26-30). The Dermaroller® needles are non-coring, conic-tip needles that are up to 1.5 mm in length and about 250 μm in diameter. In general, two rows of 8 needles are assembled on a flat plastic holder with a 1.5 mm spacing, and a minimum of 16 needles penetrate the skin simultaneously. In yet another example, the Dermapen® is another micro-needling device with non-coring, conic tip needles. The Dermapen® uses eleven 32G needles penetrating the skin up to 2.5 mm in depth. An electro-mechanical actuator pushes the 11 needles in the tissue at elevated frequency, allowing very fast treatment of a large area of the body. The manufacturer claims that the Dermapen® mechanism allows up to 1000 holes per second. In particular embodiment, the devices, apparatuses, and methods of the invention include 1, 2, 3, 4, 5, 6, 7, 8, 9, or 10 skin-penetrating component(s) (e.g., a needle, a drill, a microauger, a tube comprising cutting teeth, a spoon bit, a wire, a fiber, a blade, a high-pressure fluid jet, a cryoprobe, a cryoneedle, a multi-hole needle comprising one or more chemical agents, a microelectrode, and/or a vacuum, or any other component described herein) that can penetrate the skin simultaneously.

Further examples of treatment areas and surface of tissue removed by a single skin-penetrating component are provided herein, e.g., Table 1. In addition, any beneficial areal fraction of the skin region can be removed, such as an areal fraction of less than about 70% (e.g., as described herein). Based on the above-described equations, a skilled artisan would be able to calculate the number of holes or ablated tissue portions within the treatment area or areal fraction of the treatment area. The following paragraphs provide guidance on how the devices, apparatuses, or methods can be optimized for a particular treatment time or duration.

The speed of the skin-penetrating component can be optimized for treating skin. In some embodiments, the speed is similar to that of a biopsy gun (e.g., the HS Multi 22 device from BIP/Bard for harvest soft tissue clinically, see Konermann et al., Ultrasonographically guided needle biopsy of benign and malignant soft tissue and bone tumors, J Ultrasound Med. 2000 July; 19(7):465-71), such as about 30 m/s. Assuming this speed and that the thickness of the epidermal and dermal layer is 3 mm in the human face (Kakasheva-Mazhenkovska et al., Variations of the histo-morphological characteristics of human skin of different body regions in subjects of different age, Prilozi. 2011 December; 32(2):119-28), the ablation of the tissue at a speed of 30 m/s takes (3 mm/30,000 mm/s)=0.1 ms. In some embodiments, the speed of the skin-penetrating component (e.g., any described herein) is 100 times slower than the biopsy gun, such that the total time required for one actuation is about 10 ms. In particular embodiments, the speed of the skin-penetrating component is about 50 m/s, 40 m/s, 30 m/s, 20 m/s, 10 m/s, 5 m/s, 1 m/s, 0.9 m/s, 0.8 m/s, 0.7 m/s, 0.6 m/s, 0.5 m/s, 0.4 m/s, 0.3 m/s, 0.2 m/s, or 0.1 m/s. In other embodiments, the total time for a single actuation accounts for the travel of the skin-penetrating component(s) back to the starting position and/or for the collection of the tissue sample in the skin-penetrating component (e.g., via a vacuum system). In particular embodiments, the time for a single actuation is about 100 ms, 90 ms, 80 ms, 75 ms, 60 ms, 50 ms, 40 ms, 30 ms, 20 ms, 10 ms, 9 ms, 8 ms, 7 ms, 5 ms, 5 ms, 1 ms, 0.9 ms, 0.8 ms, 0.7 ms, 0.6 ms, 0.5 ms, 0.4 ms, 0.3 ms, 0.2 ms, or 0.1 ms.

The time required to remove the total tissue surface is given by the following formula:

$$\frac{\text{surface to be removed}}{\text{surface removed by 1 component} \times \text{number of component(s) per array}} \times \text{component actuation time.}$$

The component can be a skin-penetrating component. With the assumptions described in the previous paragraph, the ablation duration can be calculated as follows:

$$\frac{2500 \text{ mm}^2 \text{ to be removed}}{0.05 \text{ mm}^2 \times 10 \text{ component(s) per array}} \times 0.01 \text{ ms} = 50 \text{ s.}$$

Assuming that the system is firing at high frequency (e.g., about 100 times per second), the user (e.g., a physician) can move the device or apparatus across the face continuously and slowly while firing or actuating the device. This continuous firing mechanism may or may not be incorporated into the device or apparatus.

Accordingly, the present example provides an exemplary, simple formula for calculating tissue ablation. This calculation is based on the total skin surface to be removed, the geometry of the ablation system determined by experimental data on mechanical micro-coring and by the design of existing micro-needling devices, and the speed of the actuation mechanism determined by the performance of comparable biopsy systems. This calculation can be altered by a skilled artisan for optimal treatment and/or effect. With the above-described assumptions, tissue ablation can last about 1 minute. The total duration of the procedure can also account for other steps, such as for the preparation of the skin (e.g., for cleaning and/or applying a local anesthetic) and/or application of compression wound dressing after tissue ablation. Including additional steps, the total procedure duration could be about ½ hour, and tissue ablation represents an insignificant fraction of the total procedure time. This estimated, non-limiting example of total procedure time is comparable to existing non-invasive skin resurfacing procedures, such as fractional laser treatment.

Example 12: Swine Skin Healing Progression after Treatment with Micro-Coring Needles The methods of the present invention were carried out in an animal model of skin resurfacing, and the progression of skin healing following ablation treatment was followed by staining biopsied skin samples. Specifically, a Yorkshire pig was treated by a series of ablations with a 19G diameter micro-coring needle and followed up for 90 days after treatment. Biopsy samples of the treated skin were taken on days 0, 7, 30, 60 and 90. The biopsied tissue was fixed in formalin, sliced, stained (Masson's trichrome stain), and photographed. FIG. 20 shows this healing progression after treatment. The full dermis is shown and sub-dermal fat can easily be seen on some of the photographs. Treatment sites were readily identified at Day 0, at which time cored regions were characterized by linear defects, sometimes containing blood, fibrin, and/or few inflammatory cells, extending from the skin surface through the dermis. These cored regions were progressively filled in by fibroproliferative tissue which exhibited maturation across subsequent time points. At Day 7, fibroproliferative tissue filled treatment tracts. The fibroproliferative tissue appeared moderately cellular and immature, sometimes with small amounts of remaining fibrin. At Day 30, treatment sites were indistinct from surrounding tissue, containing low cellularity, moderately dense collagen, and few capillaries with inflammatory cells, and normal epidermis was observed. The histologic appearance of treatment sites at Day 60 was similar to surrounding tissue. Normal epidermis was observed at Day 60. At Day 90, treatment sites were identifiable but very indistinct from surrounding tissue. The reparative fibrous tissue at treatment sites lacked the normal pre-treatment dermal architecture of thick and interwoven collagen bundles and elastic fibers. Instead, fibrous tissue at treatment sites consisted of denser sheets of thin collagen fibers lacking elastic fibers. Few capillaries permeated these areas. Inflammation at treatment sites was negligible to absent. From these results, it appeared that complete skin healing could be achieved within 60 days after treatment with micro-coring needles.

Example 13: Treated Abdominal Skin of a Human Subject

A clinical trial was initiated to evaluate the safety and efficacy of mechanical fractional ablation on the abdominal tissue of healthy patients. Subjects were treated with 19G to 24G diameter needles. Treatment coverage ranged from 5% to 20% of total skin area removed. FIG. 19 shows photographs of the abdominal skin of human subjects treated with different needle sizes immediately after treatment. Photograph 1 shows a matrix of six treatment zones (two columns, three rows) delimited by tattoo marks. 10% of the skin was removed in each of the six treated areas. A different needle gauge was used for each treatment area. Needle gauges range from 19G to 24G (see matrix next to the photograph for allocation of treatment areas to each needle gauge). Photograph 2 is similar to Photograph 1, except 20% of the skin was removed in each of the six treated areas. From this stage, a 21G needle diameter and treatment coverage of 10% were selected as safety threshold parameters. Selection criteria for the treatment parameters included absence of visible scars or other adverse events for up to three months after treatment. FIG. 20 further shows several graphs indicating the change in linear dimension/surface area of a treated square area (21G/10% or 22G/10%) in comparison with a contra-lateral non-treated area of similar dimension (control). The dimension of the treated square is consistently smaller than the dimension of the control square in a direction orthogonal to Langer lines. The same applies to its surface area.

Figure 21:
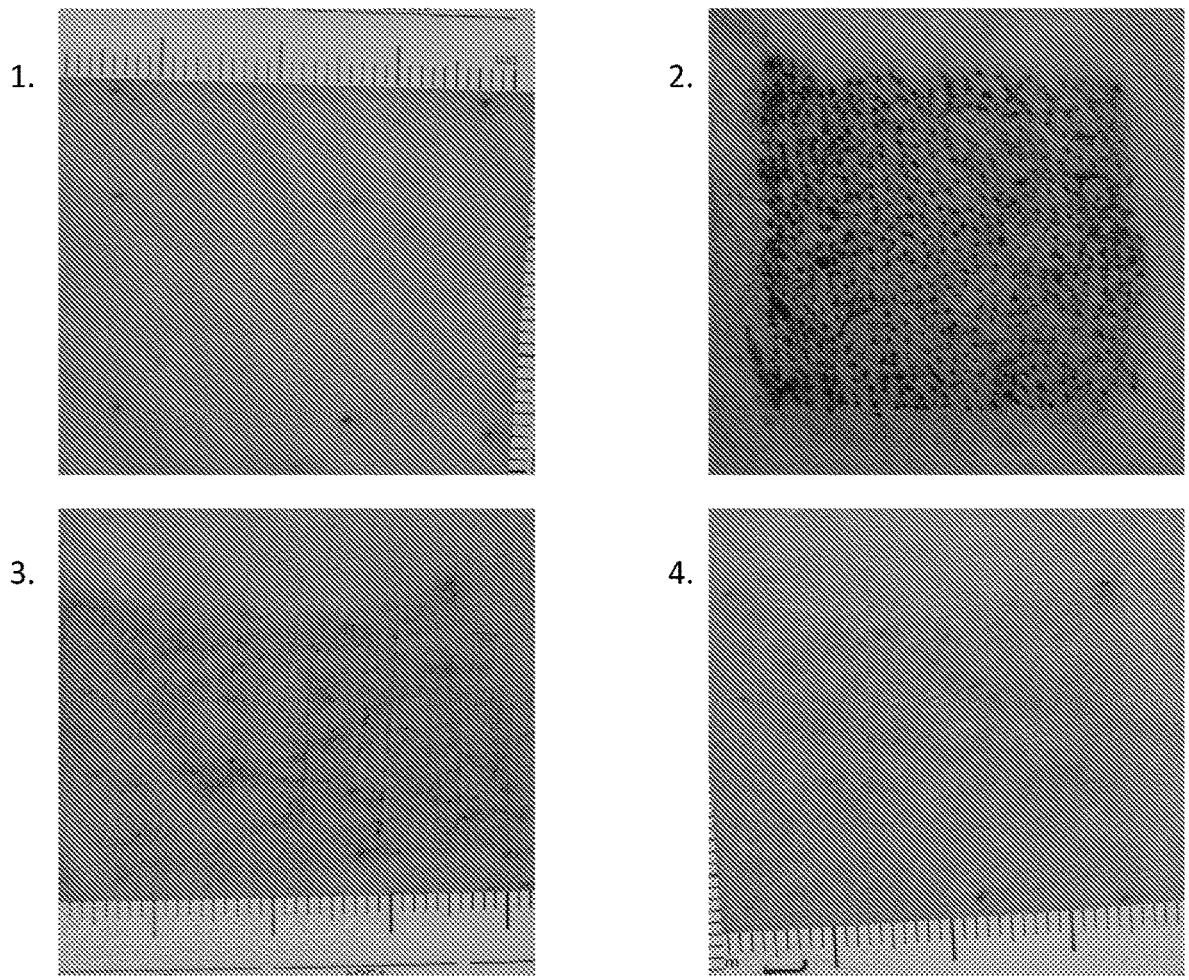
FIG. 21 shows a sequence of photographs taken before and after treatment of abdominal skin of a human subject.

Needles with 21G diameter were selected to use in the second stage of the study. Treatment and control sites were defined within the abdominal tissue area to be removed by the future abdominoplasty procedure. The subjects were treated by mechanical fractional ablation after local anesthesia and were evaluated on days 1, 7, 30, 60, and 90 post-procedure. FIG. 21 shows the appearance of human abdominal skin before and after the skin was treated with 21G diameter micro-coring needles. The same patch of skin is shown on all four photographs of FIG. 21. Photograph 1 was taken before treatment. The presence of tattoo marks delimits the treatment area. Photograph 2 was taken immediately after treatment. The skin was treated with 21G diameter micro-coring needles. 10% of the total skin surface area was removed. Photograph 3 was taken immediately after removal of the compressive wound dressing applied on the treatment area. Compression was applied in the vertical direction. Photograph 4 was taken a month after treatment. The treatment area is completely healed. Skin compression was achieved by removing 10% of the total skin surface area using 21G diameter micro-coring needles. The data demonstrate that the treatment is safe, does not generate scars, and results in reduction of the surface area of the treatment zone in a direction orthogonal to Langer lines.

Further, for mechanical fractional ablation, the extent and persistence of erythema appeared to correlate with the size of the coring needles used. No serious adverse effect, either device-related adverse effect or unanticipated adverse effect, has been reported to date. Pain levels of 2-4 (on a scale of 0=non pain to 10) were reported on the day of treatment, 0-2 on day 1 and 7, and dropping to 0 on day 30 and thereafter. None of the subjects patients reported taking pain medications after the procedure. Scarring was not observed with treatment coverage of 10% and 15% of total skin area removed (FIGS. 19 and 21) and with needle diameters of 21G and smaller.

OTHER EMBODIMENTS

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention are intended to be within the scope of the invention.

What is claimed is:

1. A device comprising an ablative apparatus for non-thermal tissue ablation, said apparatus comprising:
   a skin-penetrating component configured to provide an ablated tissue portion having a volume of less than 6 mm$^3$ and a change in width as a function of depth, wherein said change in width is of between about 100 µm to about 500 µm as a function of depth,
   wherein said skin-penetrating component is configured to provide the ablated tissue portion without transfer of thermal energy to tissue surrounding the ablated tissue portion; and
   wherein said skin-penetrating component comprises a drill configured to rotate at a speed of between 50 rpm and 2500 rpm; and
   a positioning apparatus for positioning skin, the positioning apparatus comprising a substrate and a cryosource, wherein the substrate is configurably attached to the cryosource and provides a cryotemperature to the skin of about 0 degrees C. or lower.

2. The device of claim 1, wherein
said skin-penetrating component is configured to provide an ablated tissue portion having a width to depth ratio of between about 1:0.3 to about 1:1 or of between about 1:25 to about 1:75.

3. The device of claim 1, wherein said apparatus further comprises one or more components that produce a mechanical force.

4. The device of claim 3, wherein said one or more components are selected from the group consisting of a motor, an axle, an adjustable depth stop, an in-flow tube, a return electrode, a generator, and an electrical insulator.

5. The device of claim 1, wherein said apparatus comprises a plurality of said skin-penetrating components in an array.

6. The device of claim 1, wherein said apparatus is configured to provide from about 10 to about 10000 ablated tissue portions per cm$^2$ area of the skin region.

7. The device of claim 1, wherein said ablative apparatus removes about 5% of skin within a treatment area.

8. The device of claim 1, further comprising a removal apparatus for removing one or more ablated tissue portion(s).

9. The device of claim 8, wherein the removal apparatus comprises a (i) substrate comprising a plurality of holes; and (ii) a vacuum source, wherein said substrate is configurably attached to said vacuum source to deliver vacuum through each hole and to each of said one or more ablated tissue portion(s).

10. The device of claim 8, wherein the removal apparatus comprises an adhesive layer or an array of probes configured to contact each of said one or more ablated tissue portion(s).

11. The device of claim 8, wherein the removal apparatus comprises
   (i) a wire having a first attachment point and a second attachment point;
   (ii) an axle having a sharpened distal end, a center portion, and a proximal end, wherein said first attachment point of said wire is configurably attached to said distal end of said axle and said second attachment point of said wire is configurably attached to said center portion of said axle, and wherein said axle is configured to contact each of said one or more ablated tissue portion(s);
   (iii) a motor configured to rotate said wire, wherein said motor is configurably attached to said proximal end of said axle;
   (iv) a vacuum source, and
   (v) a substrate comprising a plurality of holes, wherein said substrate is configurably attached to the vacuum source to deliver vacuum through each hole and to each of said one or more ablated tissue portion(s).

12. The device of claim 1, wherein the positioning apparatus comprises at least two sufficiently parallel tensioning rods configured to compress or stretch skin, wherein said rods are separated by a distance of more than about 0.5 mm and exert a compressing or stretching force, respectively.

13. The device of claim 1, wherein the positioning apparatus comprises a plurality of needles configured to grip skin, wherein said needles exert a gripping force.

14. The device of claim 1, wherein the positioning apparatus comprises a plurality of microhooks or microbarbs, wherein each microhook or microbarb is separated by a distance of more than about 0.5 mm and exerts a stretching force.

15. The device of claim 1, wherein the positioning apparatus comprises a vacuum tube having at least one dimension of greater than 1 mm and a vacuum source, wherein said vacuum tube is configurably attached to said source and exerts a stretching force.

16. The device of claim 1, wherein the positioning apparatus comprises a substrate having at least one dimension of about 1 mm and a cryosource, wherein said substrate is configurably attached to said cryosource and provides a cryotemperature of about 0° C. or lower.

17. The device of claim 1, wherein the positioning apparatus comprises an adhesive layer having at least one dimension of about 1 mm, wherein said positioning apparatus is configured to position skin prior to ablation with said ablative apparatus and/or prior to removal with said removal apparatus.

18. The device of claim 1, wherein the positioning apparatus comprises one or more sensors to detect position, temperature, skin proximity, skin contact, and/or changes in inductive coupling.

19. A method of treating skin, comprising:
   (i) positioning said skin using a compressive or a stretching force applied across said skin and providing a cryotemperature to the skin of about 0 degrees C. or lower;
   (ii) contacting the skin with a skin-penetrating component comprising a drill rotating at a speed of between 50 rpm and 2500 rpm;
   (iii) forming a plurality of ablated tissue portions having a volume of less than 6 mm$^3$ and a change in width as a function of depth without transfer of thermal energy to tissue surrounding the ablated tissue portion, wherein said change in width is of between about 100 μm to about 500 μm as a function of depth; and
   (iv) removing said plurality of ablated tissue portions, thereby treating said skin.

20. The method of claim 19, forming a plurality of ablated tissue portions having a width to depth ratio of between about 1:0.3 to about 1:1 or of between about 1:25 to about 1:75.

21. The method of claim 19, comprising removing said plurality of ablated tissue portions, wherein 5% of said skin within a treatment area is removed.

22. The method of claim 19, wherein said compressive force applied across said skin compresses said skin in a direction orthogonal to Langer lines.

23. The method of claim 19, further comprising positioning said skin using a compressive force applied across said skin prior to forming a plurality of ablated tissue portions and removing said plurality of ablated tissue portions.

* * * * *